US011542548B2

(12) United States Patent
Alisch et al.

(10) Patent No.: US 11,542,548 B2
(45) Date of Patent: Jan. 3, 2023

(54) BLOOD DNA METHYLATION BIOMARKER DIAGNOSTIC TEST FOR ANXIETY AND DEPRESSIVE DISORDERS

(71) Applicants: Wisconsin Alumni Research Foundation, Madison, WI (US); Emory University, Atlanta, GA (US)

(72) Inventors: Reid Spencer Alisch, Prairie du Sac, WI (US); Pankaj Chopra, Atlanta, GA (US)

(73) Assignees: Wisconsin Alumni Research Foundation;, Madison, WI (US); Emory University, Atlanta, GA (US)

(*) Notice: Subject to any disclaimer, the term of this patent is extended or adjusted under 35 U.S.C. 154(b) by 208 days.

(21) Appl. No.: 16/898,897

(22) Filed: Jun. 11, 2020

(65) Prior Publication Data

US 2020/0392560 A1 Dec. 17, 2020

Related U.S. Application Data

(60) Provisional application No. 62/860,022, filed on Jun. 11, 2019.

(51) Int. Cl.
*C12Q 1/686* (2018.01)
*C12Q 1/6883* (2018.01)

(52) U.S. Cl.
CPC ........... *C12Q 1/686* (2013.01); *C12Q 1/6883* (2013.01); *C12Q 2600/154* (2013.01)

(58) Field of Classification Search
CPC .............................. C12Q 2600/154
See application file for complete search history.

(56) References Cited

U.S. PATENT DOCUMENTS

| 6,872,816 B1 | 3/2005 | Hall et al. |
| 6,875,572 B2 | 4/2005 | Prudent et al. |
| 6,913,881 B1 | 7/2005 | Aizenstein et al. |
| 7,011,944 B2 | 3/2006 | Prudent et al. |

FOREIGN PATENT DOCUMENTS

| WO | WO 2000/070090 A1 | 11/2000 |
| WO | WO 2002/072880 A2 | 9/2002 |

OTHER PUBLICATIONS

Abdolmaleky, H. M. et al. Hypornethylation of MB-COMT promoter is a major risk factor for schizophrenia and bipolar disorder. Hum Mol Gene 15, 3132-3145, doi:10.1093/hmg/dd1253 (2006).
Alisch, R. S. et al. Differentially methylated plasticity genes in the amygdala of young primates are linked to anxious temperament, an at risk phenotype for anxiety and depressive disorders. J Neurosci 34, 15548-15556, doi:10.1523/JNEUROSCI.3338-14.2014 (2014).
Alisch, R. S. et al. A multi-dimensional characterization of anxiety in monozygotic twin pairs reveals susceptibility loci in humans. Translational psychiatry 7, 1282, doi:10.1038/s41398-017-0047-9 (2017).
Bartels, M., de Geus, E. J., Kirschbaurn, C., Sluyter, F. & Boomsma, D. I. Heritability of daytime cortisol levels in children. Behavior genetics 33, 421-433 (2003).
Bishop, S., Duncan, J., Brett, M. & Lawrence, A. D. Prefrontal cortical function and anxiety: controlling attention to threat-related stimuli. Nature neuroscience 7, 184-188, doi:10.1038/nn1173 (2004).
Burghy, C. A. et al. Developmental pathways to amygdala-prefrontal function and internalizing symptoms in adolescence. Nature neuroscience 15. 1736-1741. doi:10.1038/nn.3257 (2012).
Burghy, C. A. et al. Experience-Driven Differences in Childhood Cortisol Predict Affect-Relevant Brain Function and Coping in Adolescent Monozygotic Twins. Scientific reports 6, 37081, doi:10.1038/srep37081 (2016).
Collishaw, S. et al. Resilience to adult psychopathology following childhood maltreatment: evidence from a community sample. Child abuse & neglect 31, 211-229, doi:10.1016/j.chiabu.2007.02.004 (2007).
Dai, H. Q. et al. TET-mediated DNA demethylation controls gastrulation by regulating Lefty-Nodal signalling. Nature 538, 528-532, doi:10.1038/nature20095 (2016).
Day, S., and Mast, A. Invader assay, 2004; Chapter in Encyclopedia of Diagnostic Genomics and Proteomics.
Erickson, K., Drevets, W. & Schulkin, J. Glucocorticoid regulation of diverse cognitive functions in normal and pathological emotional states. Neuroscience and biobehavioral reviews 27, 233-246 (2003).
Essex, M. J., Klein, M. H., Cho, E. & Kalin, N. H. Maternal stress beginning in infancy may sensitize children to later stress exposure: effects on cortisol and behavior. Biological psychiatry 52, 776-784 (2002).
Feng, H., Conneely, K. N. & Wu, H. A Bayesian hierarchical model to detect differentially methylated loci from single nucleotide resolution sequencing data. Nucleic Acids Res 42, e69, doi:10.1093/nar/gku154 (2014).

(Continued)

*Primary Examiner* — Teresa E Strzelecka
(74) *Attorney, Agent, or Firm* — Daniel A. Blasiole; DeWitt LLP

(57) ABSTRACT

A method for diagnosing or giving a prognosis for anxious temperament or trait-like anxiety in a human or non-human primate subject comprising the steps of (a) obtaining DNA from a blood or saliva sample from the subject and (b) quantifying methylation in a set of differentially methylated regions (DMRs) selected from SEQ ID NOs:1-75 or DMR-associated genes selected from DIP2C, GRB10, INPP5A, C17ORF97, PDXK, CACNA2D4, TRAPPC9, CRTC1, MEGF6, HIVEP3, OPCML, PITPNM2, ZFPM1, RAP1GAP2, NFATC1, RNF126, FSTL3, GNAS, SH3BP2, NEURL1B, MAD1L1, HSPA12B, IGF2, PEG10, PEG3, SLC16A3, SYTL1, and ZIM2, wherein a significant change methylation indicates the present of anxious temperament or trait-like anxiety, wherein the change is relative to DNA from a second human or non-human primate who does not have anxious temperament or trait-like anxiety. Also disclosed is a biomarker panel of DMR and DMR-associated genes for the diagnosis or prognosis of anxious temperament or trait-like anxiety.

11 Claims, 33 Drawing Sheets
(32 of 33 Drawing Sheet(s) Filed in Color)

Specification includes a Sequence Listing.

(56) References Cited

OTHER PUBLICATIONS

Fox, A. S. et al. Central amygdala nucleus (Ce) gene expression linked to increased trait-like Ce metabolism and anxious temperament in young primates. Proc Natl Acad Sci U S A 109, 18108-18113, doi:10.1073/pnas.1206723109 (2012).

Gross, C. & Hen, R. The developmental origins of anxiety. Nature reviews. Neuroscience 5, 545-552, doi:10.1038/nrn1429 (2004).

Gunnar, M. & Quevedo, K. The neurobiology of stress and development. Annual review of psychology 58, 145-173, doi:10.1146/annurev.psych.58.110405.085605 (2007).

Hettema, J. M., Neale, M. C. & Kendler, K. S. A review and meta-analysis of the genetic epidemiology of anxiety disorders. The American journal of psychiatry 158, 1568-1578 (2001).

Hologic Inc.; invaderchemistry.com.

Kagan, J. & Snidman, N. Early childhood predictors of adult anxiety disorders. Biological psychiatry 46, 1536-1541 (1999).

Kalin, N. H. & Shelton, S. E. Nonhuman primate models to study anxiety, emotion regulation, and psychopathology. Ann N Y Acad Sci 1008, 189-200 (2003).

Kalin, N. H., Shelton, S. E. & Davidson, R. J. The role of the central nucleus of the amygdala in mediating fear and anxiety in the primate. J Neurosci 24, 5506-5515, doi:10.1523/JNEUROSCI.0292-04.2004 (2004).

Kappeler, L. & Meaney, M. J. Epigenetics and parental effects. BioEssays : news and reviews in molecular, cellular and developmental biology 32, 818-827, doi:10.1002/bies.201000015 (2010).

Klimes-Dougan, B., Hastings, P. D., Granger, D. A., Usher, B. A. & Zahn-Waxler, C. Adrenocortical activity in at-risk and normally developing adolescents: individual differences in salivary cortisol basal levels, diurnal variation, and responses to social challenges. Development and psychopathology 13, 695-719 (2001).

Krueger, F. & Andrews, S. R. Bismark: a flexible aligner and methylation caller for Bisulfite-Seq applications. Bioinformatics 27, 1571-1572, doi:10.1093/bioinformatics/btr167 (2011).

Kunde-Ramamoorthy, G. et al. Comparison and quantitative verification of mapping algorithms for Whole-genome bisulfite sequencing. Nucleic Acids Res 42, e43, doi:10.1093/nar/gkt1325 (2014).

Kuratomi, G. et al. Aberrant DNA methylation associated with bipolar disorder identified from discordant monozygotic twins. Molecular psychiatry 13, 429-441, doi:10.1038/sj.mp.4002001 (2008).

Kurdyukov and Bullock ("DNA methylation analysis: Choosing the right method," Biology, 2016, 5(3)).

Labrie, V., Clapcote, S. J. & Roder, J. C. Mutant mice with reduced NMDA-NR1 glycine affinity or lack of D-amino acid oxidase function exhibit altered anxiety-like behaviors. Pharmacology, biochemistry, and behavior 91, 610-620, doi:10.1016/j.pbb.2008.09.016 (2009).

Langmead, B. & Salzberg, S. L. Fast gapped-read alignment with Bowtie 2. Nature methods 9, 357-359, doi:10.1038/nmeth.1923 (2012).

Murphy, T. M. et al. Anxiety is associated with higher levels of global DNA methylation and altered expression of epigenetic and interleukin-6 genes. Psychiatric genetics 25, 71-78, doi:10.1097/YPG.0000000000000055 (2015).

Phelps, E. A. & LeDoux, J. E. Contributions of the amygdala to emotion processing: from animal models to human behavior. Neuron 48, 175-187, doi:10.1016/j.neuron.2005.09.025 (2005).

Poulter, M. O. et al. GABAA receptor promoter hypermethylation in suicide brain: implications for the involvement of epigenetic processes. Biological psychiatry 64, 645-652, doi:10.1016/j.biopsych.2008.05.028 (2008).

Qiagen, Cat# 972804 (Qiagen PyroMark Gold Q96 Reagents Handbook Aug. 2009, 36-38.

Renteria, M. E. et al. Genetic architecture of subcortical brain regions: common and region-specific genetic contributions. Genes, brain, and behavior 13, 821-830, doi:10.1111/gbb.12177 (2014).

Rodrigues, S. M., Bauer, E. P., Farb, C. R., Schafe, G. E. & LeDoux, J. E. The group I metabotropic glutamate receptor mGluR5 is required for fear memory formation and long-term potentiation in the lateral amygdala. J Neurosci 22, 5219-5229 (2002).

Schmidt, L. A. et al. Behavioral and neuroendocrine responses in shy children. Developmental psychobiology 30, 127-140 (1997).

Shackman, A. J. et al. Heightened extended amygdala metabolism following threat characterizes the early phenotypic risk to develop anxiety-related psychopathology. Molecular psychiatry, doi:10.1038/mp.2016.132 (2016).

Shirtcliff, E. A. & Essex, M. J. Concurrent and longitudinal associations of basal and diurnal cortisol with mental health symptoms in early adolescence. Developmental psychobiology 50, 690-703, doi:10.1002/dev.20336 (2008).

Speir, M. L. et al. The UCSC Genome Browser database: 2016 update. Nucleic Acids Res 44, D717-725, doi:10.1093/nar/gkv1275 (2016).

Stein, M. B., Simmons, A. N., Feinstein, J. S. & Paulus, M. P. Increased amygdala and insula activation during emotion processing in anxiety-prone subjects. The American journal of psychiatry 164, 318-327, doi:10.1176/ajp.2007.164.2.318 (2007).

Tsuji, J. & Weng, Z. Evaluation of preprocessing, mapping and postprocessing algorithms for analyzing whole genome bisulfite sequencing data. Briefings in bioinformatics 17, 938-952, doi:10.1093/bib/bbv103 (2016).

Urry, H. L. et al. Amygdala and ventromedial prefrontal cortex are inversely coupled during regulation of negative affect and predict the diurnal pattern of cortisol secretion among older adults. J Neurosci 26, 4415-4425, doi:10.1523/JNEUROSCI.3215-05.2006 (2006).

Van Hulle, C. A., Shirtcliff, E. A., Lemery-Chalfant, K. & Goldsmith, H. H. Genetic and environmental influences on individual differences in cortisol level and circadian rhythm in middle childhood. Hormones and behavior 62, 36-42, doi:10.1016/j.yhbeh.2012.04.014 (2012).

Verma, N. et al. TET proteins safeguard bivalent promoters from de novo methylation in human embryonic stem cells. Nat Genet 50, 83-95, doi:10.1038/s41588-017-0002-y (2018).

Waszczuk, M. A., Zavos, H. M., Gregory, A. M. & Eley, T. C. The phenotypic and genetic structure of depression and anxiety disorder symptoms in childhood, adolescence, and young adulthood. JAMA Psychiatry 71, 905-916, doi:10.1001/jamapsychiatry.2014.655 (2014).

Weaver, I. C. et al. Epigenetic programming by maternal behavior. Nature neuroscience 7, 847-854, doi:10.1038/nn1276 (2004).

Wu, H. et al. Detection of differentially methylated regions from whole-genome bisulfite sequencing data without replicates. Nucleic Acids Res 43, e141, doi:10.1093/nar/gkv715 (2015).

BLOOD DNA METHYLATION BIOMARKER DIAGNOSTIC TEST FOR ANXIETY AND DEPRESSIVE DISORDERS

CROSS-REFERENCE TO RELATED APPLICATIONS

This application claims priority to U.S. Provisional Application No. 62/860,022, filed Jun. 11, 2019, which is incorporated herein by reference in its entirety.

STATEMENT REGARDING FEDERALLY SPONSORED RESEARCH

Not applicable

REFERENCE TO A SEQUENCE LISTING SUBMITTED VIA EFS-WEB

The content of the ASCII text file of the sequence listing named "960296 04029 ST25.txt" which is 44.6 kb in size was created on Jun. 4, 2020 and electronically submitted via EFS-Web herewith the application is incorporated herein by reference in its entirety.

BACKGROUND

Anxiety is frequently characterized by a negative affective response that is associated with the anticipation of encountering a potential threat. Trait-like anxiety in humans and non-human primates is associated with stable individual differences in hypothalamic-pituitary-adrenal (HPA) axis activation and amygdala function. HPA activation results in the release of cortisol, and increased cortisol concentrations in children and adolescents can be linked to inhibited behaviors and anxiety that often persist throughout life.

Additionally, a loss of the 'natural' circadian decline in afternoon/evening cortisol levels has been correlated with shyness and later alterations in behavior, including internalizing problems, suggesting that late-in-the day cortisol levels in children and adolescents may be an index of early life and current stress exposure as well as altered behaviors. High afternoon cortisol levels in childhood are also negatively correlated with amygdala-prefrontal cortex connectivity in adolescents and adults, indicating that a disruption in amygdala function is related to trait-like anxiety. In fact, anxiety prone individuals show greater amygdala activation during emotion processing tasks, further supporting a central role of the amygdala in processing of fearful stimuli.

Moreover, lesions in the central nucleus of the amygdala of non-human primates results in decreased adrenocorticotropic hormone (ACTH) concentrations before and after stressful conditions. Finally, higher and prolonged amygdala metabolism following a stressful challenge results in increased anxiety-like behaviors (e.g., freezing) in young rhesus monkeys, suggesting that the timing of amygdala activation and deactivation, in both humans and rhesus monkeys, is associated with trait-like anxiety.

Genetic data suggest that common anxiety disorders like generalized and social anxiety disorders are ~20%-40% heritable and that environmental factors—potentially including epigenetic modifications—likely account for much of the remaining variability. Studies using adult postmortem brain tissue support a role for DNA methylation (i.e., 5-methylcytosine [5mC]) in the development of anxiety, bipolar disorder, schizophrenia, and major depressive disorder.

SUMMARY OF THE INVENTION

In a first aspect, provided herein is a method of amplifying at least one of six differentially methylated region (DMR) associated genes comprising the steps of: (a) providing a reaction mixture comprising bisulfite modified target DNA from a subject and at least one pair of primers designed to amplify at least one DMR-associated gene selected from the group consisting of DIP2C, INPP5A, PDXK, GNAS, GRB10, and TRAPPC9 wherein the primer pair comprises a first and a second primer that are complementary to the DMR-associated gene; (b) heating the reaction mixture to a first predetermined temperature for a first predetermined time; (c) cooling the reaction mixture to a second predetermined temperature for a second predetermined time under conditions to allow the first and second primers to hybridize with their complementary sequences on the target DNA; and (d) repeating steps (b) and (c) wherein an amplified target DNA sample is formed. In some embodiments, the reaction mixture additionally comprises a polymerase and a plurality of free nucleotides comprising adenine, thymine, cytosine, and guanine. In some embodiments, the reaction mixture additionally comprises a reaction buffer and $MgCl_2$.

In some embodiments, in step (a), (i) a first reaction mixture comprising a first portion of bisulfite modified target DNA and a pair of primers designed to amplify DIP2C; (ii) a second reaction mixture comprising a second portion of bisulfite modified target DNA and a pair of primers designed to amplify INPP5A; (iii) a third reaction mixture comprising a third portion of bisulfite modified target DNA and a pair of primers designed to amplify PDXK; (iv) a forth reaction mixture comprising a forth portion of bisulfite modified target DNA and a pair of primers designed to amplify GNAS; (v) a fifth reaction mixture comprising a fifth portion of bisulfite modified target DNA and pair of primers designed to amplify GRB10; and (vi) a sixth reaction mixture comprising a sixth portion of bisulfite modified target DNA and a pair of primers designed to amplify TRAPPC9 are provided.

In some embodiments, the primers are specific for a DMR selected from the group consisting of SEQ ID NOs: 7-18, 50-59, 67-69, and 73-75. In some embodiments, at one of primers in the primer pair is biotinylated.

In some embodiments, the methods described herein include providing subsequent reaction mixtures comprising subsequent portions of bisulfite modified target DNA and a pair of primers designed to amplify one or more DMR-associated genes selected from the group consisting of C17ORF97, CACNA2D4, CRTC1, MEGF6, HIVEP3, OPCML, PITPNM2, ZFPM1, RAP1GAP2, NFATC1, RNF126, FSTL3, SH3BP2, NEURL1B, MAD1L1, HSPA12B, IGF2, PEG10, PEGS, SLC16A3, SYTL1, and ZIM2. In some embodiments, the primers are designed to amplify a DMR selected from the group consisting of SEQ ID NOs:1-6, 19-49, 60-66, and 70-72.

In some embodiments, the target DNA is isolated from a blood sample or a saliva sample form the subject. In some embodiments, the subject is a human or non-human primate.

In a second aspect, provided herein is a biomarker panel comprising probes specific to DIP2C, INPP5A, PDXK, GNAS, GRB10, and TRAPPC9. In some embodiments, the biomarker panel additionally comprises pairs of primers designed to amplify DIP2C, INPP5A, PDXK, GNAS, GRB10, and TRAPPC9.

In some embodiments, either the probes or the primers are arrayed on a substrate. In some embodiments, the substrate is selected from the group consisting of a chip, a bead, a plate, a microfluidic device, or a multiwall plate.

In some embodiments, the primers are designed to amplify SEQ ID NOs: 7-18, 50-59, 67-69, and 73-75.

In some embodiments, the biomarker panel additionally comprises probes specific to HIVEP3, C17orf97, ZFPM1, RAP1GAP2, NFATC1, IGF2, SLC16A3, and SYTL1. In some embodiments, the probes are specific to SEQ ID NOs: 3-6, 19-20, 27-37.

In some embodiments, the biomarker panel additionally comprises probes specific to CACNA2D4, CRTC1, MEGF6, OPCML, PITPNM2, ZIM2, RNF126, FSTL3, SH3BP2, NEURL1B, MAD1L1, HSPA12B, PEG10, and PEGS. In some embodiments, the probes are specific to SEQ ID NOs: 1-2, 21-26, 38-49, 60-66, and 70-72.

In a third aspect, provided herein is a biomarker panel comprising the sequences of SEQ ID NOs: 7-18, 50-59, 67-69, and 73-75. In some embodiments, the sequences of SEQ ID NOs: 7-18, 50-59, 67-69, and 73-75 are arrayed on a substrate. In some embodiments, the substrate is selected from the group consisting of a chip, a bead, a plate, a microfluidic device, or a multiwall plate. In some embodiments, the biomarker panel additionally comprises the sequences of SEQ ID NOs: 1-2, 21-26, 38-49, 60-66, and 70-72. In some embodiments, the biomarker panel additionally comprise the sequences of SEQ ID NOs:3-6, 19-20, and 27-37.

In a forth aspect, provided herein is a method of diagnosing anxious temperament in a subject comprising the steps of: (a) obtaining a blood sample or saliva sample from the subject; (b) isolating target DNA from the sample obtained in (a); (c) contacting a biomarker panel as described herein with the isolated target DNA; (d) amplifying DMR-associated genes DIP2C, INPP5A, PDXK, GNAS, GRB10, and TRAPPC9; (e) quantifying methylation in the amplified DMR-associated genes, whereby a change in methylation of at least 10% compared to methylation in the same genes from a subject unaffected by anxious temperament indicates the presence of anxious temperament in the subject.

BRIEF DESCRIPTION OF DRAWINGS

The patent or patent application file contains at least one drawing in color. Copies of this patent or patent application publication with color drawings will be provided by the Office upon request and payment of the necessary fee.

DETAILED DESCRIPTION OF THE DISCLOSURE

Figure 1:
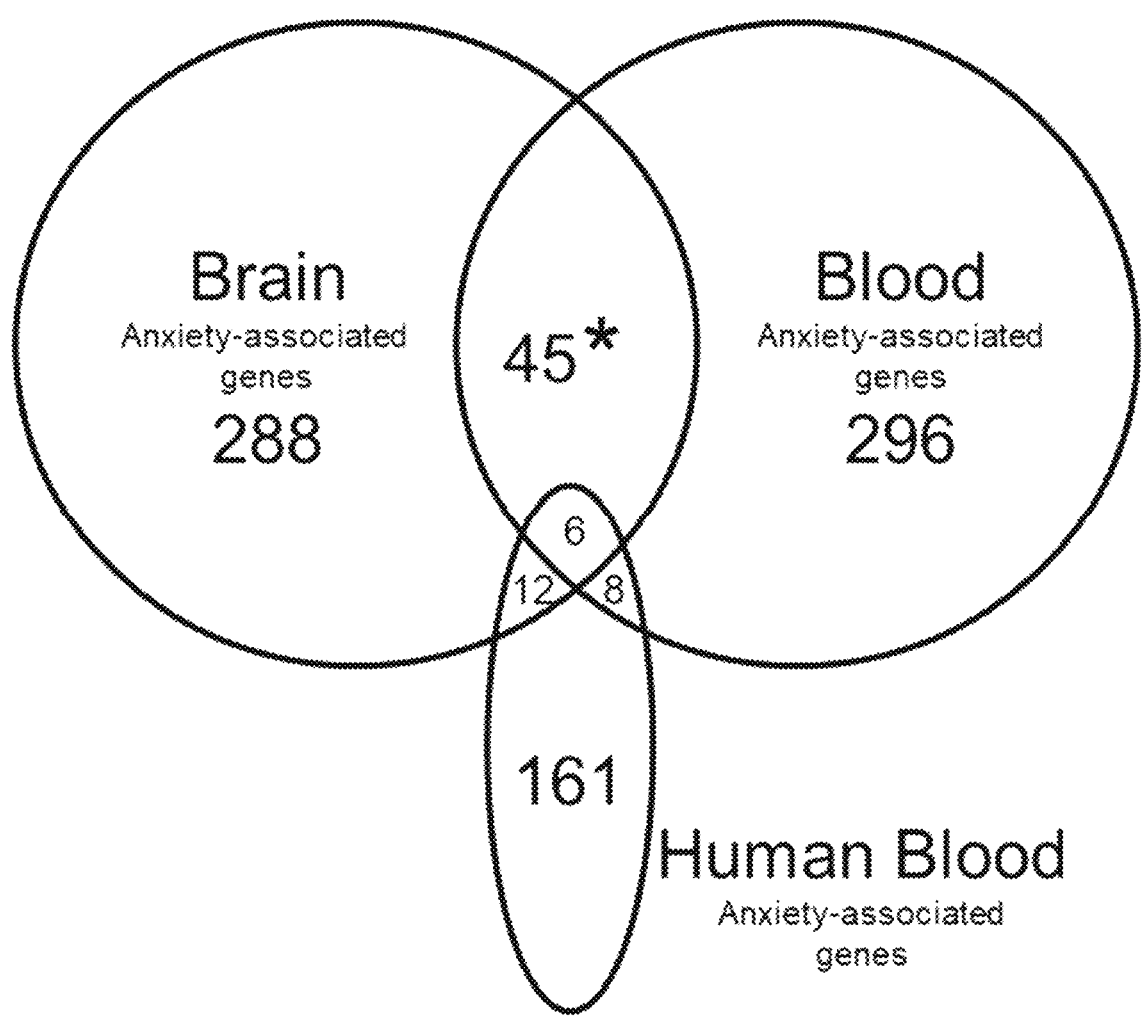
FIG. 1 shows overlap of differentially methylated region associated genes identified from monkey brain, monkey blood, and human blood.

Recent study in young monkeys, as well as studies in humans, identified differentially methylated genes that are implicated as risk factors for anxiety and depressive disorders. Thus, these studies support the hypothesis that DNA methylation may have an important role in the risk to develop trait-like anxiety. However, these studies have relied heavily on the ability to access brain tissue. Focusing studies on anxiety-related DNA methylation profiles in blood has the potential to provide tools that could be clinically utilized to improve diagnostic and treatment strategies. Therefore, a need in the art exists for blood sample or saliva sample-based diagnostic tests for anxiety in primates.

The present disclosure describes blood sample or saliva sample based assays for the diagnosis, prognosis, and modified therapeutic response to anxiety in primates. The present disclosure describes differentially methylated regions (DMRs) associated with 22 different genes that are characteristic of anxious temperament and trait-like anxiety in primates. These characteristic biomarkers may be used to assay methylation in DNA isolated from a primate blood sample or a primate saliva sample. These characteristic biomarkers may be used in the development of a screening panel, a resequencing panel, or a diagnostic kit for the processing of DNA isolated from a primate blood sample or a primate saliva sample.

As used herein, "anxious temperament," or "AT" refers to the disposition of a human or non-human primate who is sensitive to new social experiences, shows increased freezing behavior, decreased communications, and increased pituitary-adrenal and autonomic activity. In non-human primates, AT can be computed and quantified as a composite measure among vocalizations, cortisol levels and freezing time assessed during the no eye contact condition of the human intruder paradigm. An individual can have an AT composite phenotype score between −1.48 to 1.43, with the higher scores correlated with increased freezing, decreased communication, increased cortisol levels, or a combination thereon. At risk children score at least 1.5 standard deviations above and below the mean on at least one of eight parent-reported symptom scales of the Health and Behavior Questionnaire (Essex M J, et al., Biological psychiatry, 2002). Because AT reflects a continuous trait-like variable, individuals will have a broad range of AT-related scores.

As used herein, "trait-like anxiety," refers to stable individual differences in hypothalamic-pituitary-adrenal (HPA) axis activation and amygdala function. (Kagan J, et al., Biological psychiatry. 1999; Kalin N H, Shelton S E. Ann N Y Acad Sci. 2003).

Biomarker Candidates

Described herein are differentially methylated regions associated with 22 different genes that are characteristic of anxious temperament and trait like anxiety.

As used herein, "differentially methylated region" or "DMR" refers to CpG dinucleotide regions with a significant increase (hypermethylation) or a significant decrease (hypomethylation) in methylation (e.g, 5-methylcytosine (5mC)) relative to control. The control is considered the level of methylation measured in a DNA sample from a primate unaffected by AT or trait-like anxiety. In some embodiments, the DMR corresponds to a region with a change in methylation of at least about 8%, at least about 10%, at least about 12%, at least about 15% or at least about 20% when compared to control. In some embodiments, the DMR corresponds to a region with at least 10% increase in methylation compared to control. In some embodiments, the DMR corresponds to a region with at least 10% decrease in methylation compared to control.

As used herein, "significant increase" refers to an increase with a statistical significance of $p<0.05$ when compared to control.

As used herein, "significant decrease" refers to a decrease with a statistical significance of p<0.05 when compared to control.

As used herein, "differentially methylated region-associated genes" or "DMR-associated genes" refers to the genes in which the DMRs are located or most closely associated with. In some embodiments, the DMR may be in the coding region of the DMR-associated gene. In some embodiments, the DMR may be in the promoter region of the DMR-associated gene.

DMR biomarker candidates associated with genes DIP2C, GRB10, INPP5A, C17ORF97, PDXK, CACNA2D4, TRAPPC9, CRTC1, MEGF6, HIVEP3, OPCML, PITPNM2, ZFPM1, RAP1GAP2, NFATC1, RNF126, FSTL3, GNAS, SH3BP2, NEURL1B, MAD1L1 HSPA12B, IGF2, PEG10, PEG5, SLC16A3, SYTL1, and ZIM2 show significant (p<0.05) changes in methylation in target regions when DNA samples from anxious and unaffected (control) primates are compared.

Applicant notes that U.S. Provisional Application No. 62/860,022, the whole genome bisulfate sequence data was mapped to the rhesus macaque genome (rheMac8) and then annotated to "refseq" genes to get the gene symbols to orient the location of DNA methylation data to genes. This approach resulted in about ~6,000 gene symbol annotations to the data. However, this annotation was limited due to the low number of gene symbols found related to the data. Subsequence improved gene annotation methods and the use of Ensembl gene symbols provided more than 16,000 gene annotations to the rhesus macaque data. RNA sequencing data from the rhesus macaque brain tissue and the RSEM pipeline was also annotated to the Ensembl gene symbols. Using Ensembl gene symbols for both the DNA methylation and RNA sequence data allowed comprehensive comparisons between these data. Therefore, while particular gene symbols may be revised or updated from U.S. Provisional Application No. 62/860,022, this is an artifact of the gene annotation assembly used. The updated gene symbols are reflected herein and consistent with the DMRs recited in the provisional application.

TABLE 1

Anxiety-Associated Genes

| Gene Symbol | Gene Name |
|---|---|
| DIP2C | disco interacting protein 2 homolog C |
| GRB10 | growth factor receptor bound protein 10 |
| INPP5A | inositol polyphosphate-5-phosphatase A |
| C17orf97 | chromosome 16 open reading frame, human C17orf97 |
| PDXK | pyridoxal kinase |
| CACNA2D4 | calcium voltage-gated channel auxiliary subunit alpha2delta 4 |
| TRAPPC9 | trafficking protein particle complex 9 |
| CRTC1 | CREB regulated transcription coactivator 1 |
| MEGF6 | multiple epidermal growth factor-like domains protein 6 |
| HIVEP3 | human immunodeficiency virus type I enhancer-binding protein 3 |
| OPCML | opioid-binding cell adhesion molecule |
| PITPNM2 | phosphatidylinositol transfer protein membrane associated 2 |
| ZFPM1 | zinc finger protein multitype 1 |
| RAP1GAP2 | Ras-proximate-1 (RAP1) GTPase activating protein 2 |
| NFATC1 | nuclear factor of activated T-cells, cytoplasmic 1 |
| RNF126 | ring finger protein 126 |
| FSTL3 | follistatin Like 3 |
| GNAS | guanine nucleotide-binding protein G(s) subunit alpha |
| SH3BP2 | SH3 domain-binding protein 2 |
| NEURL1B | neuralized E3 ubiquitin protein ligase 1B |
| MAD1L1 | mitotic arrest deficient 1 like 1 |
| HSPA12B | heat shock protein family A (Hsp70) member 12B |
| IGF2 | insulin like growth factor 2 |
| PEG10 | paternally expressed 10 |
| PEG3 | paternally expressed 10 |
| SLC16A3 | solute carrier family 16 member 3 |
| SYTL1 | synaptotagmin like 1 |
| ZIM2 | zinc Finger Imprinted 2 |

DMR biomarkers are recited in Table 2. These biomarkers represent CpG regions with at least about 10% differential methylation in target regions when DNA samples from anxious and unaffected (control) primates are compared. Differential methylation includes both hypermethylation and hypomethylation.

TABLE 2

Overlapping AT-related DMRs

| Chromosome | Start | End | Gene Symbol | ReSeq panel ID | Overlap | DMR Status | SEQ ID NO: |
|---|---|---|---|---|---|---|---|
| Chr 1 | 3503131 | 3503245 | MEGF6 | RhBrn_26 | ** | Hyper | 1 |
| Chr 1 | 3540349 | 3540490 | MEGF6 | HuBld_196 | ** | Hyper | 2 |
| Chr 1 | 27349740 | 27349796 | SYTL1 | RhBld_38 | ## | Hyper | 3 |
| Chr 1 | 27349814 | 27350119 | SYTL1 | HuBld_4 | ## | Hyper | 4 |
| Chr 1 | 41540915 | 41541160 | HIVEP3 | HuBld_171 | ## | Hyper | 5 |
| Chr 1 | 41618187 | 41618276 | HIVEP3 | RhBld_22 | ## | Hyper | 6 |
| Chr 10 | 309028 | 309164 | DIP2C | RhBld_230 | *** | Hyper | 7 |
| Chr 10 | 329499 | 329561 | DIP2C | RhBld_243 | *** | Hyper | 8 |
| Chr 10 | 355287 | 355459 | DIP2C | RhBld_232 | *** | Hyper | 9 |
| Chr 10 | 355461 | 355490 | DIP2C | RhBld_1000 | *** | Hyper | 10 |
| Chr 10 | 355492 | 355503 | DIP2C | RhBld_1001 | *** | Hyper | 11 |
| Chr 10 | 355504 | 355516 | DIP2C | RhBld_1002 | *** | Hyper | 12 |
| Chr 10 | 355517 | 355541 | DIP2C | RhBld_1003 | *** | Hyper | 13 |
| Chr 10 | 413853 | 414117 | DIP2C | HuBld_28 | *** | Hyper | 14 |
| Chr 10 | 484804 | 484931 | DIP2C | RhBrn_215 | *** | Hyper | 15 |
| Chr 10 | 132607036 | 132607056 | INPP5A | RhBrn_218 | *** | Hypo | 16 |
| Chr 10 | 132607057 | 132607061 | INPP5A | RhBrn_1002 | *** | Hypo | 17 |
| Chr 10 | 132616356 | 132616412 | INPP5A | HuBld_122 | *** | Hypo | 18 |
| Chr 11 | 2133265 | 2133335 | IGF2; | RhBld_355 | ## | Hyper | 19 |
| Chr 11 | 2133341 | 2133722 | IGF2; INS-IGF2 | HuBld_67 | ## | Hyper | 20 |

TABLE 2-continued

Overlapping AT-related DMRs

| Chromosome | Start | End | Gene Symbol | ReSeq panel ID | Overlap | DMR Status | SEQ ID NO: |
|---|---|---|---|---|---|---|---|
| Chr 11 | 133081982 | 133082177 | OPCML | HuBld_56 | ** | Hyper | 21 |
| Chr 12 | 1811666 | 1811837 | CACNA2D4 | HuBld_180 | ** | Hyper | 22 |
| Chr 12 | 1838231 | 1838295 | CACNA2D4 | RhBrn_300 | ** | Hyper | 23 |
| Chr 12 | 1842428 | 1842506 | CACNA2D4 | RhBrn_298 | ** | Hyper | 24 |
| Chr 12 | 123034226 | 123034317 | PITPNM2 | HuBld_153 | ** | Hypo | 25 |
| Chr 12 | 123077953 | 123078020 | PITPNM2 | RhBrn_295 | ** | Hypo | 26 |
| Chr 16 | 88500291 | 88500408 | ZFPM1 | HuBld_154 | ## | Hypo | 27 |
| Chr 16 | 88534642 | 88534701 | ZFPM1 | RhBld_495 | ## | Hypo | 28 |
| Chr 17 | 410141 | 410147 | C17orf97 | RhBld_1008 | ## | Hypo | 29 |
| Chr 17 | 414205 | 414425 | C17orf97 | HuBld_143 | ## | Hypo | 30 |
| Chr 17 | 2837445 | 2837518 | RAP1GAP2 | RhBld_403 | ## | Hypo | 31 |
| Chr 17 | 2852762 | 2852873 | RAP1GAP2 | HuBld_159 | ## | Hypo | 32 |
| Chr 17 | 82235989 | 82236062 | SLC16A3 | HuBld_170 | ## | Hypo | 33 |
| Chr 17 | 82238736 | 82238899 | SLC16A3 | RhBld_404 | ## | Hypo | 34 |
| Chr 18 | 79436203 | 79436269 | NFATC1 | RhBld_449 | ## | Hyper | 35 |
| Chr 18 | 79509085 | 79509203 | NFATC1 | HuBld_123 | ## | Hyper | 36 |
| Chr 18 | 79523293 | 79523358 | NFATC1 | RhBld_455 | ## | Hyper | 37 |
| Chr 19 | 659125 | 659132 | RNF126 | RhBrn_491 | ** | Hyper | 38 |
| Chr 19 | 659138 | 659172 | RNF126 | RhBrn_1011 | ** | Hyper | 39 |
| Chr 19 | 659175 | 659216 | RNF126 | RhBrn_1012 | ** | Hyper | 40 |
| Chr 19 | 659431 | 659723 | RNF126 | HuBld_79 | ** | Hyper | 41 |
| Chr 19 | 676722 | 676962 | FSTL3 | HuBld_108 | ** | Hypo | 42 |
| Chr 19 | 18762214 | 18762355 | CRTC1 | RhBrn_478 | ** | Hyper | 43 |
| Chr 19 | 18777827 | 18778074 | CRTC1 | HuBld_49 | ** | Hyper | 44 |
| Chr 19 | 56838765 | 56839239 | ZIM2; PEG3 | HuBld_13 | ** | Hypo | 45 |
| Chr 19 | 56840640 | 56840712 | RF02151; PEG3 | RhBrn_1009 | ** | Hypo | 46 |
| Chr 19 | 56840714 | 56840745 | RF02151; PEG3 | RhBrn_1010 | ** | Hypo | 47 |
| Chr 20 | 3751818 | 3752296 | HSPA12B | HuBld_2 | ** | Hyper | 48 |
| Chr 20 | 3751944 | 3752172 | HSPA12B | RhBrn_246 | ** | Hyper | 49 |
| Chr 20 | 58839989 | 58840198 | GNAS; GNAS-AS1 | HuBld_38 | *** | Hyper | 50 |
| Chr 20 | 58850827 | 58850895 | GNAS; GNAS-AS1 | HuBld_136 | *** | Hyper | 51 |
| Chr 20 | 58855291 | 58855453 | GNAS | RhBrn_1000 | *** | Hyper | 52 |
| Chr 20 | 58889570 | 58890047 | GNAS | HuBld_1 | *** | Hyper | 53 |
| Chr 20 | 58890242 | 58890319 | GNAS | RhBld_1004 | *** | Hyper | 54 |
| Chr 21 | 43725878 | 43725960 | PDXK | HuBld_195 | *** | Hypo | 55 |
| Chr 21 | 43727343 | 43727431 | PDXK | RhBld_1007 | *** | Hypo | 56 |
| Chr 21 | 43758088 | 43758098 | PDXK | RhBrn_1005 | *** | Hypo | 57 |
| Chr 21 | 43758106 | 43758177 | PDXK | RhBrn_1006 | *** | Hypo | 58 |
| Chr 21 | 43758178 | 43758183 | PDXK | RhBrn_1007 | *** | Hypo | 59 |
| Chr 4 | 2805929 | 2805990 | SH3BP2 | HuBld_199 | ** | Hypo | 60 |
| Chr 4 | 2825167 | 2825265 | SH3BP2 | RhBrn_141 | ** | Hypo | 61 |
| Chr 5 | 172669962 | 172670083 | NEURL1B | RhBrn_145 | ** | Hyper | 62 |
| Chr 5 | 172683900 | 172684098 | NEURL1B | HuBld_9 | ** | Hyper | 63 |
| Chr 7 | 1946572 | 1946581 | MAD1L1 | RhBrn_97 | ** | Hypo | 64 |
| Chr 7 | 1946583 | 1946636 | MAD1L1 | RhBrn_1003 | ** | Hypo | 65 |
| Chr 7 | 2113040 | 2113199 | MAD1L1 | HuBld_121 | ** | Hypo | 66 |
| Chr 7 | 50782213 | 50782314 | GRB10 | HuBld_52 | *** | Hyper | 67 |
| Chr 7 | 50782337 | 50782376 | GRB10 | RhBrn_1001 | *** | Hyper | 68 |
| Chr 7 | 50783121 | 50783181 | GRB10 | RhBld_1005 | *** | Hyper | 69 |
| Chr 7 | 94656373 | 94656577 | PEG10 | HuBld_60 | ** | Hypo | 70 |
| Chr 7 | 94658334 | 94658421 | PEG10 | RhBrn_68 | ** | Hypo | 71 |
| Chr 7 | 94658422 | 94658431 | PEG10 | RhBrn_1008 | ** | Hypo | 72 |
| Chr 8 | 140098781 | 140098880 | TRAPPC9 | RhBrn_192 | *** | Hyper | 73 |
| Chr 8 | 140098798 | 140098899 | TRAPPC9 | RhBld_208 | *** | Hyper | 74 |
| Chr 8 | 140099819 | 140100255 | TRAPPC9 | HuBld_12 | *** | Hyper | 75 |

** monkey brain and human blood overlap
monkey blood and human blood overlap
*** monkey brain, monkey blood, and human blood overlap

TABLE 3

DMR Sequences:

| SEQ ID NO: | Chr. | Start | End | hg38coord | cdna |
|---|---|---|---|---|---|
| 1 | Chr 1 | 3503131 | 3503245 | chr1: 3503131- 3503245 | CGCTGAGGCCCTGAGGACACACCCTGGTGAACCCTTG TCACCAGGGCCCATCCCCAGGGGCACCCGCCCATAGG GACACAGGCACGTCCCTGGGACTACAGGCCTGGCACT CACC |
| 2 | Chr 1 | 3540349 | 3540490 | chr1: 3540349- 3540490 | CGGGTTTCCCGCTGCACTGGGAAGACAGCCAGCTGAA GAATGTTGGCCTGGGGAGGCCCAGATTCAGCCACCCA CAGGAACGTGGCCCCAGCTTTGCAACCGGAAGGCCCA GGTTCAGGCCTGGGCTCCAGGGCCCATGGGC |
| 3 | Chr 1 | 27349740 | 27349796 | chr1: 27349740- 27349796 | CGGTGTCCAGCCTTAACTCCTCCACGGTGAGGCGGGA GGGAGGGGACCCGGGCGGCC |
| 4 | Chr 1 | 27349814 | 27350119 | chr1: 27349814- 27350119 | CGATGCGTAGCCCCTGCCTGCCCCTCCCTCGCCGCGG GACCCACCGCTGCAGCCCCCCAGCCTGCCACCTATGA CCCGGGTCTGAAGCCTCCGCGCTGCCCGCGGCCCCGA CGTGAGCCCTGCGAGCGGCCCTGACTCCCACCCACTC CCGTCCGCAGCTGAGCGGCAGCCAGATGAGCCTGTCA GGCGACGCGGAGGCGGTGCAGGTCCGCGGCTCCGTGC ACTTCGCGCTGCACTACGAGCCGGGCGCCGCCGAGCT GCGCGTGCACGTGATCCAGTGCCAGGGCCTGGCCGCC GCCCGGCGCC |
| 5 | Chr 1 | 41540915 | 41541160 | chr1: 41540915- 41541160 | CGGGTTTAGCTGGACTCTAAATGGACACTGCAACCAC ACTGGTGCTCCAGACATAAACAGCCAGTAGGTGAGTG GGTGGGAAAACAGGAAGGAAGGGAGGGTGTGGTCACG GCTCAGAGGACTGAGGTGGCCTGTCTGATTAGGACGC TGCGAGTGCAGTGGTTAGGCATGGGGTGTTGATGCAT CAGACTGCCGAGTTCAAATCCTGCCTCCTCCGACCAG CTGTGTGATCCTGAGCAAGCACCC |
| 6 | Chr 1 | 41618187 | 41618276 | chr1: 41618187- 41618276 | CGCTGCGGGATGGTGCCAGAGCCCGGAGCCACCAGGC TTGCCACTCTGGCTGCCACACAGAAGAGTCTCCTTGC GCTCAGCAGACTCTGC |
| 7 | Chr 4 | 2805929 | 2805990 | chr4: 2805929- 2805990 | CGCGGGGAGACGCCTGTTCTGGAGGCCAGGCCCGCAG GCAGGAAGGAAAAGCACGGCCGGAC |
| 8 | Chr 4 | 2825167 | 2825265 | chr4: 2825167- 2825265 | CGAAAAGAAAGACCTGCCCTTGGACACCAGGTGAGCC CGGGCCCAGGGCATACCGGGCAGTGAGGGTCCCTGGG GCGCCTGGGCCTGACCCGGGTGTCC |
| 9 | Chr 5 | 172669962 | 172670083 | chr5: 172669962- 172670083 | CGTTCACGCAGCGGCCCATCCGGCTGTACGAGCAGGT GCGGCTGCGCCTGGTGGCCGTGCGCCCTGGCTGGAGC GGCGCGCTGCGCTTCGGCTTCACCGCGCACGATCCGT CGCTCATGAGC |
| 10 | Chr 5 | 172683900 | 172684098 | chr5: 172683900- 172684098 | CGAGCTGCCCGCCGACCCAGACGCGCTGCTCGACCGC AAAGAGTACTGGGTGGTGGCGCGCGCCGGGCCCGTGC CGAGCGGCGGCGACGCGCTCAGCTTCACGCTGCGGCC CGGCGGCGACGTGCTCCTGGGCATCAACGGGCGTCCG CGCGGCCGCCTGCTGTGCGTCGACACCACGCAGGCGC TCTGGGCCTTCTTC |
| 11 | Chr 7 | 1946572 | 1946581 | chr7: 1946572- 1946581 | TGACTCAACA |
| 12 | Chr 7 | 1946583 | 1946636 | chr7: 1946583- 1946636 | AAATCTTTCACTTGCAGAGCGAGCAGGCGCTCTGGTG CTGCTACCCAGCGCGGT |
| 13 | Chr 7 | 2113040 | 2113199 | chr7: 2113040- 2113199 | CGACGAGGGGCAGAGCCTCCCTCAGCAAAGCGTCCCA CTCAGGAAACGGGGACGAGGGGCAGAGCCTCCCTCAG CAAAGCGTCCCACTCAGGAAACGGGGACGAGGGGCAG AGCCTCCCTCAGCAAAGCGTCCCACTCAGGAAACACG GAAGAGACGGGC |
| 14 | Chr 7 | 50782213 | 50782314 | chr7: 50782213- 50782314 | CGGCAACGAAGCTCGGGATCTCGGACTGCAGCGAGCC CGCGGCAGGCGGGCAGGGGCCGCGCGGCAAGACCTC CCCGCCTCCCTCCCGGGCCCTGTCCGCC |

TABLE 3-continued

DMR Sequences:

| SEQ ID NO: | Chr. | Start | End | hg38coord | cdna |
|---|---|---|---|---|---|
| 15 | Chr 7 | 50782337 | 50782376 | chr7: 50782337- 50782376 | GCGCAGGCCGATCCGCCCGCCGCCCCGGCTCGCGCCC ACC |
| 16 | Chr 7 | 50783121 | 50783181 | chr7: 50783121- 50783181 | GCAGACAGGCGGGGACATCGCGGCCGCGGCAAGCTA GAGATGCCGCCTGCTCGAGCAACC |
| 17 | Chr 7 | 94656373 | 94656577 | chr7: 94656373- 94656577 | CGCGCTTCAACTTCGGTTGGTGTGTGTCGAAGAAACC TGACTGCGCCCTGAGGAGAACAGCGGAGAAGGTCCAC CGAGCCTGGCGAAAGGTCCGCTGAGCGGGCTGTCGTC CGGAGCCACTCCGGGCTGCGGAGCACCCAGTGGAGAC CGCGCCTGGCTCAGGTGTGGGACCCCATCCTTCCTGT CTTCGCAGAGGAGTCCTCGC |
| 18 | Chr 7 | 94658334 | 94658421 | chr7: 94658334- 94658421 | CTGGGCCCGCCTCCTCTGAGGTGAACTGCCCAGGCCC CGCCTCTCCTGGGCCCGCCTCCTCTGATGTGAGCTCA CCCAGATCCCACCT |
| 19 | Chr 7 | 94658422 | 94658431 | chr7: 94658422- 94658431 | CCCCAGGCCC |
| 20 | Chr 8 | 140098781 | 140098880 | chr8: 140098781- 140098880 | CGCCCACCCAGGTCCTCCGCAGCTGTCCGCAGGGGAA GACACCAGCTAGATGTAAGTGCGCAGCTGCAGCAATC CCGCGATCCACAAAGTAATGACGCCC |
| 21 | Chr 8 | 140098798 | 140098899 | chr8: 140098798- 140098899 | CGCAGCTGTCCGCAGGGGAAGACACCAGCTAGATGTA AGTGCGCAGCTGCAGCAATCCCGCGATCCACAAAGTA ATGACGCCCGCCCAGATCCTCCGCAGCC |
| 22 | Chr 8 | 140099819 | 140100255 | chr8: 140099819- 140100255 | CGCTGGTCCTCCGCAGCCTTCTCCAGGGGAGGACACC CAGCTAGGTCTCTGCGCAGCTGCAGGAGTGCCACAAT CCTCAGGGTACTGACGCTCACCCAGGTCCTCCGCAGC CTTCCGCAGGGGAGATACCCAGCTAGGTCTCAGCGCG CAGCTTCAGCATCCCCGCGATCCGCAGAGTATTGACG CCCACCCGGGTCCTCCGCAGCCTAGAGCAAGGGACTG CGGAACGAGTGCCGCAATCTTCAGGGTATTGACGCCC ACCCGGGTCCTCCGCAGCCAAGAGCAAGGGACTGCGG AAGGAGTGCCGCAATCTTCAGGGTATTGACGCCCACC CGGGTCCTCCGCAGCCTAGAGCAGGGAACTGCGGAAA GAGTGCCACAATCCTCAGGGTATTGACGCCCACCCAA GTCCTCCGCAGCCTTCCGCAGGGGAGATAC |
| 23 | Chr 10 | 309028 | 309164 | chr10: 309028- 309164 | CGGAGCGGCTGCTGACGGCGATAAGGGAAGGCACCAT GTCCCACGCACTTCACCTAAGCAACAATGAACGGGCA CCTCTACAGTCACCAAGTGGAAGATGATCTGTTTCAA CGGGGGAAGTCTGCAGTAAAAATGAC |
| 24 | Chr 10 | 329499 | 329561 | chr10: 329499- 329561 | CGTGTCTCGGACTTTGTACTGACTCACGGCAAGAAGC CACAAGGCGGGGTTGGTTTCCAGCTC |
| 25 | Chr 10 | 355287 | 355459 | chr10: 355287- 355459 | CGACACGCGCTTCTCTGGCAGAGGAGGAGGAGAGGTT GTTCCTATGAACTAAGCCACGTGCAGAGAATGGTCTG ATAACTGAAACTCAAACCAGAGAGTCGGGGAATAATT TCGTGATGCTGCTGGCATTTCCTTTTGTCTTCAATCT GCTGCTTCGCACACTAAGATTTTGA |
| 26 | Chr 10 | 355461 | 355490 | chr10: 355461- 355490 | ACTCAGCAATTCTAAACAGCCATGACTTTT |
| 27 | Chr 10 | 355492 | 355503 | chr10: 355492- 355503 | GAAGAGTTGCAA |
| 28 | Chr 10 | 355504 | 355516 | chr10: 355504- 355516 | GTACCTATACTTG |
| 29 | Chr 10 | 355517 | 355541 | chr10: 355517- 355541 | TCAAGAAGACTTACATTTTTCTTCC |

TABLE 3-continued

DMR Sequences:

| SEQ ID NO: | Chr. | Start | End | hg38coord | cdna |
|---|---|---|---|---|---|
| 30 | Chr 10 | 413853 | 414117 | chr10:<br>413853-<br>414117 | CGTTCGGGAGTGGCTGTGCGAGGGGTGGGCAAAGGG<br>CAGAGAGTGAGCCTGGGGATTACCGTAAGTGAGGATG<br>TAGAGGGGCTTCCCGTTGGTGTCCATGGTGGTCAGGC<br>AGGGCGCCTTGGGCGAGATGGTGCCCCACCTCTGCAG<br>TGCGGCCTCCAGCGACGGCGGCCAGTTCGTGACCACG<br>CCCAGCTGCTCTCCGCGCATGGCCAGCATCTGGGCCC<br>CCTCCGGCTTTGGTTGGTTCGGATCCGGTTGTTGAAC<br>TAAATC |
| 31 | Chr 10 | 484804 | 484931 | chr10:<br>484804-<br>484931 | CGGTTCCCTGCGGTGCTGGCCACCCGCTCCCGAGCCG<br>CAGCTTCTCGGACGTCGCACACCCCGATGTGGGCAGA<br>GCGGAATGTTCTCCTCGGCGCTCCTTCACTGTGCTGC<br>AGTCTACACCGAACCAC |
| 32 | Chr 10 | 132607036 | 132607056 | chr10:<br>132607036-<br>132607056 | CGGCTTGTGCTGAGTGCTCGC |
| 33 | Chr 10 | 132607057 | 132607061 | chr10:<br>132607057-<br>132607061 | GCTCA |
| 34 | Chr 10 | 132616356 | 132616412 | chr10:<br>132616356-<br>132616412 | CGTGGCGTGCGGGGACGCCGTGGGCGTGGTGTGAGGT<br>ATGTGGCGTGCGGGGACGCC |
| 35 | Chr 11 | 2133265 | 2133335 | chr11:<br>2133265-<br>2133335 | CGCTCTTCCGCCTGAGCCGCCCGCCTGACCTGACAGG<br>CCACCCCTGTGACTGATCAGTGACTTGAGCTAAT |
| 36 | Chr 11 | 2133341 | 2133722 | chr11:<br>2133341-<br>2133722 | CGGGCAGAGGGACAGAAGGAGCCAGCGTCTGAGCTGC<br>TCCCGGGCCACACAGCAAGCAAGGAAGTCACGGGTCC<br>TTGTCCCTGGCCAAGAGGTCCCAGAGGCCACAGGAAA<br>CGCTGGGCGCCCGAAGCCCTATTTCTCTGTCTCTAGA<br>GAGTGGGAAAGGGGCCCAGGACCCTCACCGGAAGCAC<br>GGTCGGAGGGGTCGACACGTCCCTCTCGGACTTGGCG<br>GGGGTAGCACAGTACGTCTCCAGGAGGGCCAGGTCAC<br>AGCTGCGGAAACAGCACTCCTCAACGATGCCACGGCT<br>GCGACGGCTCACACGGCTTGCGGGCCTGCCTGGAAGT<br>CCCACAGCACAGAGAGAGCCGTGTTAGCACCGCACTG<br>ACCCCAGCCCCC |
| 37 | Chr 11 | 133081982 | 133082177 | chr11:<br>133081982-<br>133082177 | CGGGAAGTTCTGTCCCTGCTCCCGAGTGTGCCCAGAG<br>TCCTGCCGTTTCCTTCTAGCGCGCGTTCTTTACTGGC<br>GCCATTCCTGCTGCTAAGAGCCCTGAGACGGCCGGGG<br>GTGACCCGGGCCCAGAGCAGCTCCCGGCTCAGGGACC<br>CCTCCCCAGGCCAAGGGCAGGACAAGCCCGGGCCTGG<br>GCCTCCGCCTC |
| 38 | Chr 12 | 1811666 | 1811837 | chr12:<br>1811666-<br>1811837 | CGCGTTGCCGCCCAGAATTTGCGCTGGAGGAATTCCA<br>GCTTCATTTGGACGCCCGCGGCTACAGGGCAGAAAGA<br>GAGAGGGCAAGGCCAGGGAAGAGACGGGGAGAGAAAA<br>AAATAGAGTCAAGTTAAAGAGAGGAGGTGCTTCCGCA<br>GGAACTGAGGAGAGAGACCGCAGC |
| 39 | Chr 12 | 1838231 | 1838295 | chr12:<br>1838231-<br>1838295 | CGGTGGTGTTATACACGGCAGTGACGCGCAGCCCGCC<br>ACTGCCCCCGTGGCTGGGCTGAGTGCCC |
| 40 | Chr 12 | 1842428 | 1842506 | chr12:<br>1842428-<br>1842506 | CGCGGTTGTTTTCCTTCTTTTGGGGTGGAAGGGAGTG<br>TGCAGAGGTGGCCATGTGTCTAAGCGTGTGTGTGCGC<br>TGAGC |
| 41 | Chr 12 | 123034226 | 123034317 | chr12:<br>123034226-<br>123034317 | CGTCTGGGCCAGGGAGATAATGGTGCTGAACGCAAGG<br>GCAAGTGTTCGCGTTGTAGGCGGCGGGACACAGTGCC<br>GGGAAAGCAATCTGATGCC |
| 42 | Chr 12 | 123077953 | 123078020 | chr12:<br>123077953-<br>123078020 | CACGCAGCTCTCCCAGCAGCCCATGCCTGGAGACAGA<br>GGACACTGAGGAGCACGCGTGTCCCAGGAT |

TABLE 3-continued

DMR Sequences:

| SEQ ID NO: | Chr. | Start | End | hg38coord | cdna |
|---|---|---|---|---|---|
| 43 | Chr 16 | 88500291 | 88500408 | chr16: 88500291- 88500408 | CGGGGACACAGCCAGCTCCCCCCATGAGCTGGTGGCC TCGTCAGGAAGACGGCCACAGGGCGCTCTTGGGAGGA CCCTTGGGACAGTGGGCAGGCGCTGGGCAAGCCACAA GCGTGTC |
| 44 | Chr 16 | 88534642 | 88534701 | chr16: 88534642- 88534701 | CGGCCGACCGCGGCCCCTCGCCCGCTCCCGCCCCCGC CGCCTCCCCGCAGCCCGGGTCCC |
| 45 | Chr 17 | 410141 | 410147 | chr17: 410141- 410147 | CGCACCG |
| 46 | Chr 17 | 414205 | 414425 | chr17: 414205- 414425 | CGTATCTGAAGGAAACAGATGTTCGGTACACGGACGA CGCCGACTCTCCCATCACCAAGCTGCCCTCGGTTGCC CAGGAGAGCCACAGTGCCTTGAGAACATAAGCAATTT AGTGAACAGAGTTCTTTTCAGAATTTCCTTTTTCTTA AGTAAGCATCTCTGTTACTTAATTTCTCACCACAGCT AGATGTCTATAATCTGCCCCAAAAAGAAAAGAAAGC |
| 47 | Chr 17 | 2837445 | 2837518 | chr17: 2837445- 2837518 | CGGAGCAGGCAGAAAGGCATATTCCGCTTCGTCTGGT GATGGGCATCGGGAGTCTCTGGCCGAGTCAGCTCCTC |
| 48 | Chr 17 | 2852762 | 2852873 | chr17: 2852762- 2852873 | CGGGAGGGGGCTGGGAGGCTGGGCAGCACCTGGAAGT GGATGAGGGCGATTGTGAGCGAGGCCCCGCGCCGATG GTAGGGACCAGGCCACAGCCCTTTCCCCAGGAGCCGG C |
| 49 | Chr 17 | 82235989 | 82236062 | chr17: 82235989- 82236062 | CGGAACCAACCCTCCTGGCCATGGGAGGGGCCGTGGT GGACGAGGGCCCCACAGGCGTCAAGGCCCCTGACGGC |
| 50 | Chr 17 | 82238736 | 82238899 | chr17: 82238736- 82238899 | CGTGTTCATCCTGGCGGGGGCCGAGGTGCTCACCTCC TCCCTGATTTTGCTGCTGGGCAACTTCTTCTGCATTA GGAAGAAGCCCAAAGAGCCACAGCCTGAGGTGGCGGC CGCGGAGGAGGAGAAGCTCCACAAGCCTCCTGCAGAC TCGGGGTGGACTTGC |
| 51 | Chr 18 | 79436203 | 79436269 | chr18: 79436203- 79436269 | CGCTTTTCAGAAACGAGGCTCATCGCACTGGCCTGGG GGCGCGAGGACGAGGCCGTGGGTAGTGGGC |
| 52 | Chr 18 | 79509085 | 79509203 | chr18: 79509085- 79509203 | CGCATGGAAGGAAACGCCATTGCTGGGCAGTGTTGCA GCCTCCGCAGAGGTGTGTGGGCTCCGGGGAGAGGGAC GTGCTGGCCCCTGTGCAGTGGCGTGGCCCGTGTCCTT TCCCCGCC |
| 53 | Chr 18 | 79523293 | 79523358 | chr18: 79523293- 79523358 | CGTTCAGGCCCTGGCAGCTCCGTTCTGGCCCTCATCA TTCCCAGCATAGAGAAACAAACTCCTGC |
| 54 | Chr 19 | 659125 | 659132 | chr19: 659125- 659132 | AGAGGCAG |
| 55 | Chr 19 | 659138 | 659172 | chr19: 659138- 659172 | GGCTGTCACTGTCACGGTATCTGGCACAACCGCAG |
| 56 | Chr 19 | 659175 | 659216 | chr19: 659175- 659216 | ACACAGAGCAAGCAGCGGCCAGAGACAGACCCAGGCC GTCTT |
| 57 | Chr 19 | 659431 | 659723 | chr19: 659431- 659723 | CGGAGGTTGCAGGCGTTCGGGGTGGGGGGTCGGCAG GCAGAGCTGGAACCACCCTAGGAACCACCCAGAGACG GGGAGGTCAGGGGCAAGGACACGCACGCAGGGCCACCT CCCTGCGCCCGCCTGGTTCCTGGGGGCTCAGTGCCCT CAGCAGCTCTCGCCCACACCCTACAGTCACAGCTCCA GTCAGTGCCTCCTCAGCAGGCTCGAGTCTGGGTCTGC GCAGCCGCCTGTGGCCTGAGCTCCAGCTGGCCTGTCT GGTTCCTGCCGCCACACGCCCCACTCTGGCTGAC |

TABLE 3-continued

DMR Sequences:

| SEQ ID NO: | Chr. | Start | End | hg38coord | cdna |
|---|---|---|---|---|---|
| 58 | Chr 19 | 676722 | 676962 | chr19: 676722-676962 | CGCTGACATTTATTGAGCGCTTAGTGTCTACCTCTCC CCTCCCTGAACCTGTGCCATCCCGATAGTGCCGGAGC TCTCTTCATCTCCGTCTTCCAGATGGGGAAACTGAGG CTCAGGGTCACACAGCCTGTAGCAGGCAAAGCCAGGG TTCTAGCCGCGACCGTCCGGGTCGGTCCTGGTGCCGA GAGGTAGTGCTGGGTGTCGGGAGCCAGGCCCTCCAGC TGGGGCTGAGAGCTTTCCC |
| 59 | Chr 19 | 18762214 | 18762355 | chr19: 18762214-18762355 | CGCCCGGGAGCTGCGCACCTCCAGCAGGCACCCAGTC TAAACAAGCACAAGGAAACACACAACATACGTGGAAG CTGGAGCCGGCGCTGGCCAGAGCGGCCCGGTAATGCC TGACATGTGTTGGGTTGTTTGTGAACCTGCC |
| 60 | Chr 19 | 18777827 | 18778074 | chr19: 18777827-18778074 | CGGTCCCCCAGCCCATCCGCCATCCCCAGCCCGTGGT CAGGTAGAGAGTGAGCCCCACGCCGCCCCAGGGAGGA GGCGCCAGAGCGCGGGGCAGACGCAAAGTGAAATAAA CACTATTTTGACGGCTGTCTTTTATATTTCTGAGCAC ACACAGAGCCCTGGCGTCCACCGGGGCAGGCGCAAAG TGGACAGAGCATGCAGGGCGGCGGACCCCCCCACGAC CCTCCTCGCCCTGTCTCCATCCCCTC |
| 61 | Chr 19 | 56838765 | 56839239 | chr19: 56838765-56839239 | CGACCAGCACACACAGCCCAAGGAGCGCGGCACTCCA CAGCTTTCCATCACCGCAAGGCAGGCAAGCACAGCAA CCGTGGCCCCGCCCCTCCCTGTGGACAACCCCACACC TATGCGGCAAACCGCAGCCGCCCCGATCAAAGATGGC ACCCAGGTGGGCGGGGCTTGAACAGACCGTCCCGCCC ATGCCACCTGCAGCCACTTCAGCCTTGCCCCGCCGCA TCTGCCGCCAACCAATCCGGGCAACGCCTGCGCGGCA AACCTCAGCTGCCCCCATCAAAGATGGCGCCCAGGCG GGCGGGCCTTGTCTCGCCCAACCAACTAGGACAGCGC CTGCGCAGCAAATCTCAAGCACTTTCATTAAAGATGG CGCCCAGGTGGGTGGGGCTTGAACAAACCACTAGGTC AATGCCACCCTGTCACTTCAGCCTTGCCCCGCCCCA TCTGCCACCAACCAACCAGGACAGCACCTGC |
| 62 | Chr 19 | 56840640 | 56840712 | chr19: 56840640-56840712 | GCCCGGCGCCCGGCGGCGCCACCAGCCCAGGGTGGAC ATCTCCCGCGCCTCCCAAACCTCTCCTCCCGCAGCT |
| 63 | Chr 19 | 56840714 | 56840745 | chr19: 56840714-56840745 | CCCAGACTTCTGCACCGAGGTGCAGCTCGACG |
| 64 | Chr 20 | 3751818 | 3752296 | chr20: 3751818-3752296 | CGACGTCTTCGAGCGCTTCGTGGCCGCCGAGCAGTCG GTGGCCCTGGGCGAGGAGGTGCGGCGCAGCTACTGCC CGGCGCGTCCCGGCCAGCGGCGCGTACTCATCAACCT GTACTGCTGCGCGGCAGAGGATGCGCGCTTCATCACC GACCCCGGCGTGCGCAAATGCGGCGCGCTCAGCCTCG AGCTTGAGCCCGCCGACTGCGGCCAGGACACCGCCGG CGCGCCTCCCGGCCGCCGCGCGAGATCCGCGCGCCATG CAGTTTGGCGACACCGAAATTAAGGTCACCGCCGTCG ACGTCAGCACCAATCGCTCCGTGCGCGCGTCCATCGA CTTTCTTTCCAACTGAGGGCGCGCCGGCGCGGTGCCA GCGCCGTCTGCCCGGCCCCGCCCTCTTTCGGTTCAGG GGCCTGCGGAGCGGGTTGGGGCGGGGAAACGATAGT TCTGCAGTCTGCGCCTTTCCACGCCCTCCAGCCCC |
| 65 | Chr 20 | 3751944 | 3752172 | chr20: 3751944-3752172 | AGAGGATGCGCGCTTCATCACCGACCCCGGCGTGCGC AAATGCGGCGCGCTCAGCCTCGAGCTTGAGCCCGCCG ACTGCGGCCAGGACACCGCCGGCGCGCCTCCCGGCCG CCGCGAGATCCGCGCCGCCATGCAGTTTGGCGACACC GAAATTAAGGTCACCGCCGTCGACGTCAGCACCAATC GCTCCGTGCGCGCGTCCATCGACTTTCTTTCCAACTG AGGGCGC |
| 66 | Chr 20 | 58839989 | 58840198 | chr20: 58839989-58840198 | CGGGCCAGCTTCTCACCTCATAGGGTGTACCTTTCCC GGCTCCAGCAGCCAATGTGCTTCGGAGCCACTCTCTG CAGAGCCAGAGGGCAGGCCGGCTTCTCGGTGTGTGCC TAAGAGGATGGATCGGAGGTCCCGGGCTCAGCAGTGG CGCCGAGCTCGCCATAATTACAACGACCTGTGCCCGC CCATAGGCCGCCGGGCAGCCACCGC |

TABLE 3-continued

DMR Sequences:

| SEQ ID NO: | Chr. | Start | End | hg38coord | cdna |
|---|---|---|---|---|---|
| 67 | Chr 20 | 58850827 | 58850895 | chr20:58850827-58850895 | CGCCATACACCCGCCCCCACCGGCTTCCAACCACCC CAGCAGCACCTCTTGGGCGTTCCAACGCGGC |
| 68 | Chr 20 | 58855291 | 58855453 | chr20:58855291-58855453 | GAAAAGATGGGCTACATGTGTACGCACCGCCTGCTGC TTCTAGGTAATGCGGCGGACTCTGCCTGCGGGCAGCA GGGCCGCCGGGGAACCGGGGAGGGGGTGGCAGGGCTG CCTGGTGGGGCTAGGGGCTCCGCAGTGGGAGGAGGGG GTCCAGCCAAAGGCG |
| 69 | Chr 20 | 58889570 | 58890047 | chr20:58889570-58890047 | CGCGCCTTTGCACTTTTCTTTTTGAGTTGACATTTCT TGGTGCTTTTTGGTTTCTCGCTGTTGTTGGGTGCTTT TTGGTTTGTTCTTGTCCCTTTTTCGTTTGCTCATCCT TTTTGGCGCTAACTCTTAGGCAGCCAGCCCAGCAGCC CGAAGCCCGGGCAGCCGCGCTCCGCGGCCCCGGGGCA GCGCGGCGGGAACCGCAGCCAAGCCCCCCGACACGGG GCGCACGGGGGCCGGGCAGCCCGAGGCCGGGGCAAG CAGGGAGCCCGGGCCAGGCGCGAGCCGAGCTCCCCGA GGTGGCCGGGCCACCATGCTGAAGATGGCCATGAAGC TCAAAGCCCGGGCGGCGGAGAGCGAGAAGAAGACGGC CGCGGCGGCTGCCGAGGTGGCTGCCGAAGCTGCGGCG GCGGCTGCGGCGTTGGCCGAGCCGAGAGAGCCGCTCG CGCCGCGAAGAGCGGGGACCCCGAGAAGCTCGC |
| 70 | Chr 20 | 58890242 | 58890319 | chr20:58890242-58890319 | GATGCCCCGAGGCCGCCGCCGCCGCGGCCGCCGCCGA CGACGACGAGGGCGCCGAGGAGGGCGCCGTCGGGGGC GCCG |
| 71 | Chr 21 | 43725878 | 43725960 | chr21:43725878-43725960 | CGGTGGCCCGCACTAACTTCCTTAGAGGTGATGCTGA TGCTGTATGTTGGAGACGCTTCTGAGTGTCCTCGGAA CGTTCCCAC |
| 72 | Chr 21 | 43727343 | 43727431 | chr21:43727343-43727431 | GCCGAGGAGGGGCCGGCAGCGCCTCCCTTCCTGCCCA CAGAGCAGCCGCCTTGTGCCCATCTATTCCCCGGCTC TGCATGGGGCCTCTG |
| 73 | Chr 21 | 43758088 | 43758098 | chr21:43758088-43758098 | GCAGTGTCAGG |
| 74 | Chr 21 | 43758106 | 43758177 | chr21:43758106-43758177 | CTCCTTCTGCCCCTGCAGTGGGTGTTACGGGCGGTGT GCCCTGGCGAGCAAGCTTTGATTCTTGGTTCTTTG |
| 75 | Chr 21 | 43758178 | 43758183 | chr21:43758178-43758183 | AGCTCG |

Any combination of DMRs outlined in Table 2 may be used to diagnose or give a prognosis of AT or trait-like anxiety in a human or non-human primate. Any combination of DMRs outlined in Table 2 may be used in an assay to quantify methylation. Any combination of DMRs outlined in Table 2 or DMR-associated genes outline in Table 1 may be used in an assay to amplify the DMRs or DMR-associated genes for sequencing to quantify methylation.

In some embodiments, the DMRs of interest are SEQ ID NOs:7-18, 50-59, 67-69, and 73-75. In some embodiments, the DMR-associated genes of interest are DIP2C, GRB10, INPP5A, GNAS, PDXK, and TRAPPC9. These DMRs and DMR-associated genes showed differential methylation across samples from non-human primate brain, non-human primate blood, and human blood. In some embodiments, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, or all 28 of the DMRs of SEQ ID NOs: 7-18, 50-59, 67-69, and 73-75 are assayed to diagnose or give a prognosis of AT or trait-like anxiety in a human or non-human primate. In some embodiments, at least 1, at least 2, at least 3, at least 4, at least 5, at least or all 6 of the DMR-associated genes are assayed to diagnose or give a prognosis of AT or trait-like anxiety in a human or non-human primate.

In some embodiments, the DMRs of interest are SEQ ID NOs:3-6, 19-20, and 27-37. In some embodiments, the DMR-associated genes of interest are HIVEP3, C17orf97, ZFPM1, RAP1GAP2, NFATC1, IGF2, SLC16A3, and SYTL1. These DMRs and DMR-associated genes showed differential methylation across samples from non-human primate blood and human blood. In some embodiments, at least 1, at least 2, at least 3, at least 4, at least 5, at least 6, at least 7, at least 8, at least 9, at least 10, at least 11, at least 12, at least 13, at least 14, at least 15, at least 16, or all 17 of these DMRs are assayed to diagnose or given a prognosis of AT or trait-like anxiety in a human or non-human primate. In some embodiments, at least 1, at least 2, at least 3, at least 4, at least 5, at least 6, at least 7 or all 8 of the DMR-associated genes are assayed to diagnose or give a prognosis of AT or trait-like anxiety in a human or non-human primate.

In some embodiments, the DMRs of interest are SEQ ID NOs: 1-2, 21-26, 38-49, 60-66, and 70-72. In some embodiments, the DMR-associated genes of interest are CACNA2D4, CRTC1, MEGF6, OPCML, PITPNM2, ZIM2, RNF126, FSTL3, SH3BP2, NEURL1B, MAD1L1, HSPA12B, PEG10, and PEG5. These DMRs and DMR-associated genes showed differential methylation across samples from human blood and non-human primate brain. In some embodiments, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or all 30 of these DMRs are assayed to diagnose or give a prognosis of AT or trait-like anxiety in a human or non-human primate. In some embodiments, at least 1, at least 2, at least 3, at least 4, at least 5, at least 6, at least 7, at least 8, at least 9, at least 10, at least 11, at least 12, at least 13, or all 14 of the DMR-associated genes are assayed to diagnose or give a prognosis of AT or trait-like anxiety in a human or non-human primate.

Biomarker Panels

In some embodiments, the biomarkers described herein are used in the production of a biomarker panel for use in assaying DNA methylation. The biomarker panel includes probes or primers specific to the sequences of the DMRs or DMR-associated genes disclosed herein. In some embodiments, the biomarker panel includes probes or primers specific to the sequences of the DMR-associated genes listed in Table 1. In some embodiments, the biomarker panel includes probes or primers specific to the DMRs listed in Table 2.

Primers specific to the DMRs or DMR-associated genes disclosed herein are between about 10 base pairs (bp) and about 40 bp and are complementary to sequences upstream and downstream of the DMR or DMR-associated gene of interest. Generally, a pair of forward and reverse primers that are designed to be complementary to the sequences flanking the DMR or DMR-associated gene are included. The size of the fragment to be amplified by the primer pair can range from less than 50 bp to greater than 10,000 bp. Primers can be designed that are complementary to a sequence less than 50 bp upstream of the DMR or more than 1,000 bp upstream depending on the sequence technology selected and the application of the biomarker panel. Therefore, it is possible to design many permutations of primer sets that are capable of amplifying a given DMR or DMR-associated gene of interest. For example, a given sample containing genomic DNA with a 500 bp DMR, a primer set can be designed to amplify i) the exact target region; or ii) a region encompassing the DMR including upstream and downstream regions.

Probes specific to the DMRs or DMR-associated genes disclosed herein are between about 10 bp and about 40 bp and are commentary to sequences including or adjacent to the DMR or DMR-associated gene of interest. In some embodiments, the probe is complementary to the DMR of interest.

The disclosure includes a number of preferred primers and probes for amplification, selection, and identification of specific DMRs or DMR-associated genes. However, a skilled artisan will appreciate that the DMRs and DMR-associated genes disclosed can be amplified, selected, and identified by primers and probes other than those specific disclosed, which have been presented for purposes of illustration. It is contemplated that the biomarker panel is compatible with a number of amplification and sequencing schemes and the scope of the claims should not be limited to the description of the embodiments contained herein.

Probes or primers for use in the biomarker panels described herein may be fused to a tag or label. Suitable tags and labels are known in the art, including but not limited to fluorescent labels (e.g., GFP, RFP, etc.), biotin, and combinations thereof. In some embodiments, the probe or primer is biotinylated and the biotinylated probe or primer bound sequence can be purified or captured with a streptavidin bound substrate.

In some embodiments, the primers or probes are covalently or non-covalently linked to a substrate. Suitable substrates for the biomarker panel include a bead, a plate, a microfluidic devise, a cuvette, a chip, a multiwell plate (e.g., 6-, 12-, 24-, 48-, 96-, 384-, or 1536-well plates).

In some embodiments, the biomarker panel is a microarray.

In some embodiments, the primers or probes are biotinylated and bind to streptavidin coated substrates for selection of the DMRs or DMR-associated genes targeted by the probe or primers. In some embodiments, the streptavidin-coated substrates are beads.

Methods

In some aspects, described herein are methods to assay the methylation status of DMRs or DMR-associated genes described herein to diagnose or give a prognosis for AT or trait-like anxiety in an individual. Methylation levels of at least one DMR or DMR-associated gene recited in Table 2, or any combination of DMRs or DMR-associated genes, is measured in target DNA from a blood sample or saliva sample from a human or non-human primate.

Methylation may be quantified by any suitable means known in the art. Suitable methods for assaying quantification are disclosed, for example, by Kurdyukov and Bullock ("DNA methylation analysis: Choosing the right method," Biology, 2016, 5(3)). Suitable methods for quantifying or assaying methylation may include, but are not limited to methylation specific polymerase chain reaction (PCR), high resolution melting, cold-PCR, pyrosequencing, PCR and sequencing, bead array, and digestion-based assay followed by PCR or quantitative PCR (qPCR).

In some embodiments, the target DNA is bisulfite modified. Bisulfite treatment mediates the deamination of cytosine to uracil, whereby the modified uracil residue will be read as a thymine as determined by PCR-amplification and sequencing. 5mC resides are protected from this conversion and will remain as cytosine.

To examine the methylation status of the DMR or DMR-associated gene, target genomic DNA may be isolated from a blood sample or a saliva sample from a subject. In some embodiments, the target DNA is isolated from a blood sample from a human or non-human primate. In some embodiments, the target DNA is isolated from a saliva sample from a human or non-human primate.

Following isolation of target DNA, the target DNA will be contacted with probes specific to the DMRs outlined in Table 2 to isolate and enrich these genomic regions from the target DNA sample. In some embodiments, sequences of the DMR is used as bait to isolate the genomic regions of interest for amplification and sequencing.

After isolation and enrichment of the genomic regions within the target DNA that include the DMR, methylated adapters are ligated to the enriched regions. The sample with the ligated methylated adapters may then be subject to sodium bisulfite modification.

In general, target DNA or bisulfite modified target DNA is subject to amplification. The amplification may be polymerase chain reaction (PCR) amplification. PCR amplification will include single or multiple pair(s) of primers and probes at specific DMRs within the DIP2C, GRB10, INPP5A, C17ORF97, PDXK, CACNA2D4, TRAPPC9, CRTC1, MEGF6, HIVEP3, OPCML, PITPNM2, ZFPM1, RAP1GAP2, NFATC1, RNF126, FSTL3, GNAS, SH3BP2, NEURL1B, MAD1L1, HSPA12B, IGF2, PEG10, PEG5, SLC16A3, SYTL1, and ZIM2 genes as outlined in Table 2. The target DNA amplification and methylation quantification will be evaluated in one or multiple tubes.

In some embodiments, methylation is quantified by amplification and sequencing of target DNA. Bisulfite modified target DNA may be subject to PCR to amplify target regions outlined in Table 2. The PCR reaction mixture typically includes at least one pair of primers designed to target a DMR detailed in Table 2, PCR buffer, dNTPs (e.g., adenine, thymine, cytosine and guanine), $MgCl_2$, and polymerase. PCR amplification generally includes the steps of heating the reaction mixture to separate the strands of the target DNA, annealing the primers to the target DNA by cooling the reaction mixture, allowing the polymerase to extend the primers by addition of NTPs, and repeating the process at least 2, at least 5, at least 10, at least 15, at least 20, at least 25, or at least 30 times to produce a PCR amplification product. If the target DNA in the reaction mixture is single stranded, the initial heating step may be omitted, however this heating step will need to be included when the second and subsequent times the reaction is completed to separate the extended primer strands from the opposite strand and DNA (e.g., the target DNA or another previously extended primer strand). In some embodiments, the target DNA is bisulfite modified prior to amplification.

In some embodiments, the bisulfite modified target DNA is used in a methylation-specific-quantitative PCR (MS-QPCR) reaction such as MethylLight (WO 2000/070090A1) or HeavyMethyl (WO 2002/072880A2). For example, a reaction mixture for use in a MethylLight methylation specific PCR reaction would contain primers and probes specific to the DMRs recited in Table 2, PCR buffer, dNTPs (e.g., adenine, thymine, cytosine and guanine), $MgCl_2$, and polymerase. A typical kit for methylation specific PCR may include primers and probes specific to the DMRs recited in Table 2, wild type reference gene primers such as (3-actin, PCR buffer, dNTPs, $MgCl_2$, polymerase, positive and negative methylation controls, and a dilution reference. The MS-QPCR may be carried out in one or multiple reaction tubes.

In some embodiments, either the forward or reverse primer of the primer pair used in the PCR amplification reaction is biotinylated. When a biotinylated primer is used in a PCR amplification reaction, PCR products may be purified, captured, and/or sorted with a streptavidin coated substrate. In some embodiments, the substrate is a streptavidin coated bead. In some embodiments, the beads are streptavidin sepharose beads. In some embodiments, the beads are magnetic.

In some embodiments, the PCR amplification product is contacted with one or more probes specific for and complementary to a DMR detailed in Table 2. The probe may be biotinylated. The PCR amplification product and probe mixture can then be purified, captured and/or sorted with a streptavidin-coated substrate. In some embodiments, the substrate is a streptavidin-coated bead. In some embodiments, the beads are streptavidin sepharose beads. In some embodiments, the streptavidin beads are magnetic.

In some embodiments, methylation is quantified using pyrosequencing. Bisulfite modified target DNA may be subject to PCR to amplify target regions outlined in Table 2 as described above. PCR amplification products are purified, denatured to single-stranded DNA, and annealed to a sequencing primer for methylation quantification by pyrosequencing as the DMR or DMR-associated gene as detailed in Table 2. In some embodiments, methylation may be quantified with PyroMark™MD Pyrosequencing System (Qiagen) using PyroPyroMark® Gold Q96 Reagents (Qiagen, Cat #972804) (QIAGEN PyroMark Gold Q96 Reagents Handbook August 2009, 36-38).

In some embodiments, bisulfite treated DNA is subject to an Invader® assay to detect changes in methylation. The Invader® assay entails the use of Invader® chemistry (Hologic Inc.; invaderchemistry.com; Day, S., and Mast, A. Invader assay, 2004; Chapter in Encyclopedia of Diagnostic Genomics and Proteomics. Marcel Dekker, Inc., U.S. Pat. Nos. 7,011,944; 6,913,881; 6,875,572 and 6,872,816). In the Invader® assay, one would use a structure-specific flap endonuclease (FEN) to cleave a three-dimensional complex formed by hybridization of C/T specific overlapping oligonucleotides to target DNA containing a CG site. Initial PCR amplification of the bisulfite treated target DNA may be necessary if the quantity of the bisulfite treated target DNA is less than 20 ng.

The present invention has been described in terms of one or more preferred embodiments, and it should be appreciated that many equivalents, alternatives, variations, and modifications, aside from those expressly stated, are possible and within the scope of the invention.

Example 1

To investigate the role of DNA methylation in the development and expression of AT, we previously performed genome-wide DNA methylation and mRNA expression analyses in Ce tissue collected from young monkeys repeatedly phenotyped for AT and its associated brain metabolism. This approach identified twenty-two genes with a significant correlation between AT-associated methylation levels and gene expression (P-value <0.05), including two glutamate receptors, GRIN1 and GRM5, both of which have reported roles in fear and anxiety-like behaviors. These findings are also likely to provide insights into novel treatment targets for individuals that have already developed clinically significant anxiety and depressive disorders.

The monozygotic (MZ) twin difference design is an ideal way to probe non-shared environmentally or experientially based relationships between HPA activity and amygdala function. MZ co-twins are identical for DNA sequence variants with the exception of rare somatic mutations. MZ twins reared together also share many non-genetic factors (e.g., age, parenting, etc.); thus, reliable MZ twin differences are attributed to unique or non-shared environmental factors. In this context, "environmental" simply means "non-genetic" and "unique" means "not shared with the co-twin." Twin studies have shown that afternoon cortisol levels and amygdala volume are strongly influenced by environmental (i.e., non-genetic) factors. In addition, a substantial portion of the individual variability in anxiety level is due to variations in non-genetic factors. We recently used this design to examine the role of DNA methylation in the development and expression of human clinical anxiety using a multi-dimensional characterization method, to select monozygotic twin pairs discordant for anxiety, and whole genome DNA methylation sequencing. Profiling the whole blood DNA methylation levels in discordant individuals revealed 230 anxiety-related differentially methylated loci that were annotated to 183 genes, including several known stress-related genes such as NAV1, IGF2, GNAS, and CRTCJ. As an initial validation of these findings, we tested the significance of an overlap of these data with anxiety-related differentially methylated loci in the Ce of young monkeys and found a significant overlap (P-value <0.05) of anxiety-related differentially methylated genes, including GNAS, SYN3, and JAG2. Together, these data demonstrate environmentally sensitive factors that may underlie the development of human anxiety and suggested that biomarkers of human anxiety can be detected in human blood.

Here we built upon these findings and used whole genome bisulfite sequencing to examine an average of 25.3 million CpG dinucleotides in genomic DNA from the hippocampal and blood tissue of 71 monkeys (including 23 females) and found significant overlaps of DMRs in these tissues, as well as with the previously reported anxiety-related DMRs in the monkey Ce and human blood. Together, these data suggest that blood can be used as a viable surrogate to brain tissue toward the development of a blood-based biomarker profile for clinical anxiety diagnosis, to improve estimates of clinical anxiety prognosis, and to guide personalized treatment of clinical anxiety.

Materials and Methods

Tissue Acquisition and DNA/RNA Extraction—

The whole brains from seventy-one young monkeys (including 23 females) with an average age of 1.3±0.2 years and a broad range of AT levels (−1.48 to 1.43) were sectioned into 4.5 mm slabs and functionally guided tissue biopsies of the hippocampus were conducted following animal housing and experimental procedures that are in accordance with institutional guidelines (UW IACUC protocol #G00181). Hippocampal regions were identified, thawed briefly on wet ice, and placed on an inverted glass Petri dish on top of wet ice. A circular 3-mm punch tool was used to biopsy the region best corresponding to the hippocampus. The tissue punches were collected into 1.5-mL microfuge tubes and placed on dry ice. Once acquired, approximately thirty milligrams of tissue were homogenized with glass beads (Sigma) and DNA and RNA extraction was performed using AllPrep DNA/RNA mini kit (Qiagen).

Whole blood was collected from the same seventy-one young monkeys in a BD vacutainer CPT cell preparation tube with sodium heparin (cat #362753). The peripheral blood mononuclear cells were isolated and genomic DNA was extracted using Promega wizard genomic DNA purification kit (cat #A1120), following the manufacturers protocol.

Library Preparation and high-throughput sequencing of genomic DNA—

To elucidate the utility of blood DNA methylation as a potential biomarker of anxiety and depressive disorders we will perform whole genome sequencing with bisulfite pretreatment. This unbiased approach uses bisulfite exposure and deamination chemistry to convert unmethylated cytosines to uracil, while leaving methylated cytosines unmodified. Subsequent sequencing of the treated DNAs provides single base-pair resolution of all methylated sites in the rhesus genome, and will expose novel genes and alleles of interest if present. To achieve this goal, extracted genomic DNA was resolved on a 1% agarose gel to verify that the DNA is of high molecular weight, and quantified using Qubit (Qiagen™, Hilden, Germany). Genome-wide methylation data was generated at WuXi NextCode (Cambridge, Mass.) using whole genome HiSeq technologies from Illumina™ (e.g., HiSeq X ten). High quality genomic DNAs were forwarded to WuXi NextCode™ for sodium bisulfite treatment, library preparation, and whole genome sequencing. To process the samples, genomic DNA (500 ng) was randomly fragmented, end-repaired, and ligated to NEBNext Methylated Adapters for Illumina sequencing following the manufacturer's protocol (Illumina™) Adapter-ligated DNA fragments, ranging from 200 to 400 base pairs (bp), are purified by Sample Purification Beads (Illumina™) and then treated with sodium bisulfite (ZymoResearch™ EZ DNA methylation gold kit), that converts unmethylated cytosines to uracil and leaves methylated cytosines unaltered. Libraries of converted DNA fragments are then amplified using KAPA HiFi Hot Start Uracil+Ready Mix (KAPA Biosystems™ KM2801), and Index Primer for Illumina and Universal PCR Primer for Illumina (NEB™ E7336A). Amplicons are purified by Sample Purification Beads (Illumina™) and sequenced on a Next-Generation sequencer (Illumina™ HiSeq X ten). This approach yields ~3 billion 150 bp-reads for each library, which provides the methylation status of ~25 million positions in the DNA where a cytosine nucleotide is followed by a guanine nucleotide in the linear sequence of bases along its 5' →3' direction (i.e., CpG sites) with a coverage >10 reads. Image processing and sequence extraction use the standard Illumina Pipeline. Raw fastq sequence files will be forwarded to our laboratory via FedEx on an encrypted external hard drive.

DNA Methylation Detection—

Quality control, mapping, and extraction of methylation information from the whole genome sequence data was done using bowtie2 and bismark (version 0.17.0). The average number of raw reads for each sample (N=142) was 404 million reads giving an average genomic coverage of 20.23× (median genomic coverage 19.53×). The sequence data will be filtered, and low quality and adapter sequences will be removed thereby arriving at an average genomic coverage of ~20×. Cleaned sequence data are then mapped to the human *Macaca mulatta* (Rhesus monkey) reference genome (rheMac8), and an average of 283.3 million uniquely mapped reads were obtained for each sample, giving an average coverage of 14.16× (median coverage 13.86×). Sequence reads from both DNA strands (forward and reverse) were combined to determine the DNA methylation level at all CpG dinucleotides (~27.4 million). Differentially methylated regions (DMRs) were identified using the DSS-single analysis method, which was selected because it incorporates the read depth into the DMR analysis and relies on smoothing so that neighborhood CpGs can be viewed as pseudo replicates and dispersion can be estimated across an entire genomic window. AT status was treated as a continuous independent variable, while methylation level was the dependent variable. All default settings were used in the DSS package (including a smoothing span of 500 bp) and the model was adjusted for gender and age. DMRs were identified using a generalized linear model in DSS, and limiting DMRs to those having a minimum of 5 consecutive CpG dinucleotides with a difference in mean methylation of 10% between the tested variables.

RNA Library Preparation and Sequencing—

One hundred nanograms of total RNA from hippcampal tissue was used for sequence library construction following instructions of the NuGen mRNA sample prep kit (cat #0348). In brief, total RNA was copied into first strand cDNA using reverse transcriptase and random primers. This process was followed by second strand cDNA synthesis using DNA Polymerase I and RNaseH. The cDNA fragments were end repaired, a single "A" base was added, and then ligated to adapters. The products were gel purified and enriched by PCR to generate cDNA libraries. One hundred-cycle single-end sequencing was performed by Novogene Corporation (Sacramento, Calif. USA).

RNA-Seq Processing and Analysis—

After adapter trimming of reads, a median of 20.2 million paired-end reads were obtained per sample. Quality was assessed for each pair-mate using FastQC. After reads were assured for quality, paired-end reads were aligned to the Rhesus *Macaca mulatta* reference genome (Mmul_8.0.1) using RSEMv1.3.1, which utilized STAR v2.7.0. RNA transcription was quantified using RSEM which resulted in quantification for ~30,000 ensembl genes. Genes were filtered out if the total count for the gene was less than 500, or if it was present in less than 25 of the 31 samples. This resulted in a total of 12,768 ensembl genes, corresponding to a total of 11,471 gene symbols. The samples were classified as 'high' or 'low' anxiety depending on their AT_ToD score. If the score was below 0, the sample was classified as low, and if it was above 0, it was classified as high. Differential expression analysis was then performed using the DESeq function in the DESeq2 package. Any gene with a raw P-value <0.1 and a log 2 fold change >0.1 was deemed significant.

Results

The Hippocampal Methylome of Young Rhesus Monkeys—

To characterize the DNA methylation levels across the entire hippocampus genome (i.e., the hippocampal methylome) from young primates and reveal the epigenetic basis of anxious temperament, we extracted genomic DNA from the hippocampus of seventy-one rhesus macaques. All seventy-one monkeys were young (mean age=1.3±0.2 years) with a broad range of AT levels (−1.48 to 1.43). AT is computed as a composite measure among vocalizations, cortisol levels and time freezing (mean AT score) assessed during the no eye contact (NEC) condition of the human intruder paradigm. In this study, AT levels were assessed twice and the mean score for each monkey was used for analysis. The hippocampal genomic DNA from each monkey was treated with sodium bisulfite and sequenced on a Next-generation sequencer (Materials and Methods). This approach generated DNA methylation information at ~27.4 million CpG dinucleotides from the hippocampus of rhesus macaques. To investigate comparisons across the seventy-one individual monkey genomes, the high quality methylation data was filtered for CpG data that had a sequence read depth greater than 2 and less than 100 occurring in a minimum of thirty-six monkeys (N=26,497,371). This final dataset revealed a bimodal distribution of DNA methylation in monkey hippocampal tissue, with the majority (>60%) of CpGs being more than 60% methylated.

To examine whether the rhesus hippocampus harbors differential DNA methylation that is related to individual differences in AT levels, the methylation data were subjected to a differential methylation analysis that employed a statistical algorithm that incorporates sequence data read depth and does not need data from biological replicates (Materials and Methods). This analytical approach, which limited positive results to differentially methylated regions (DMRs) that have a minimum of 5 adjacent CpG dinucleotides with a minimum mean methylation difference of 10% across the seventy-one monkeys, revealed a total of 645 AT-related differentially methylated regions. AT-related increases in methylation were classified as hyper-DMRs and anxiety-related decreases in methylation were classified as hypo-DMRs. A total of 222 hyper- and 423 hypo-DMRs were identified and these loci were distributed across all the autosomes (Dataset 1), suggesting a genome-wide decrease in DNA methylation is associated with AT which is consistent with previous studies. Annotation of these DMRs to genomic structures revealed 515 genes that are enriched for neuronal ontological functions, such as synapse assembly and neuron development. Comparison of these genes to the genes previously found in the Ce revealed a significant overlap (P-value <0.05), indicating common AT-related epigenetic disruptions in these two brain structures. Importantly, a significant overlap (P-value <0.05) also was found between these differentially methylated genes from the monkey brain and anxiety-related differentially methylated genes reported in human blood, suggesting that blood may be an accessible tissue of value in the identification of differential methylation associated with the risk to develop trait-like anxiety.

The Whole Blood Methylome of Young Rhesus Monkeys—

The genomic DNA from whole blood of the same monkeys examined above was treated with sodium bisulfite and sequenced on a Next-generation sequencer (Materials and Methods). This approach generated DNA methylation information at ~27.6 million CpG dinucleotides from the blood tissue of rhesus macaques. To investigate comparisons across the seventy-one individual monkey genomes, the high quality methylation data was filtered for CpG data that had a read depth greater than 2 and less than 100 occurring in a minimum of thirty-six monkeys (N=26,973,327). This final dataset revealed a bimodal distribution of DNA methylation in monkey hippocampal tissue, with the majority (>60%) of CpGs being more than 60% methylated.

To examine whether the rhesus blood harbors differential DNA methylation that is related to individual differences in AT levels, the methylation data were subjected to the differential methylation analysis described for the hippocampal analysis (Materials and Methods). This analytical approach revealed a total of 719 AT-related differentially methylated regions (permutation P-value <0.01). AT-related increases in methylation were classified as hyper-DMRs and anxiety-related decreases in methylation were classified as hypo-DMRs. A total of 301 hyper- and 418 hypo-DMRs were identified and these loci were distributed across all the autosomes (Dataset 1), suggesting a genome-wide increase in DNA methylation is associated with AT which is consistent with previous studies. Comparison to monkey brain DMRs finds a significant overlap (N=51; P-value <0.0001), and the test statistics of these DMRs are significantly correlated, meaning these common DMRs are largely differentially methylated in the same direction (i.e., hyper-methylated or hypo-methylated; R-squared=0.701; P-value <0.0001).

Figure 2:
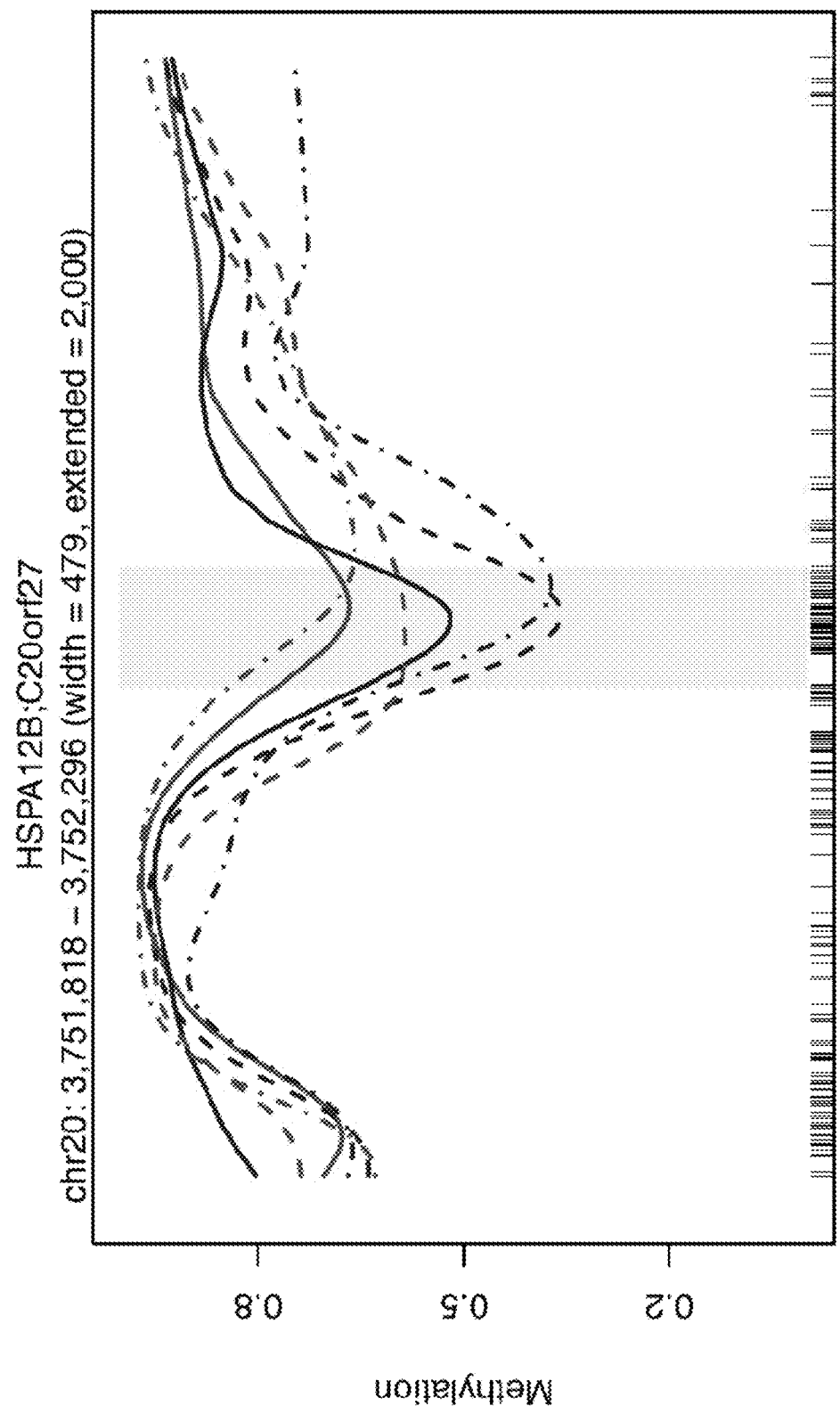
FIG. 2 shows differentially methylated region associated genes including multiple CpGs with greater than 10% differential methylation (shown as black tick marks at bottom). DNA methylation profiles for the anxious (red) and unaffected (control; blue) twin-pairs are shown and the genomic region of significance between twin-pairs is highlighted (peach). Each corresponding co-twin is indicated by a different line pattern (pair A=solid; B=dashed; C=dash+dot).
Figure 2:
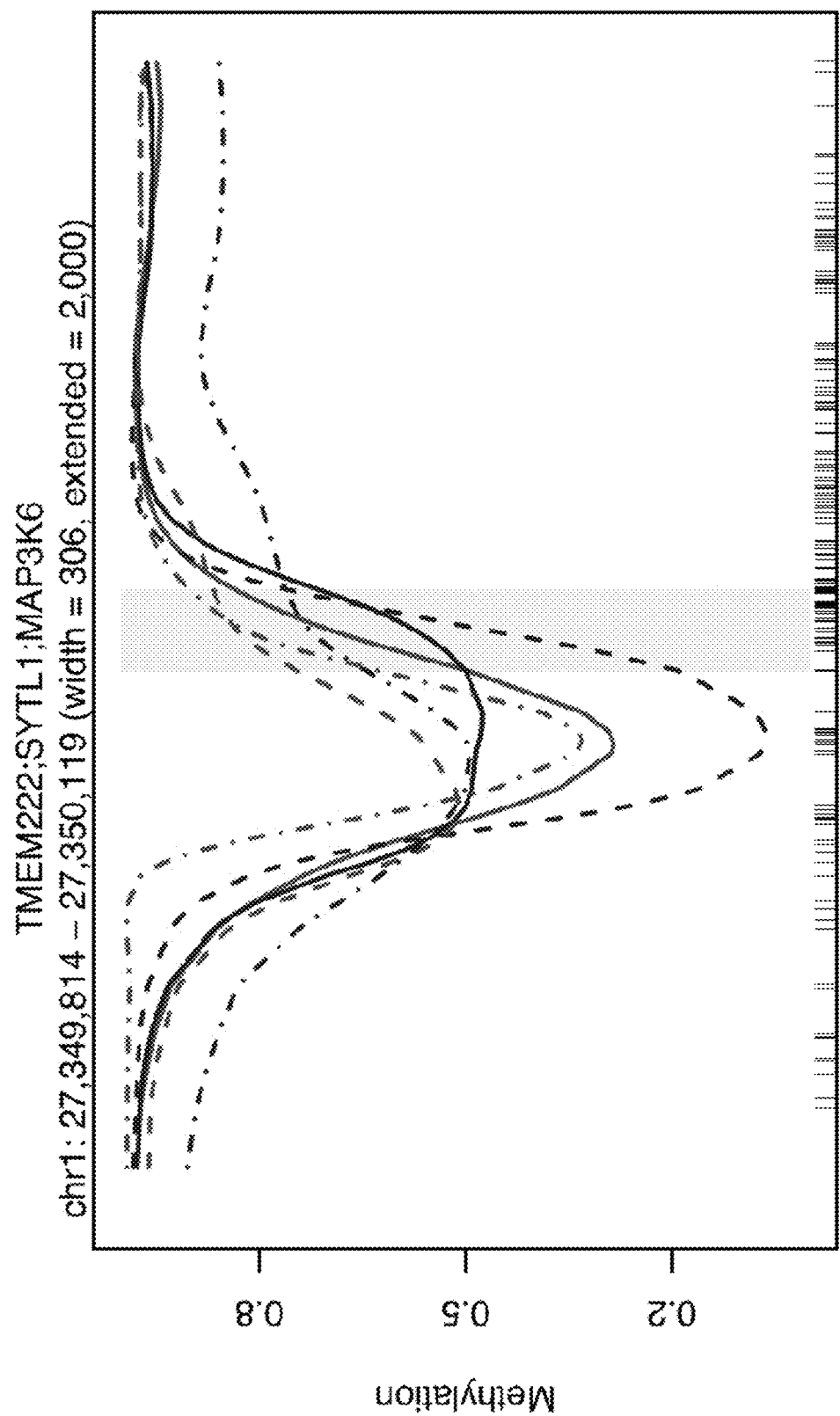
Figure 2:
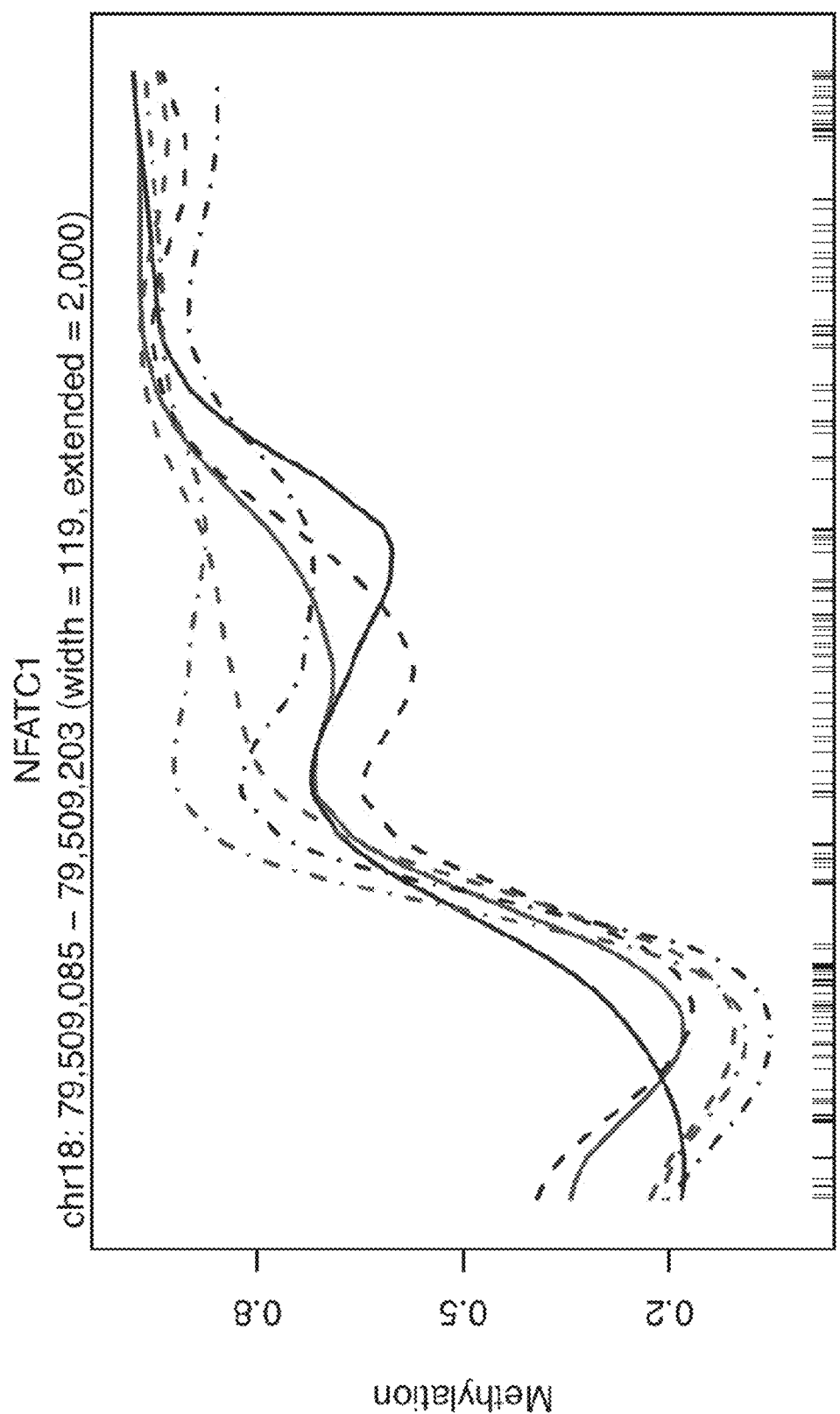
Figure 2:
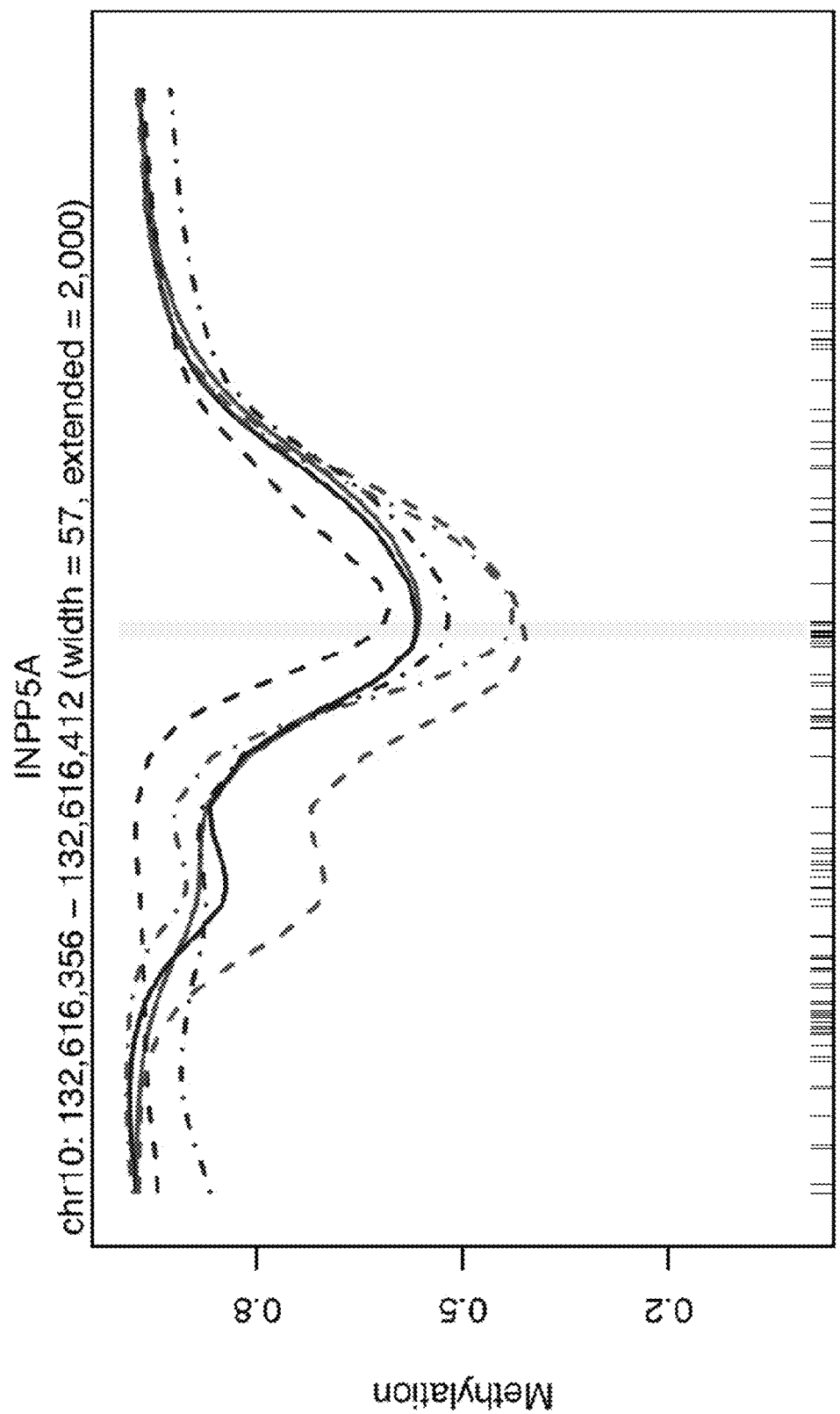
Figure 2:
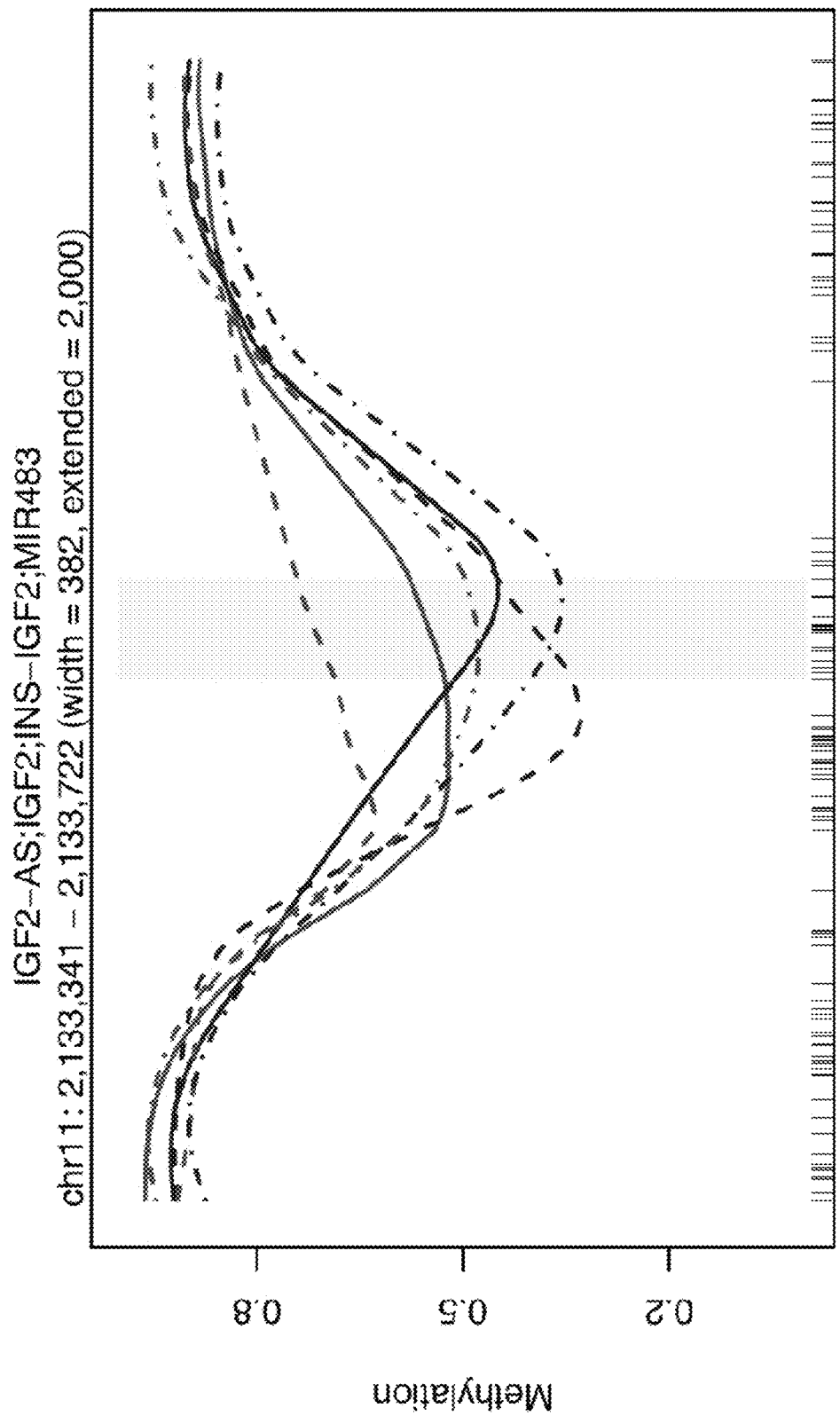
Figure 2:
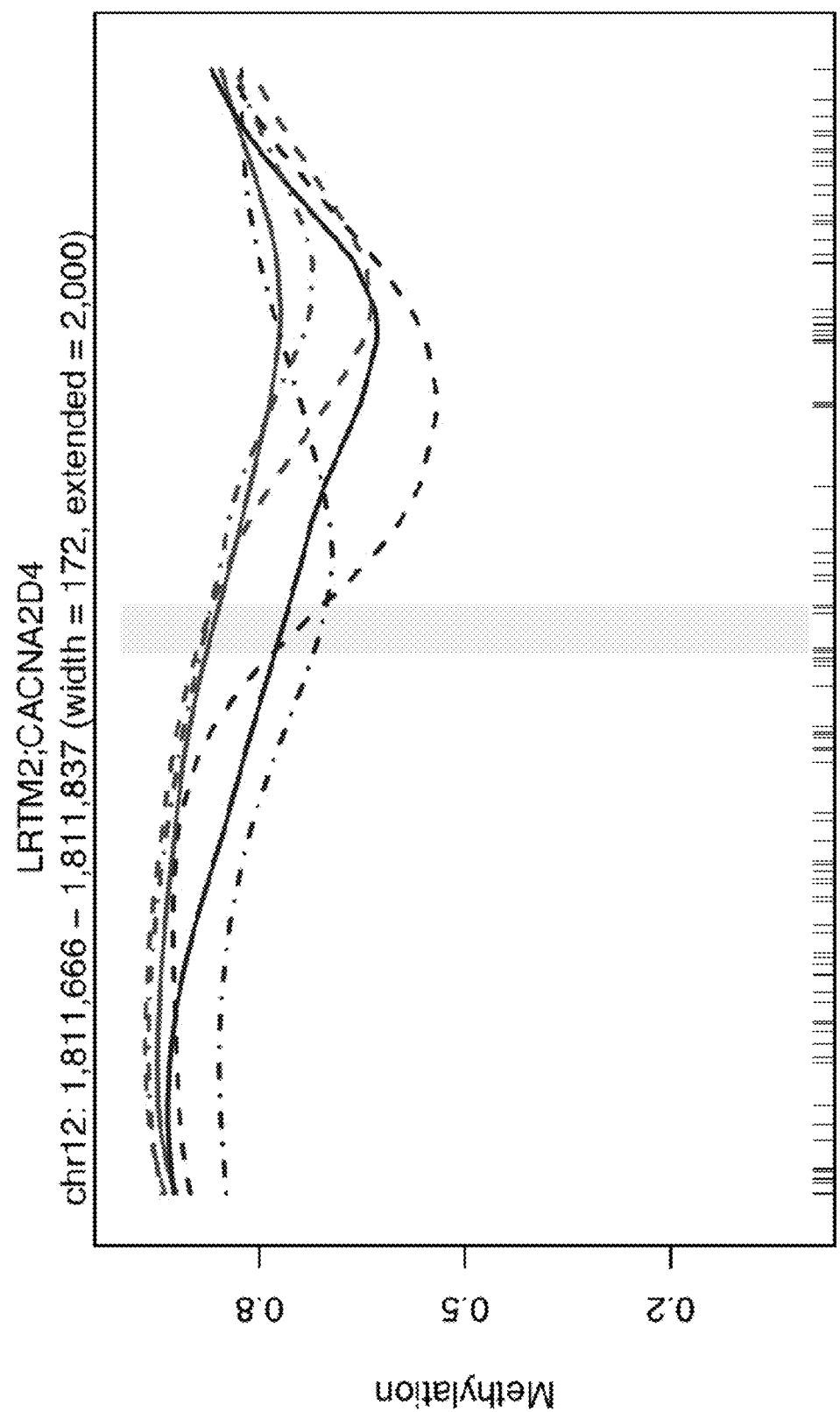
Figure 2:
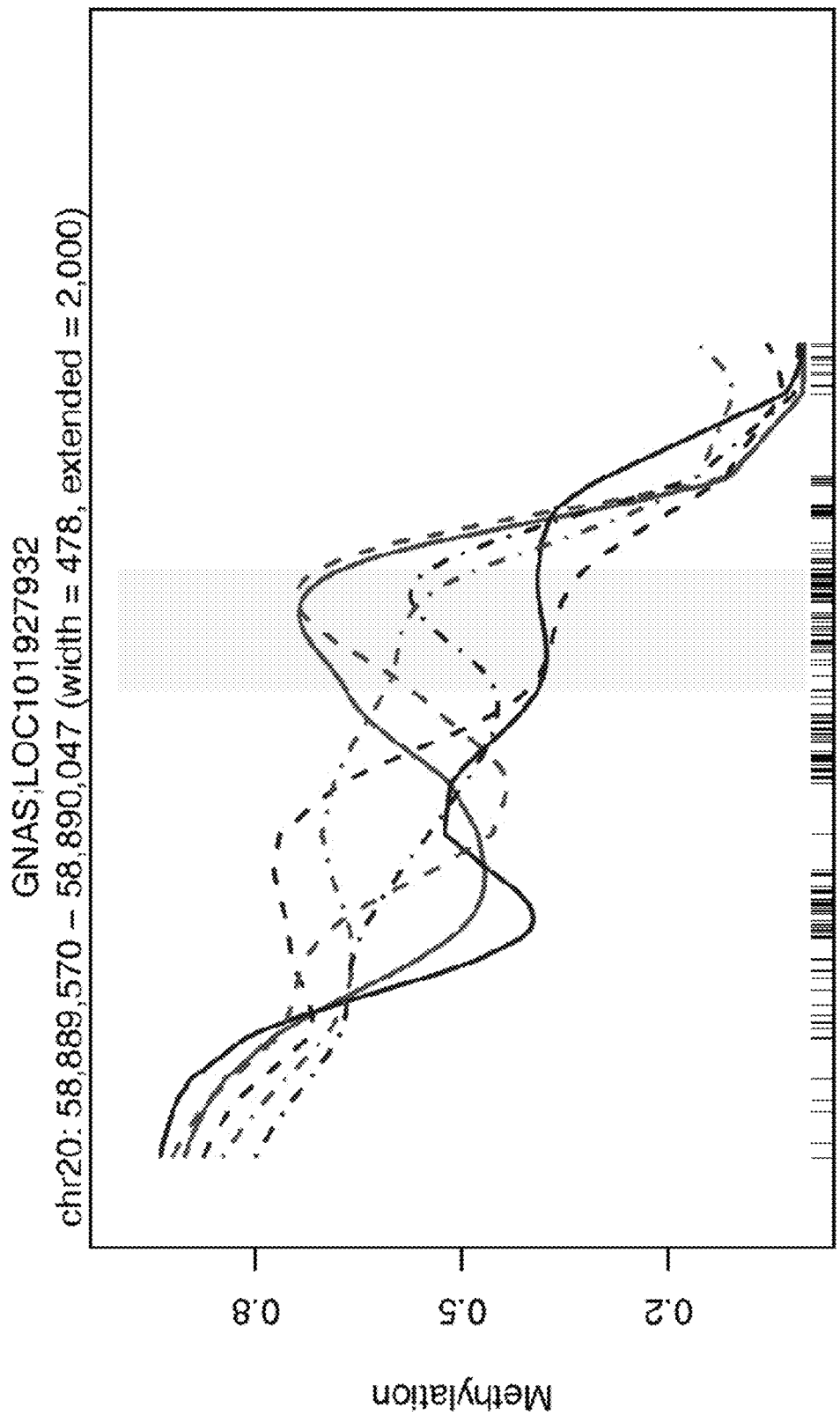
Figure 2:
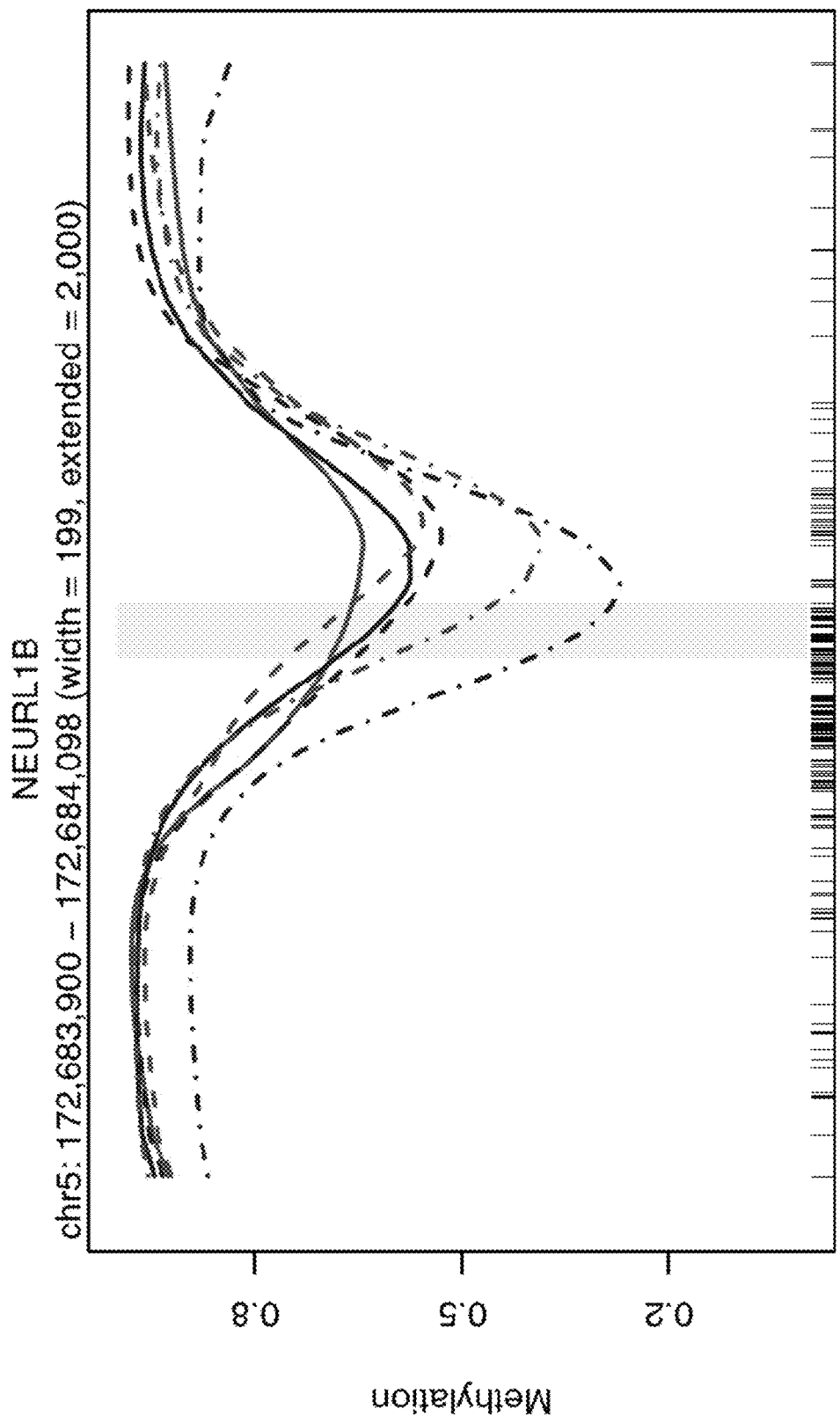
Figure 2:
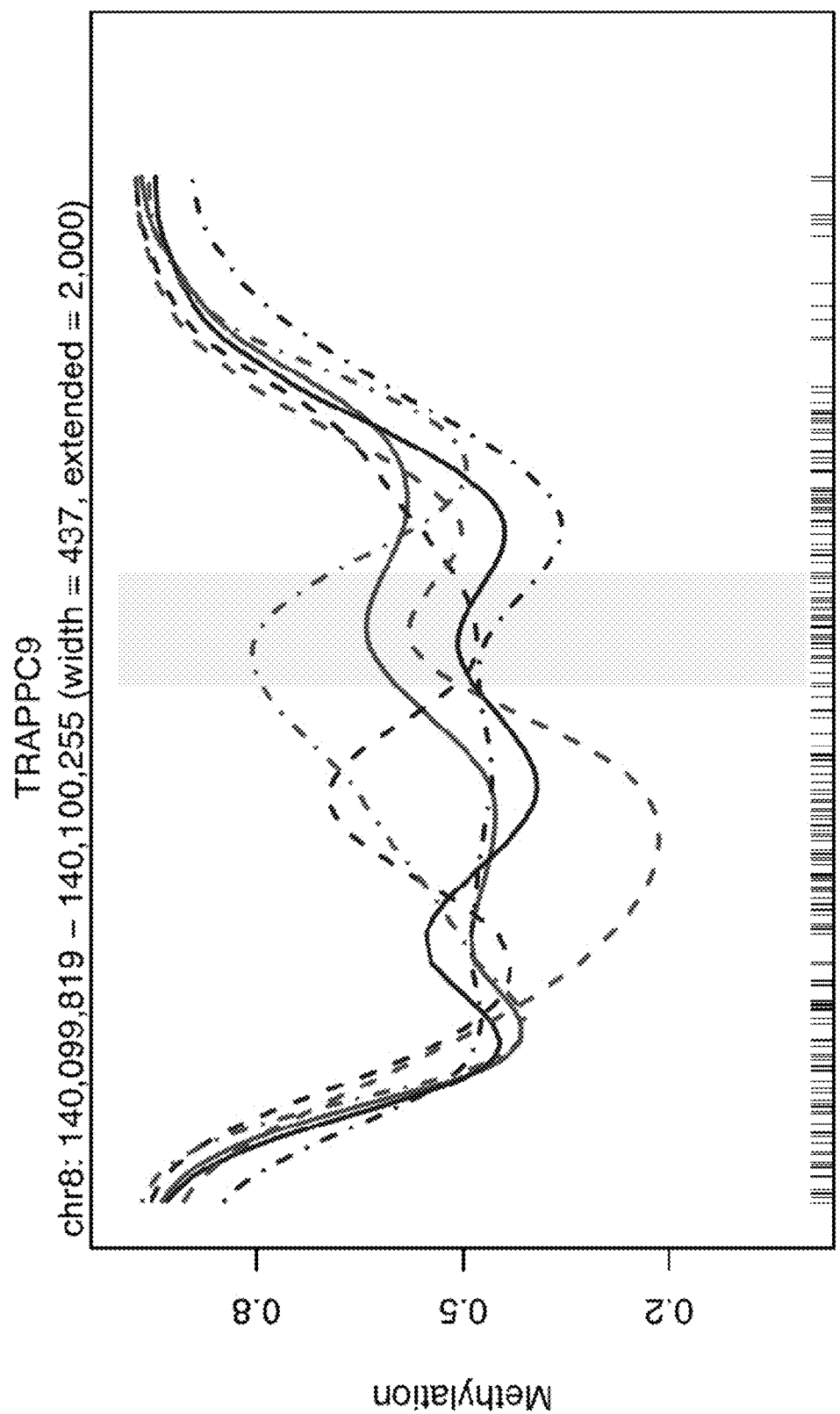
Figure 2:
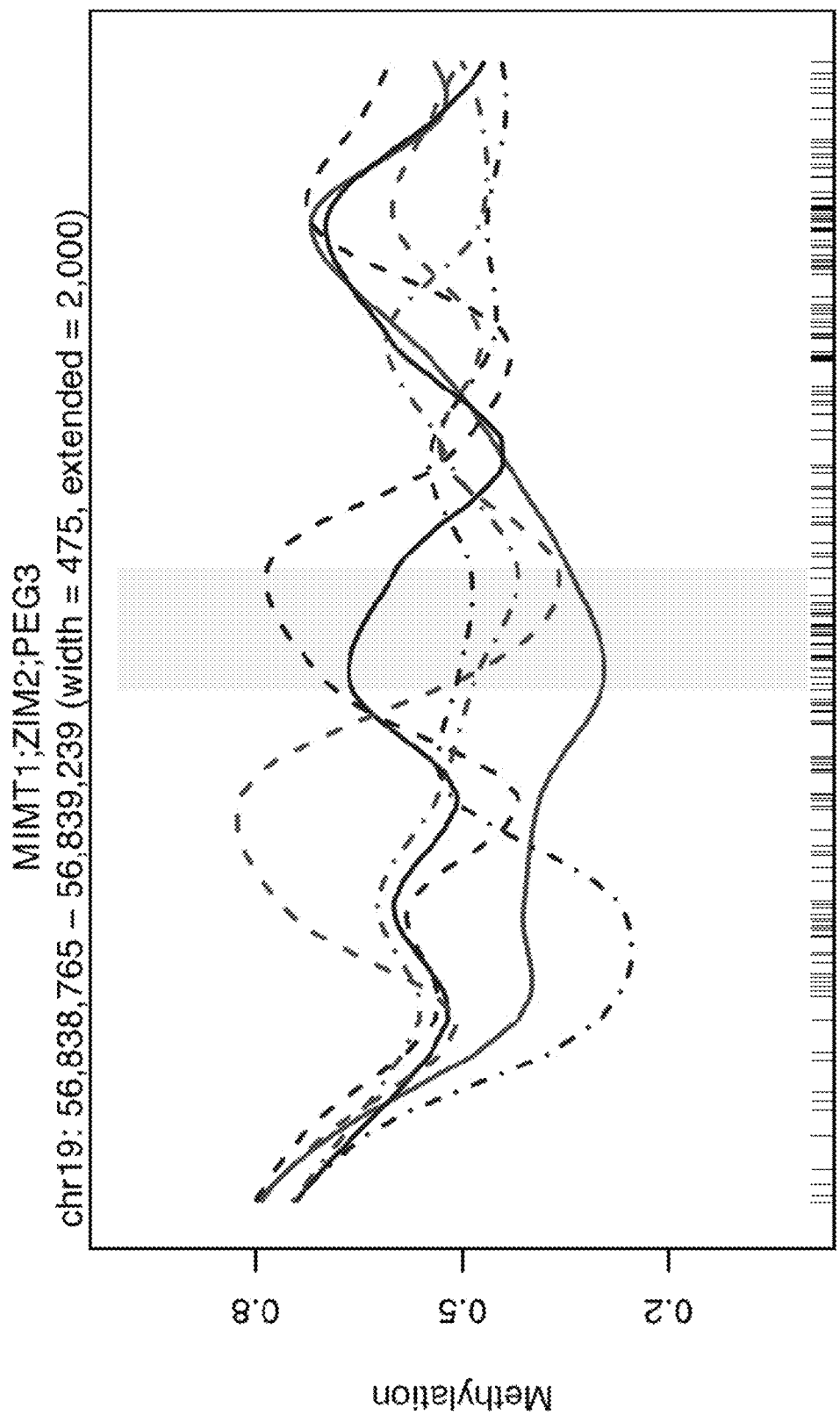
Figure 2:
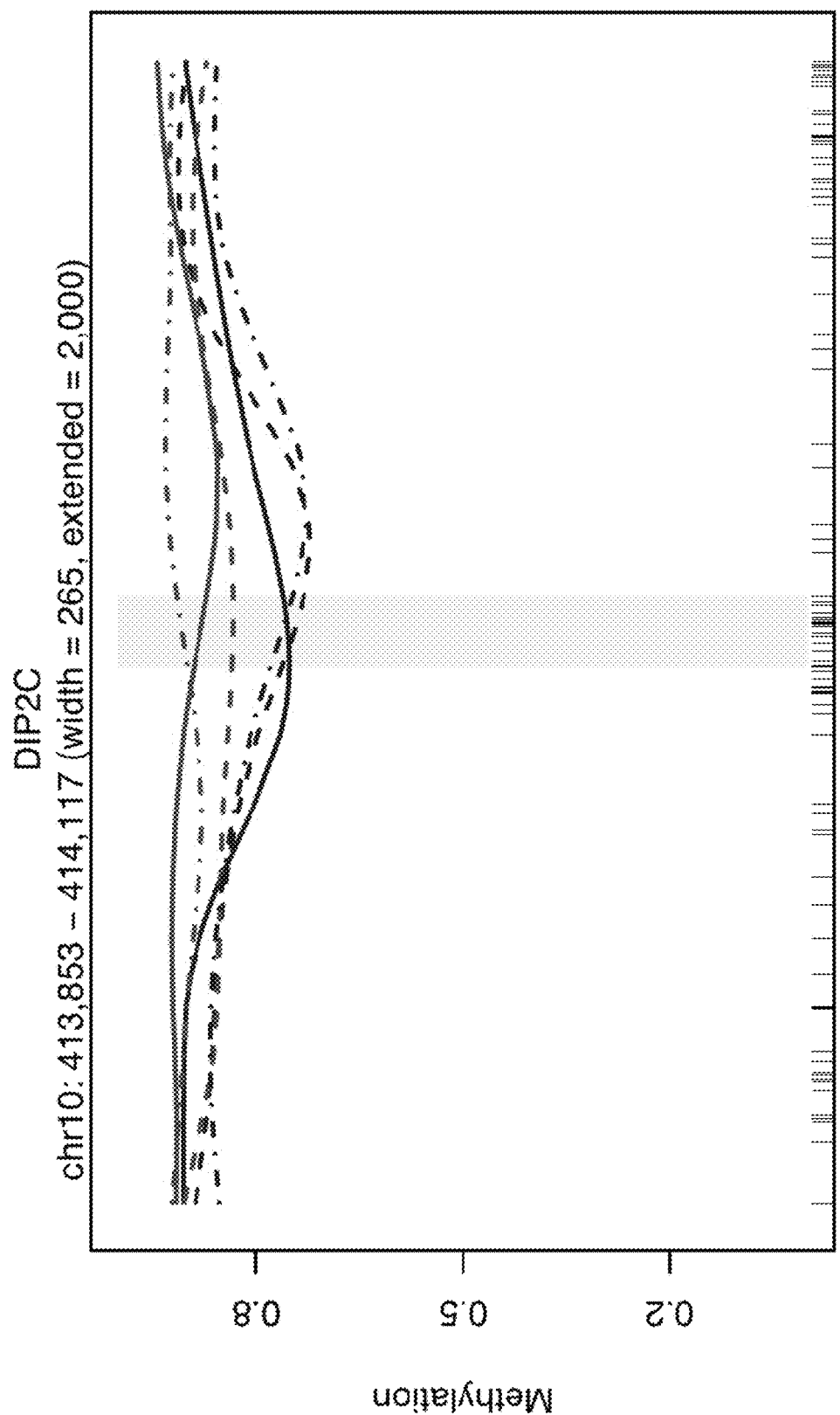
Figure 2:
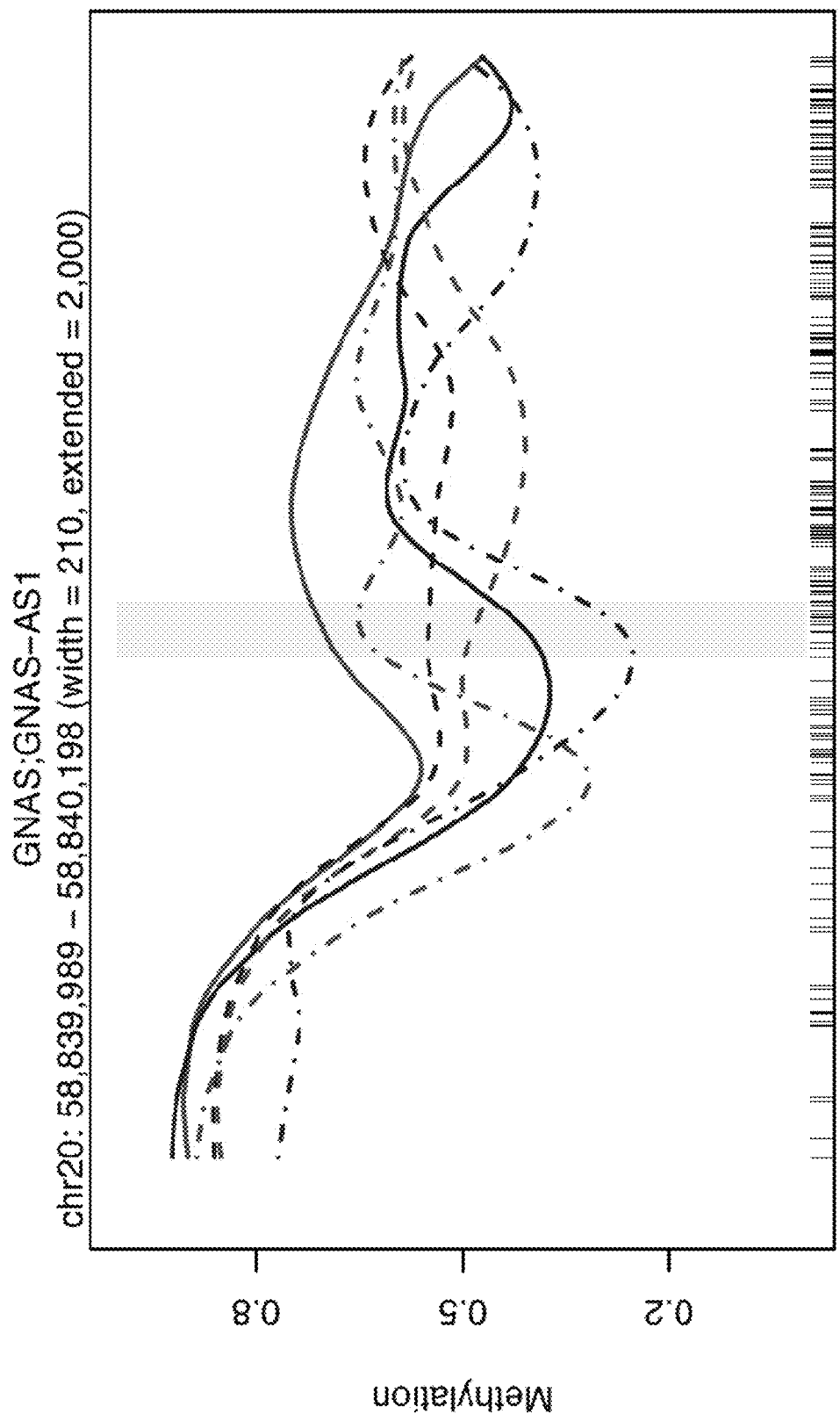
Figure 2:
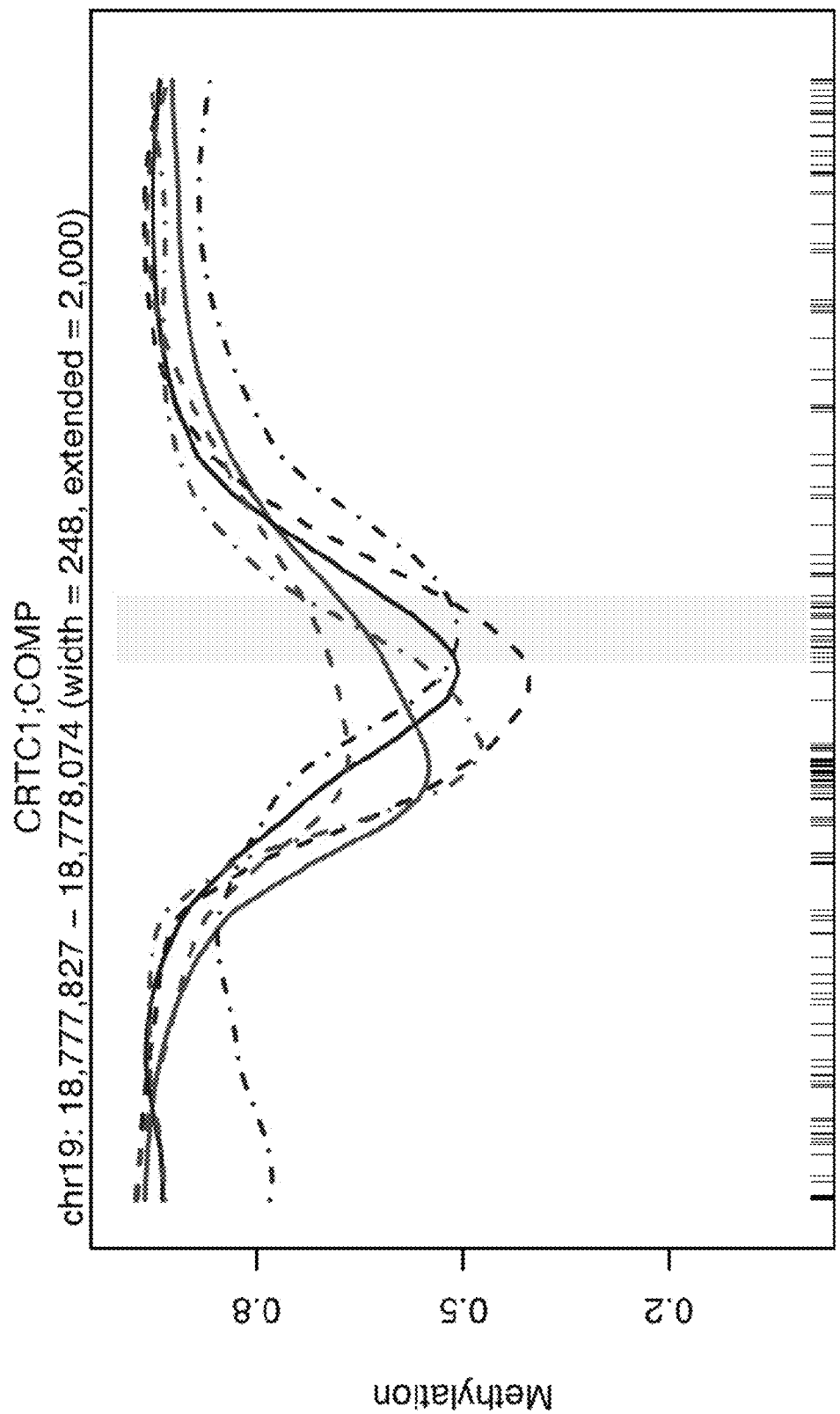
Figure 2:
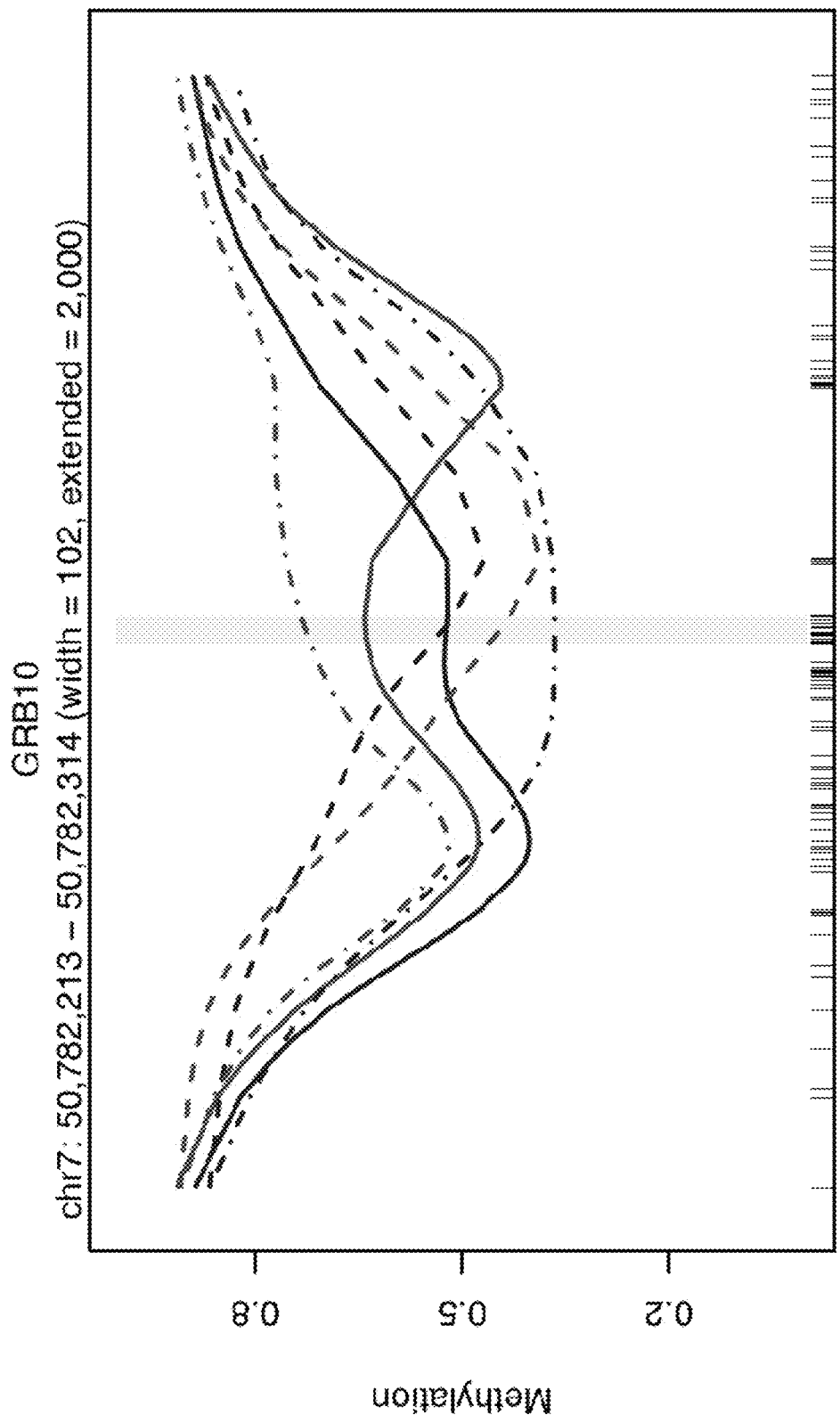
Figure 2:
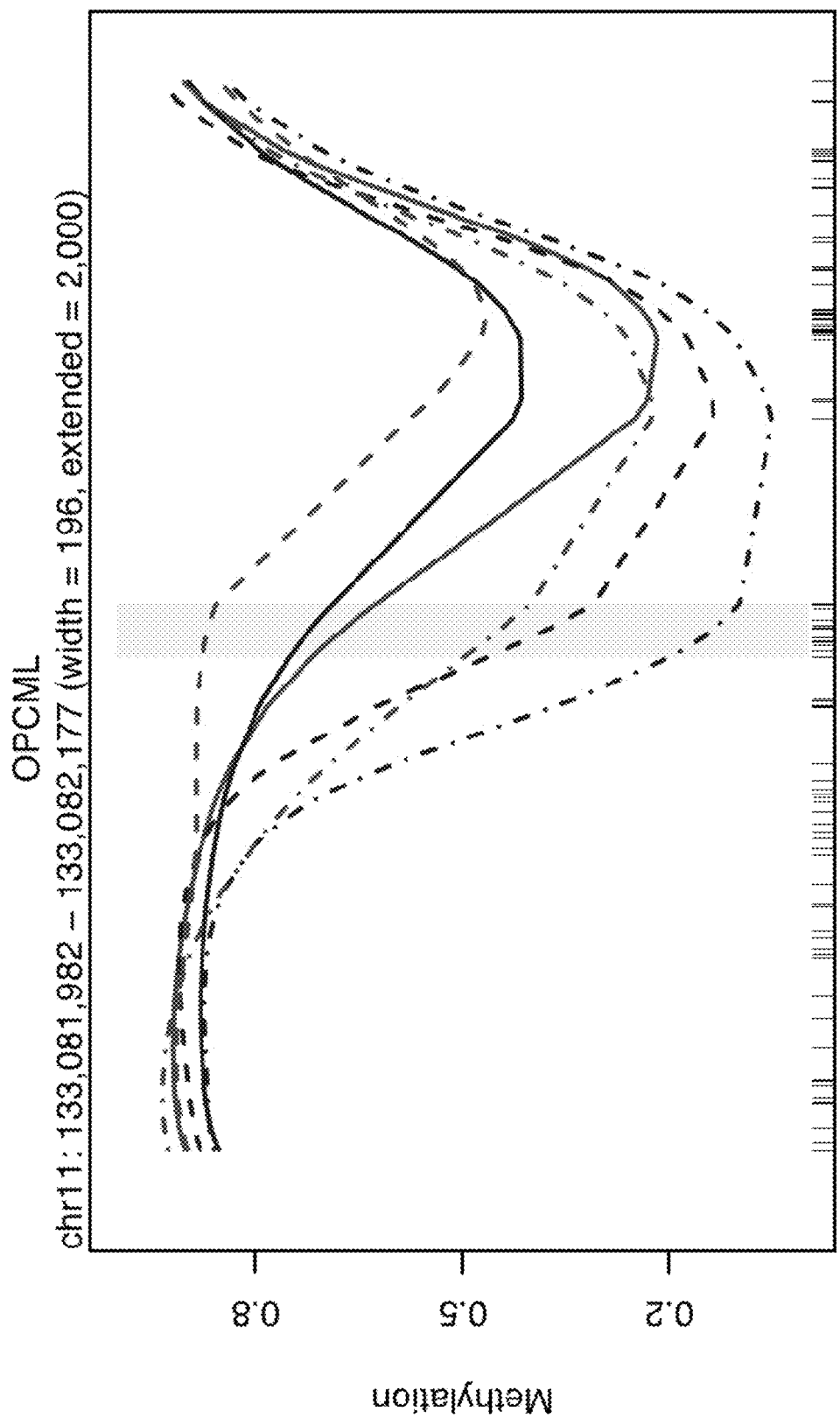
Figure 2:
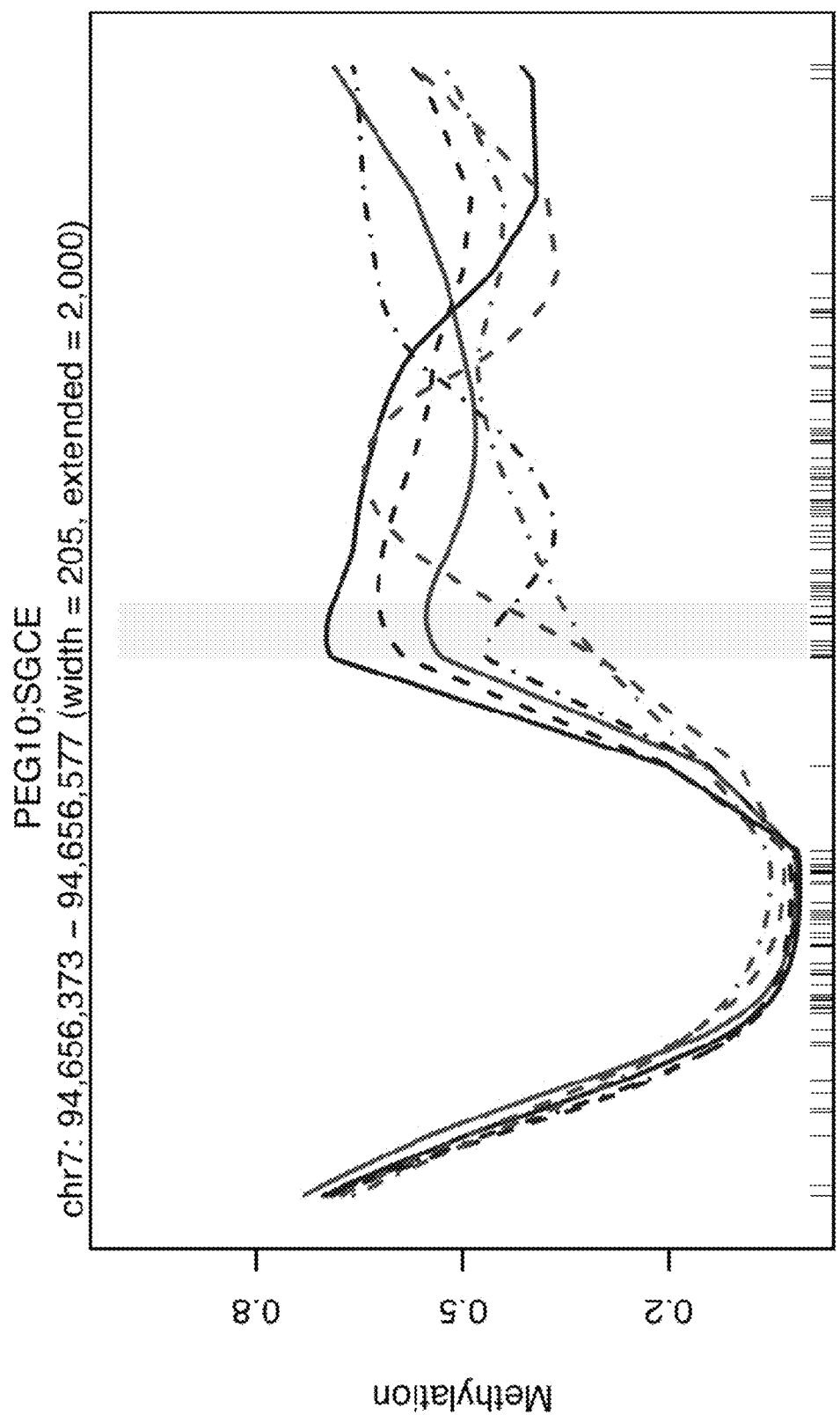
Figure 2:
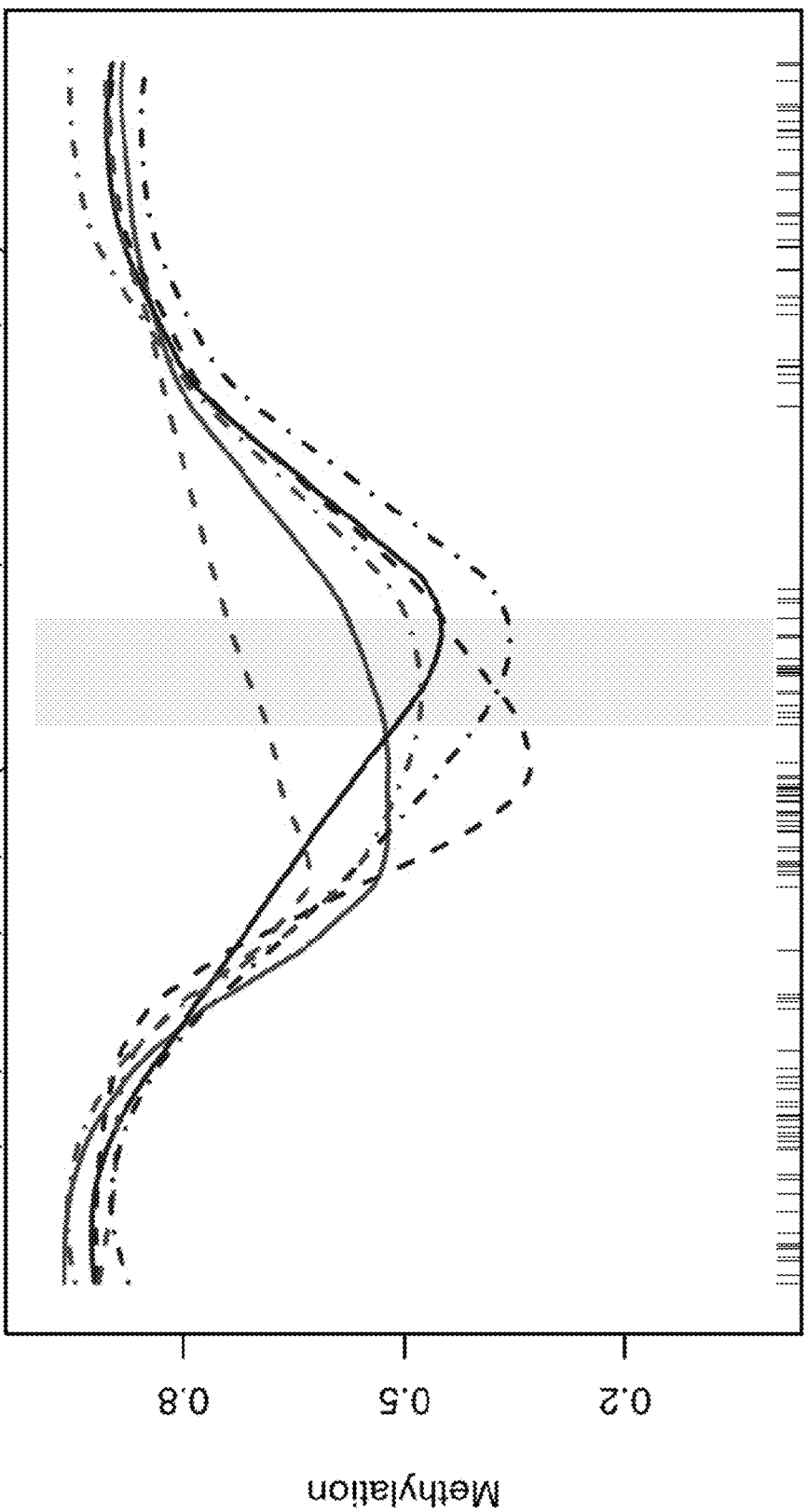
Figure 2:
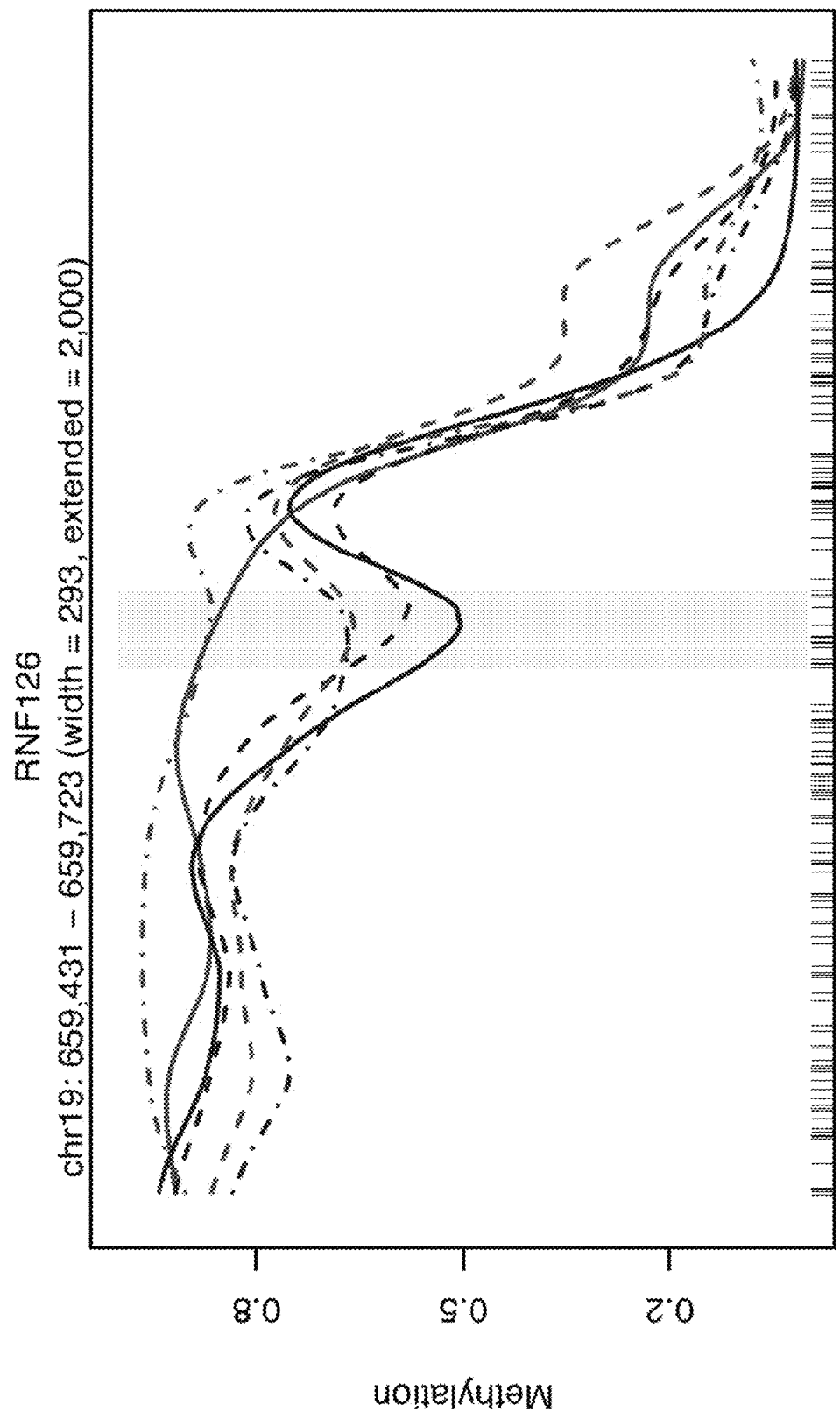
Figure 2:
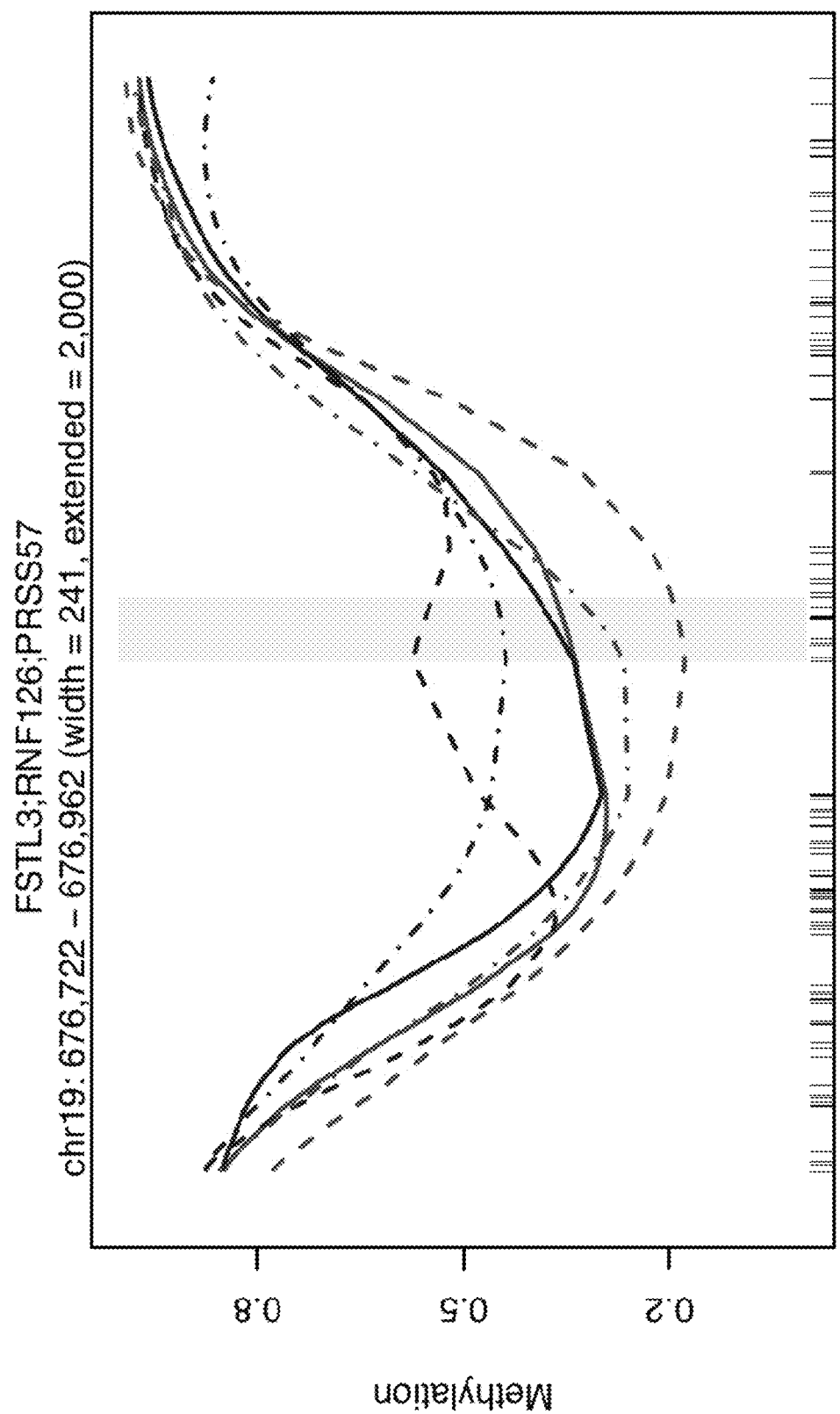
Figure 2:
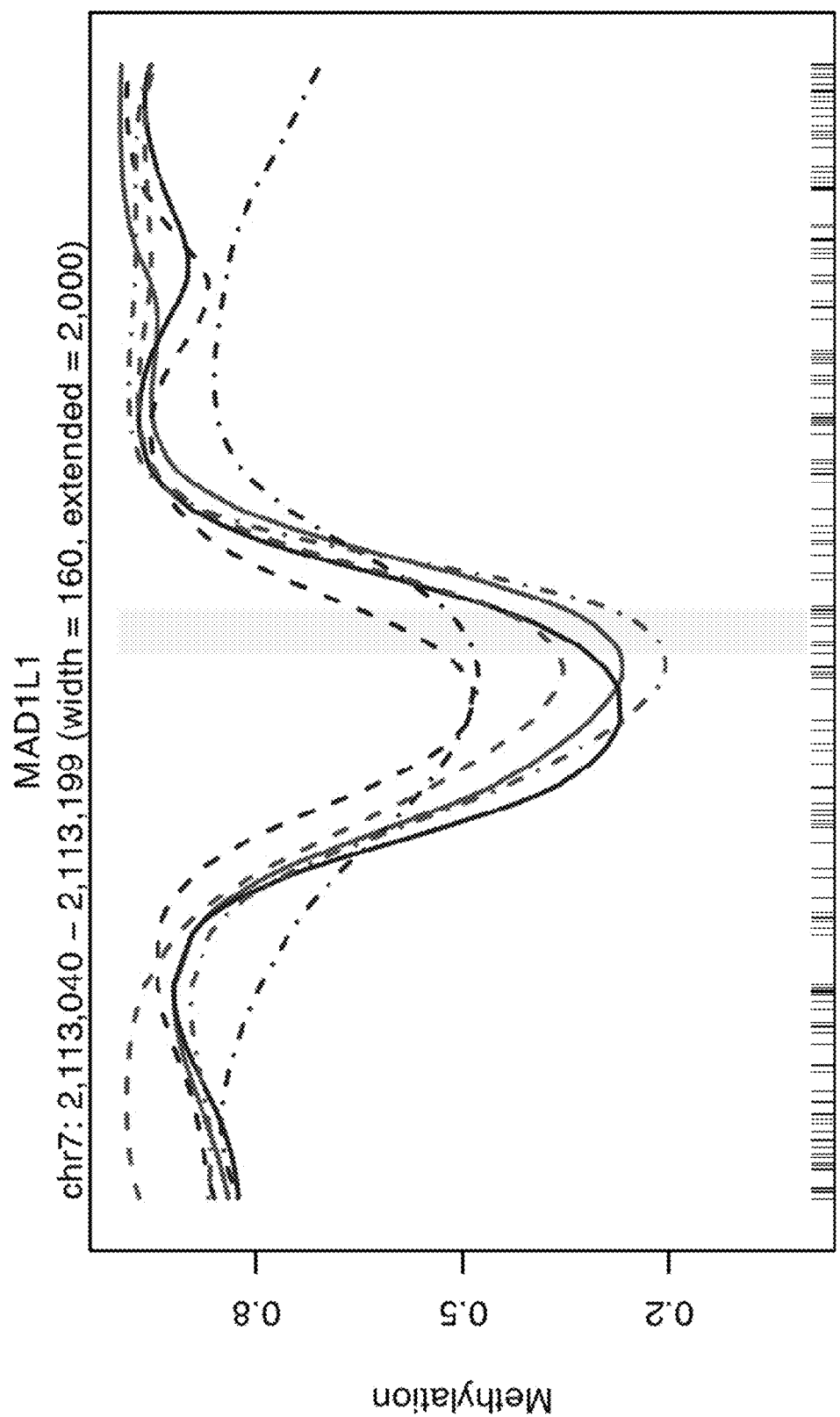
Figure 2:
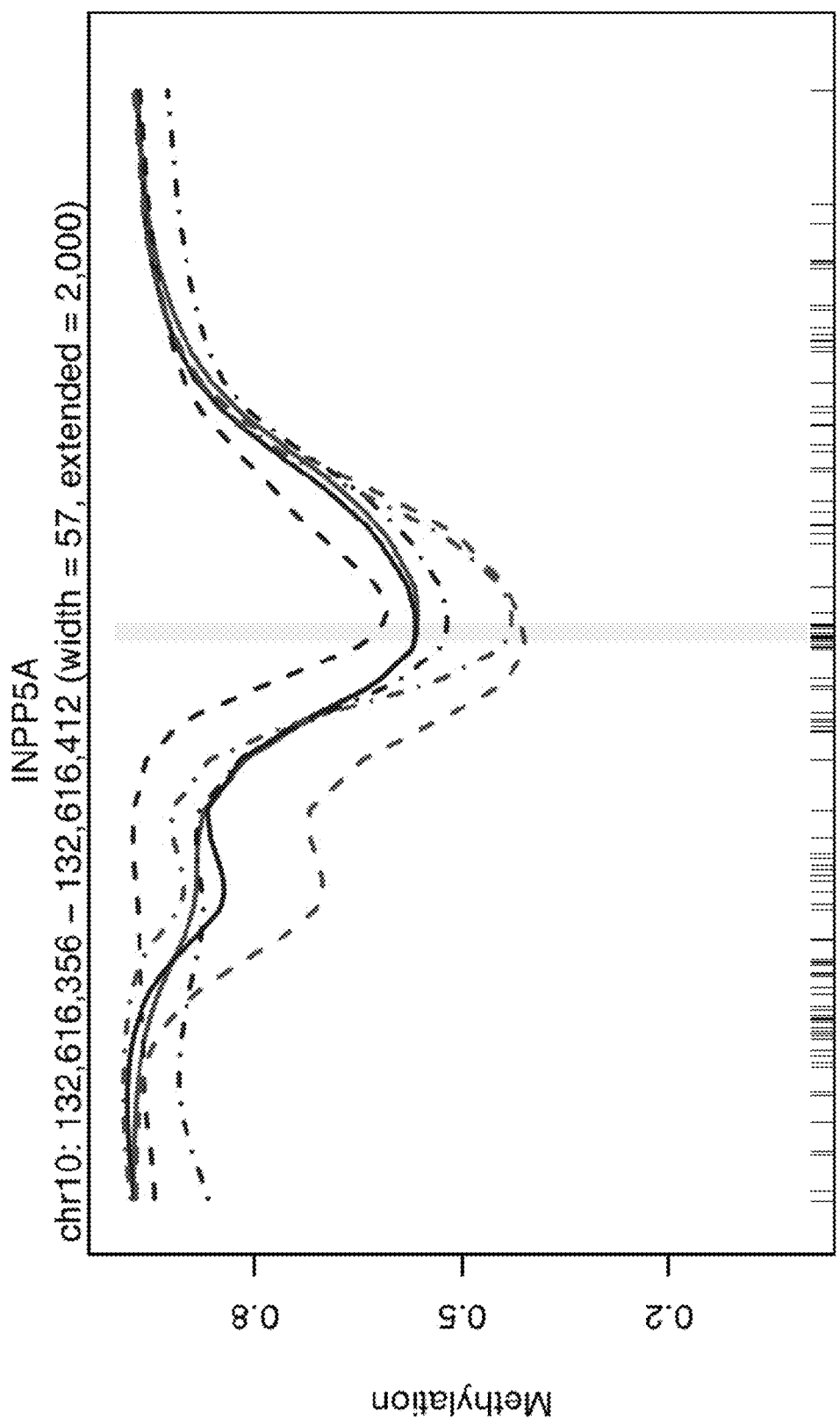
Figure 2:
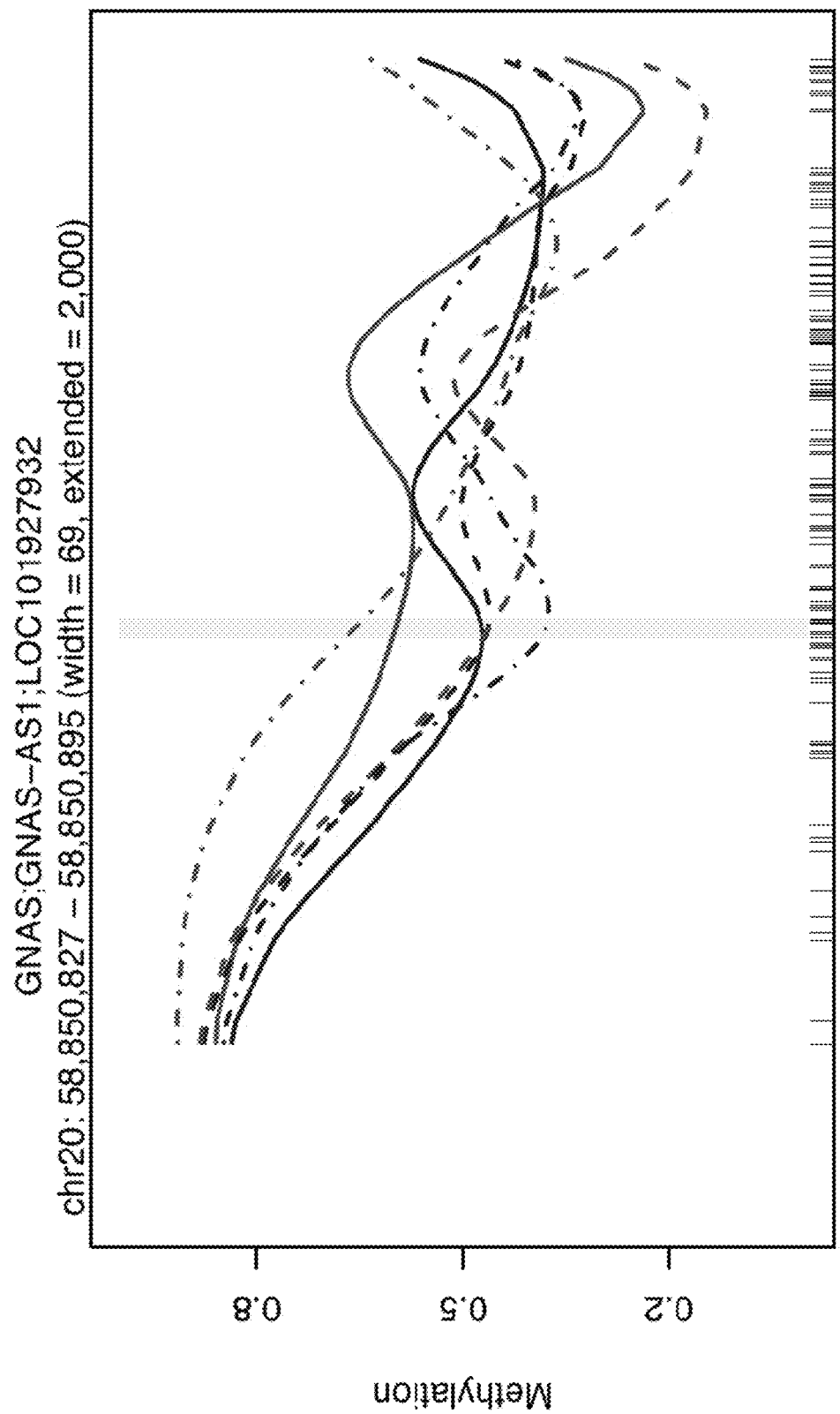
Figure 2:
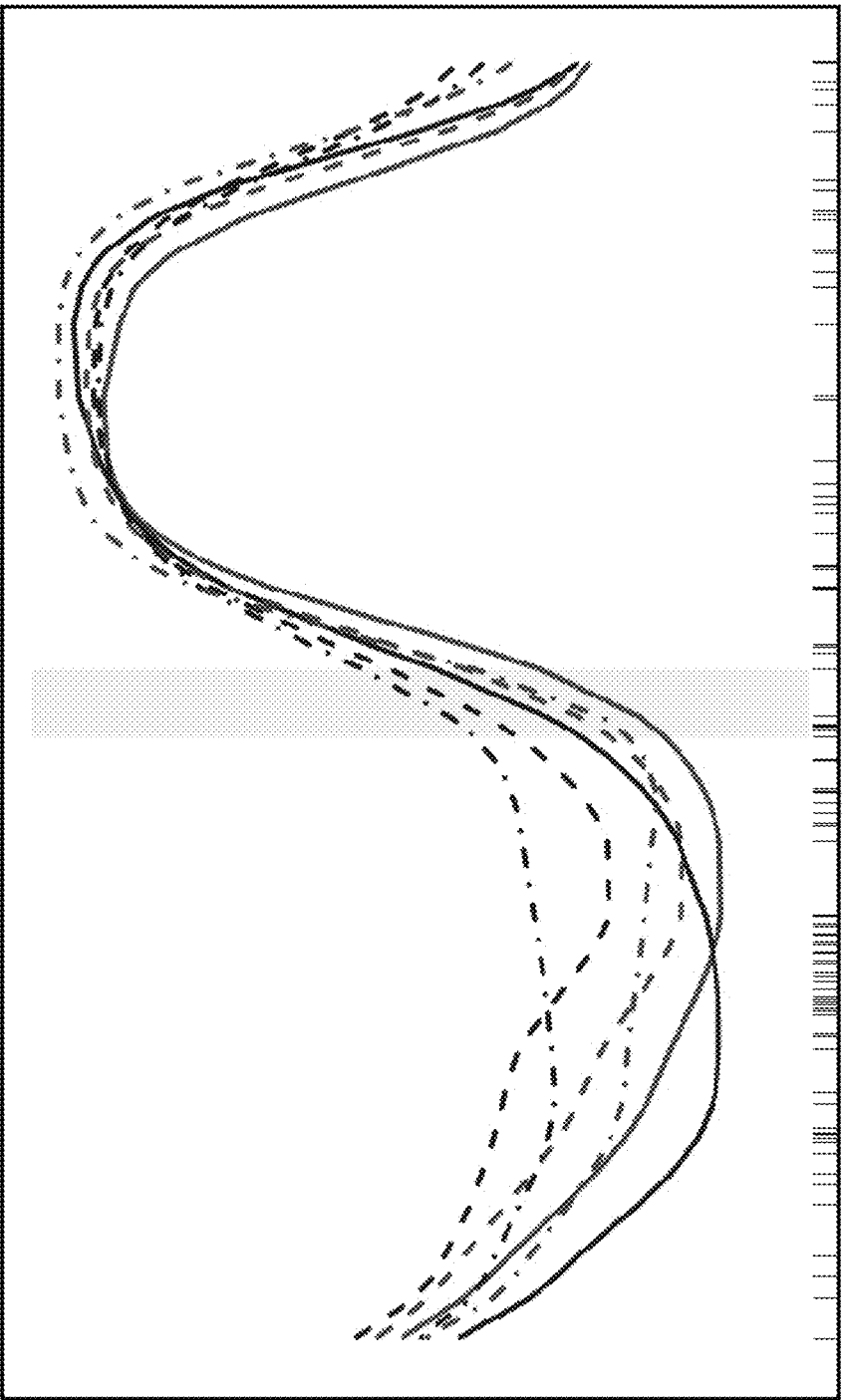
Figure 2:
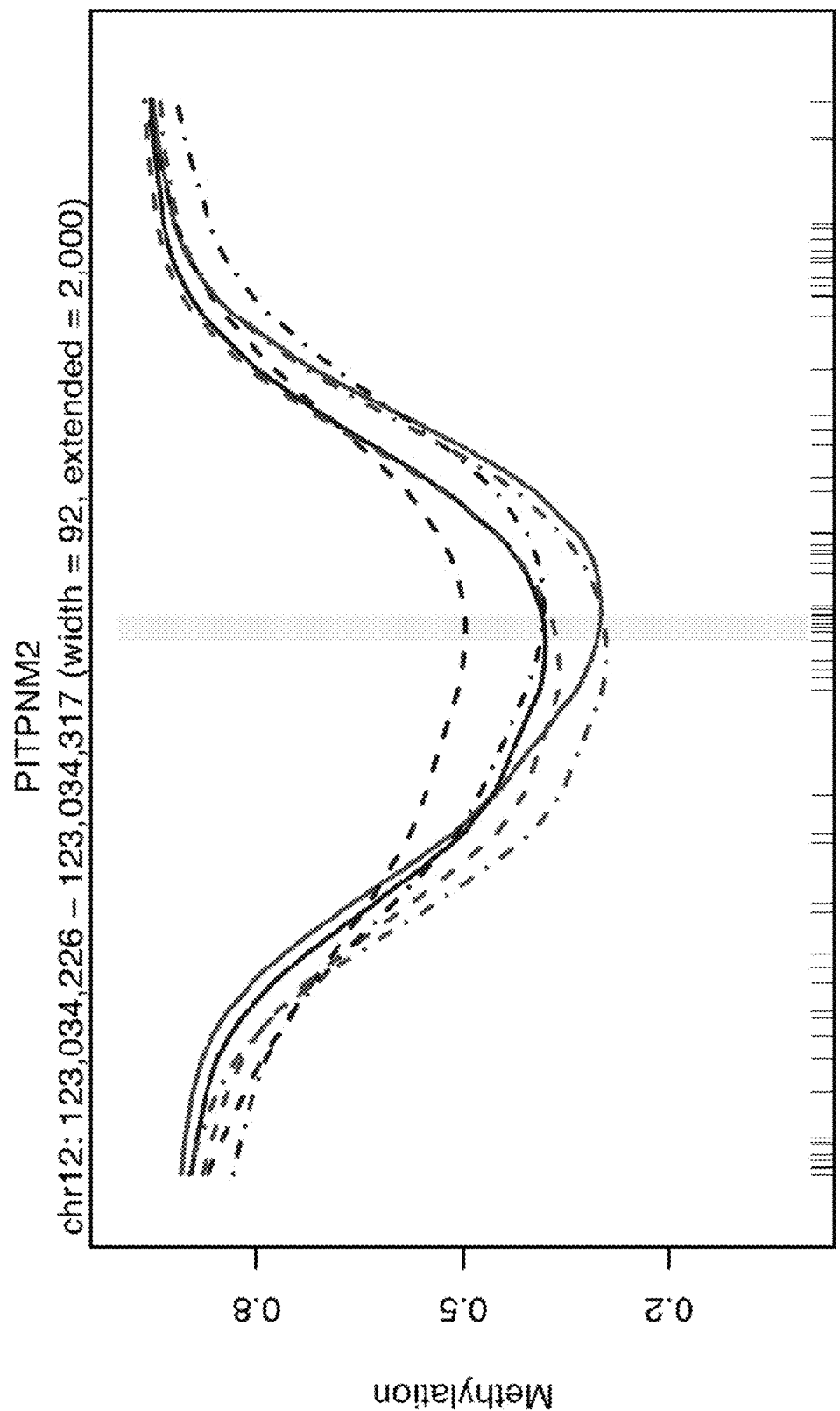
Figure 2:
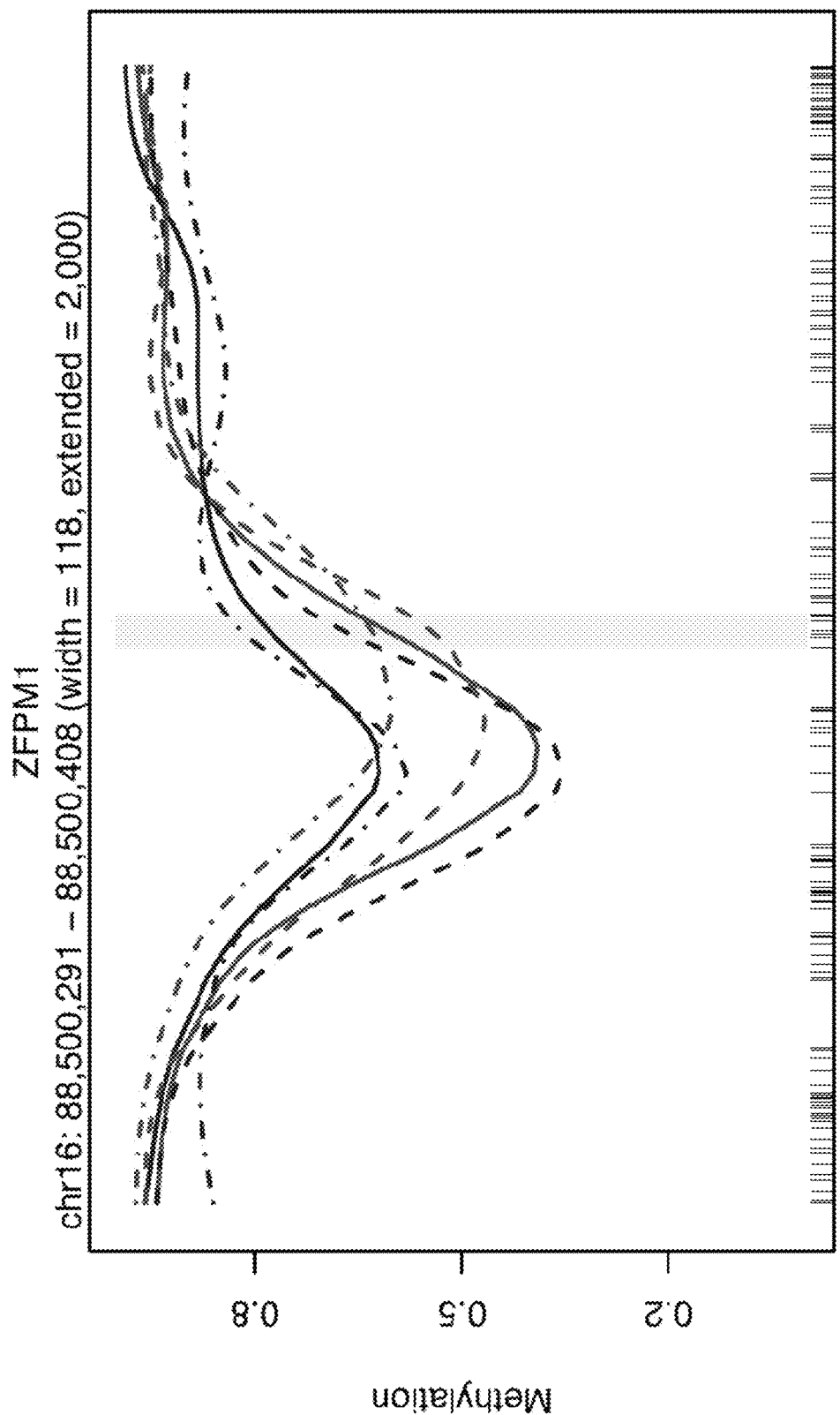
Figure 2:
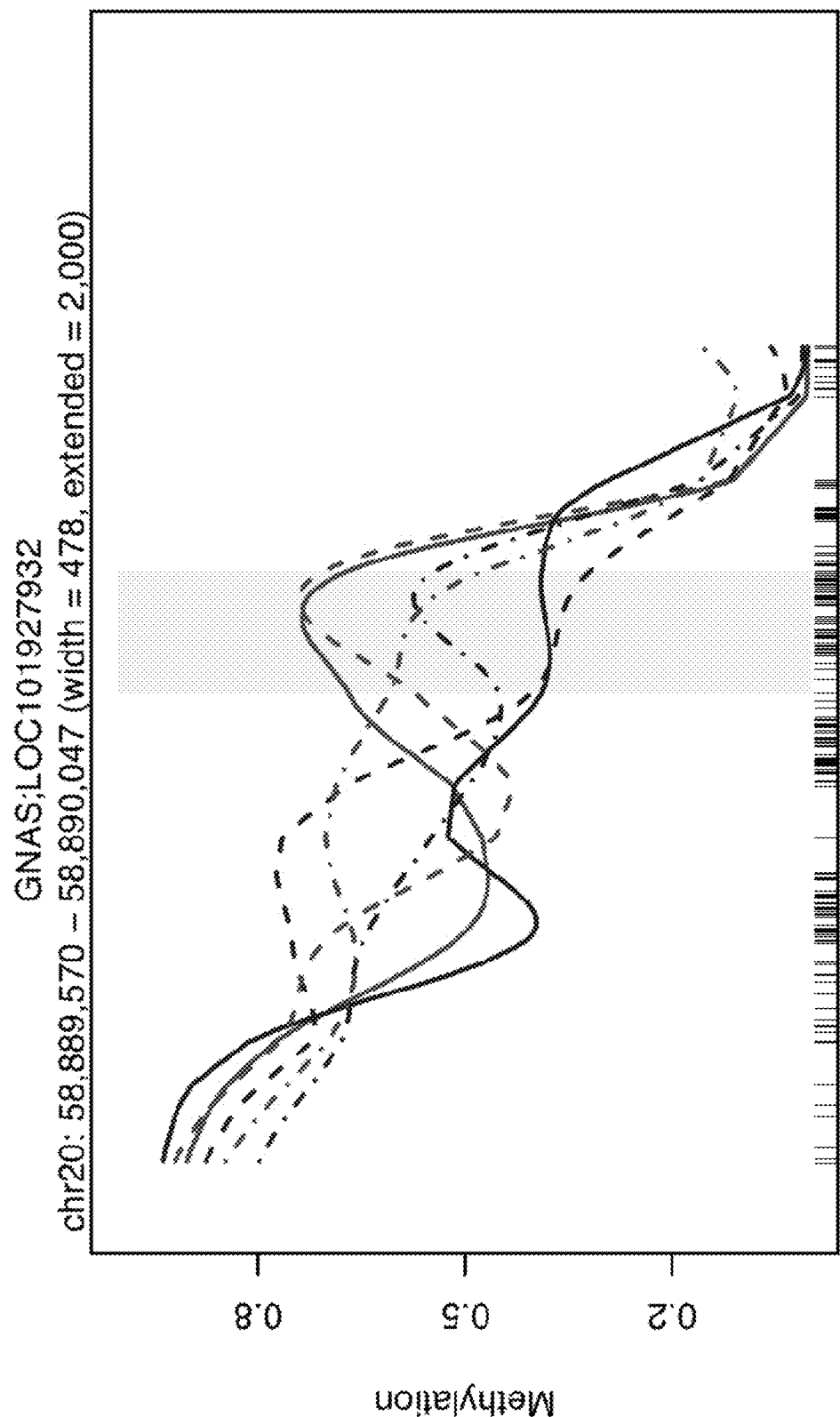
Figure 2:
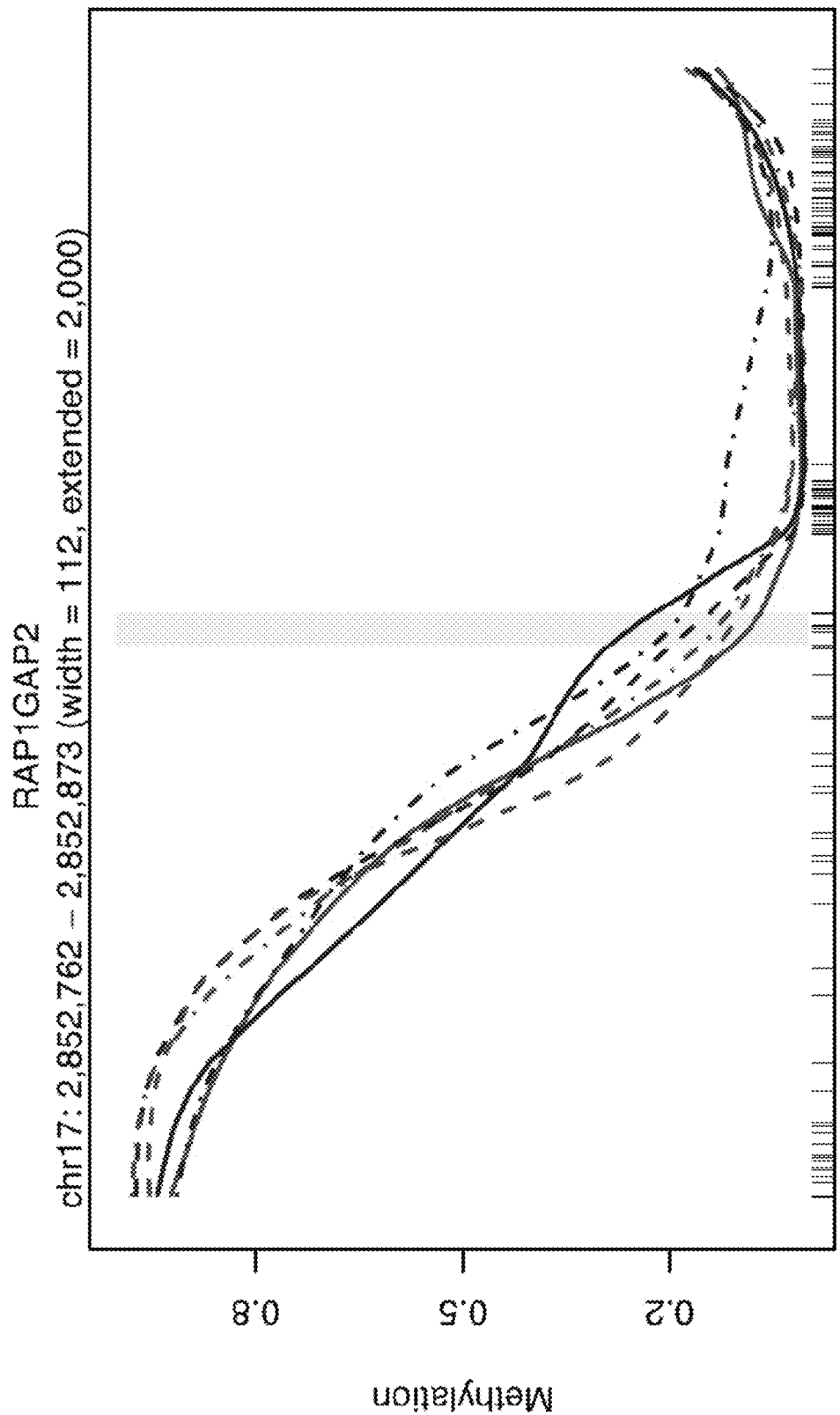
Figure 2:
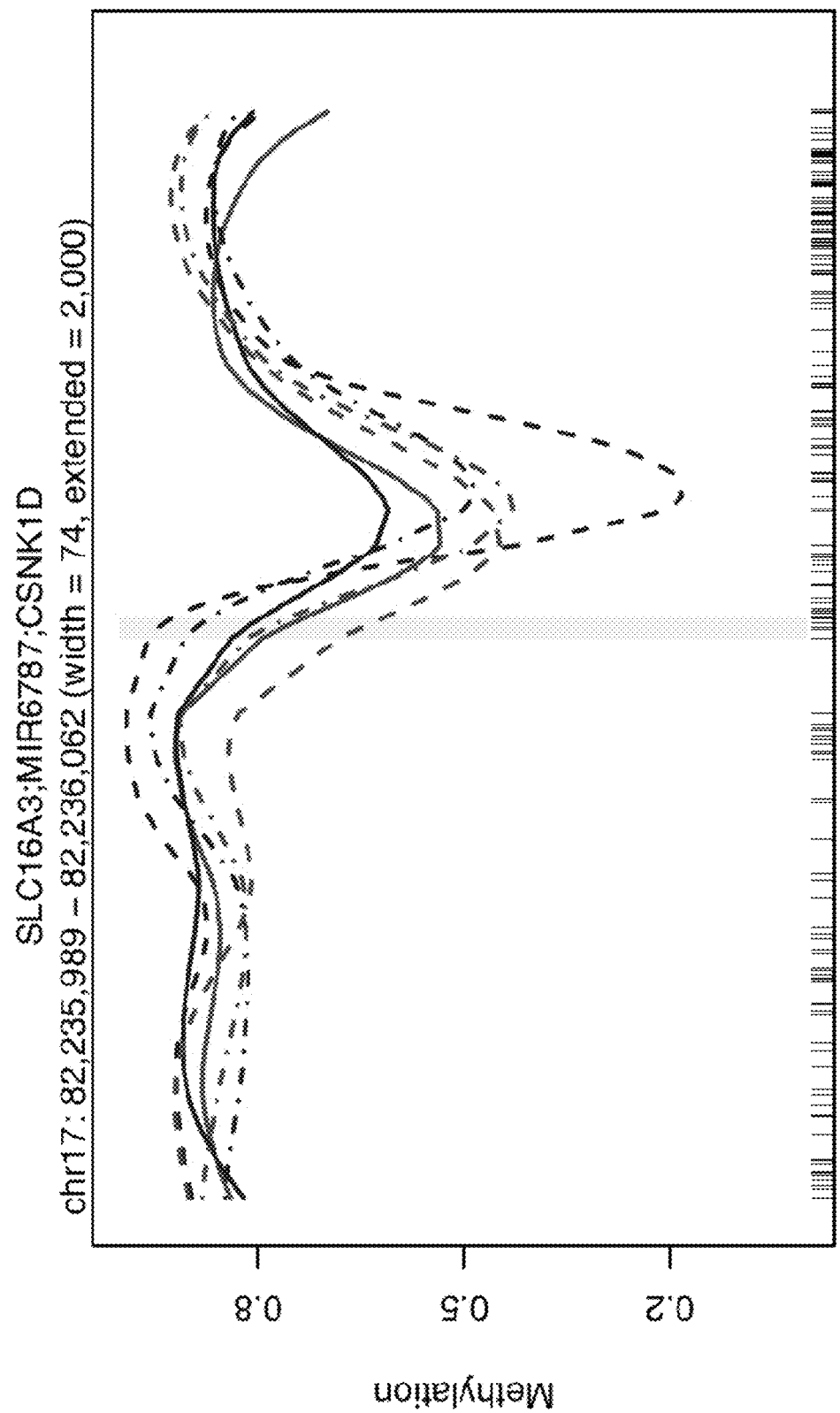
Figure 2:
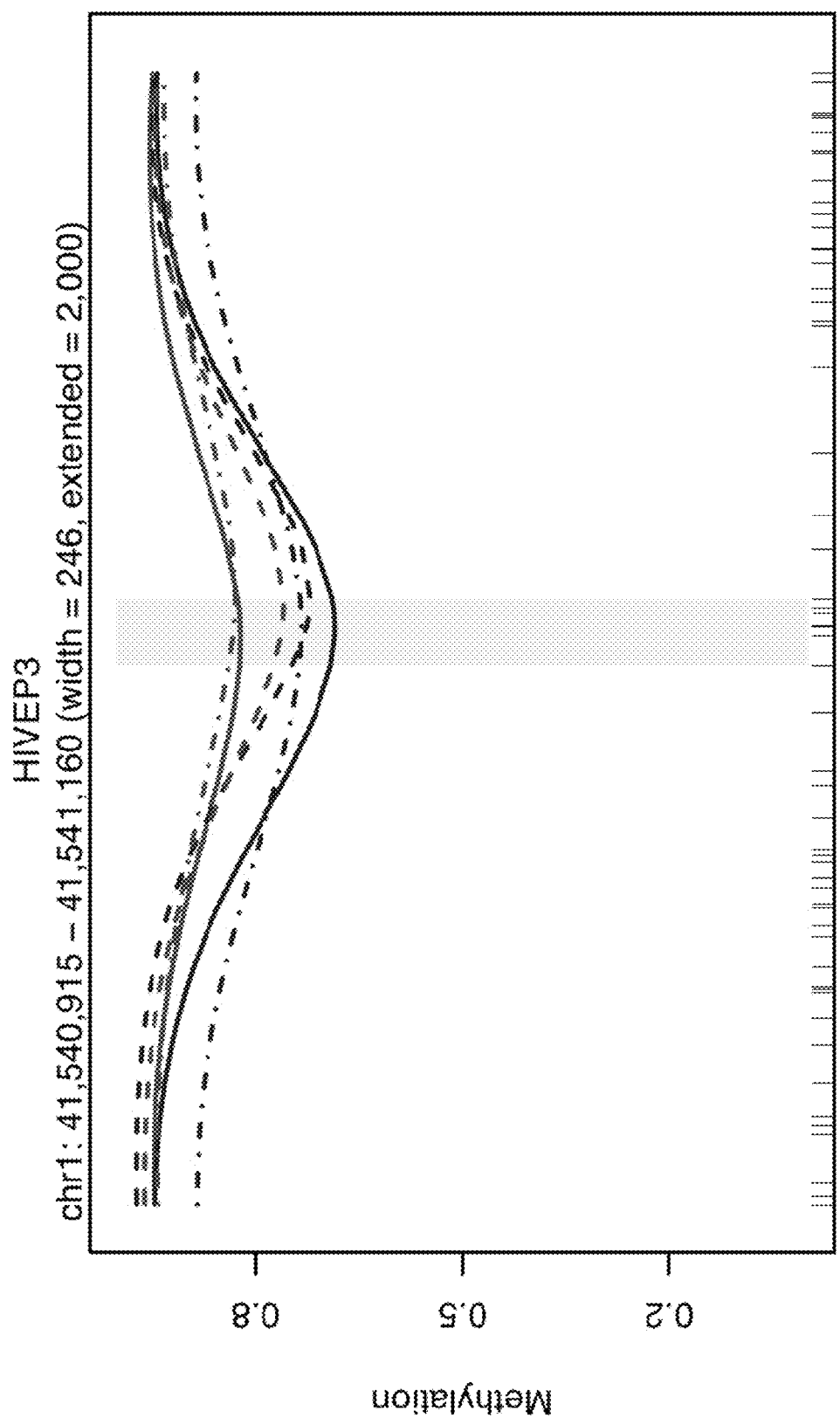
Figure 2:
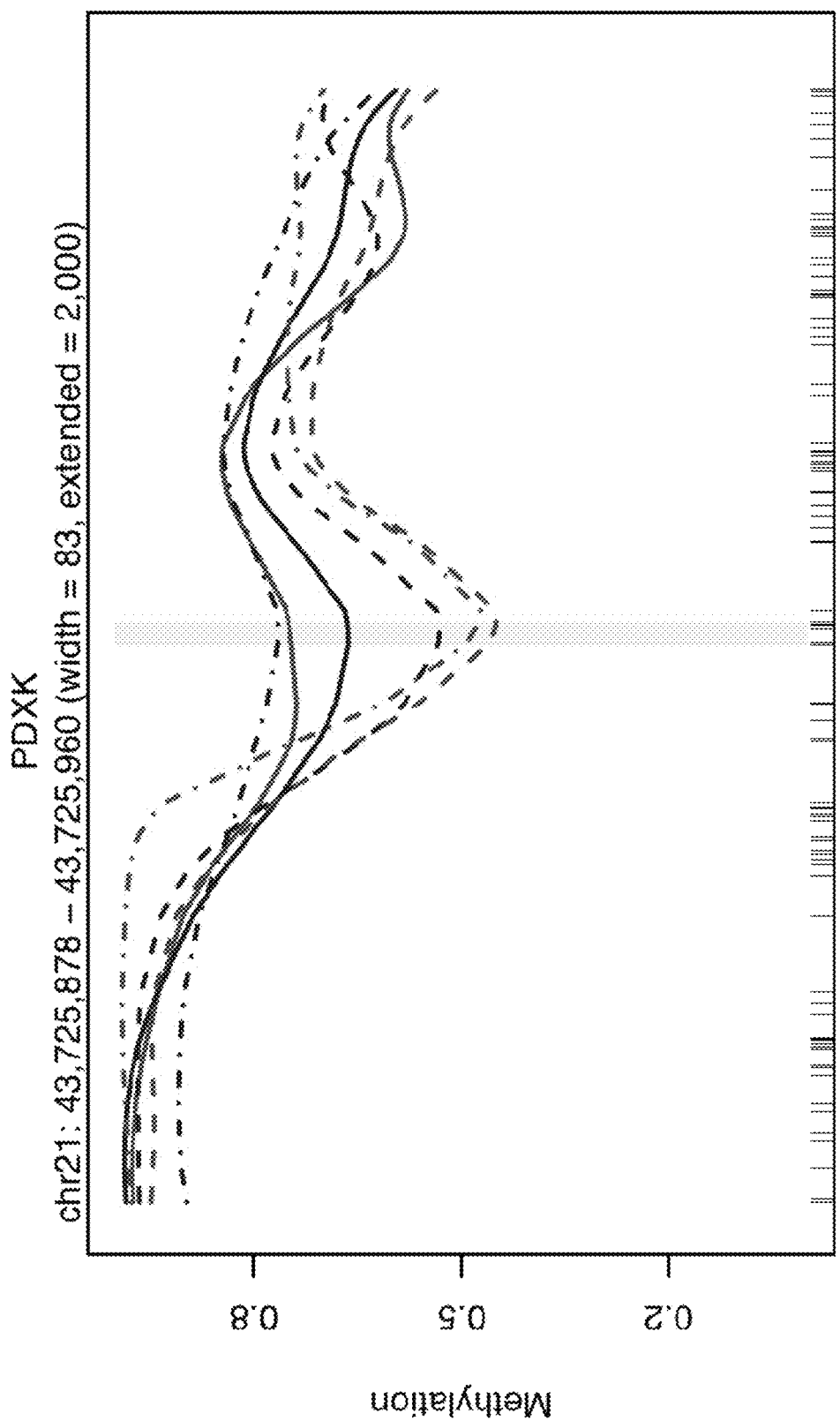
Figure 2:
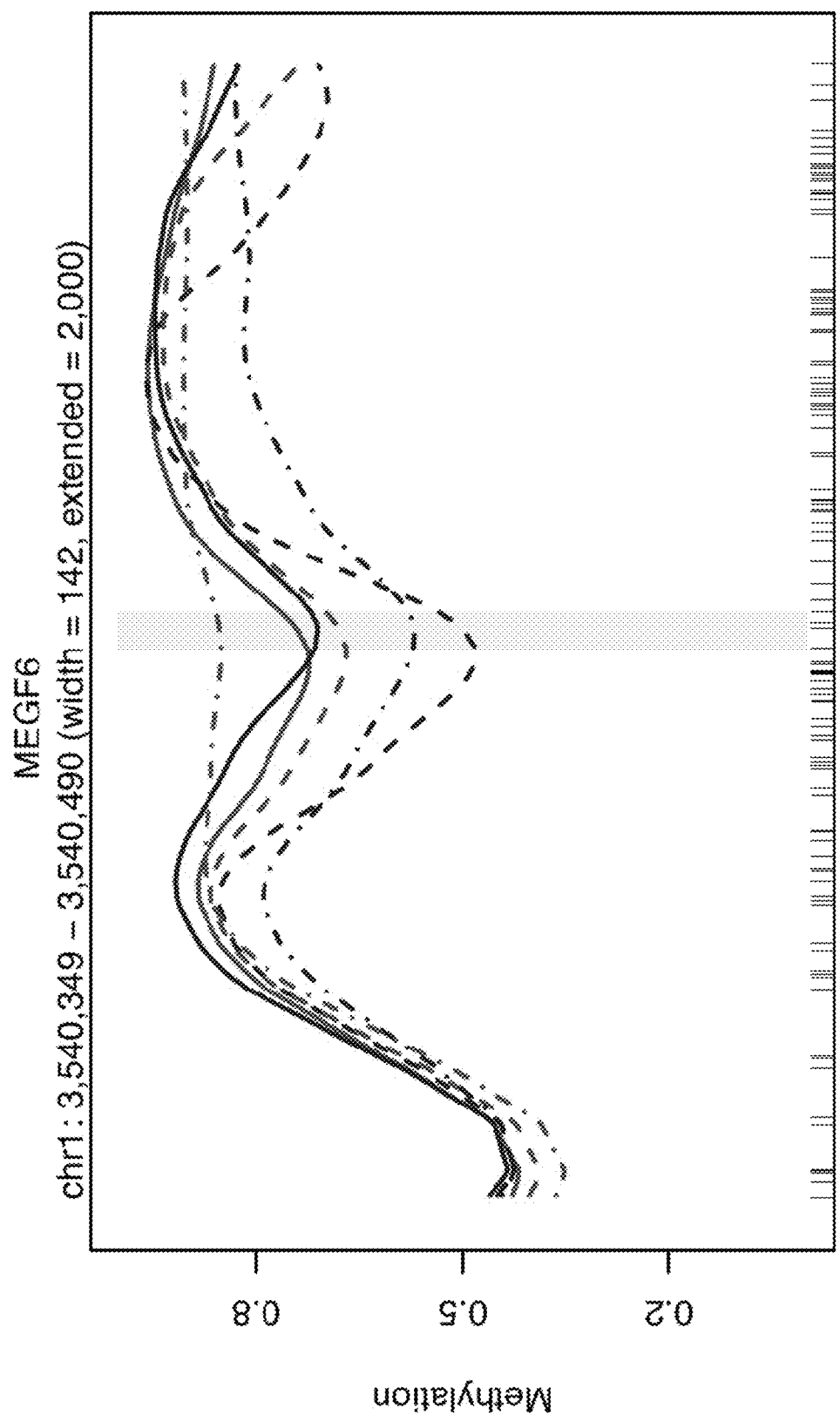
Figure 2:
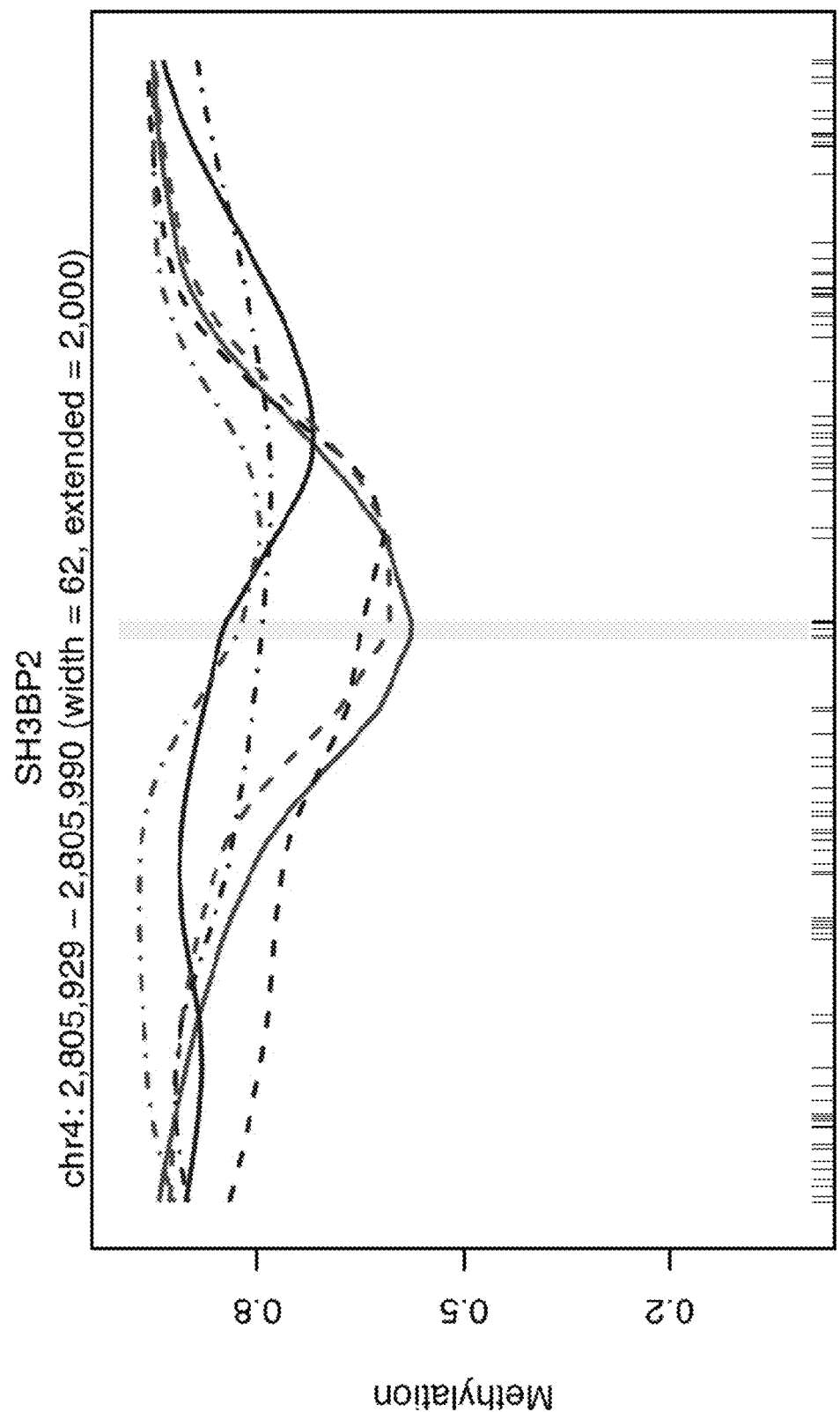

For comparisons to the anxiety-related DMRs and DMR-associated genes previously found in human blood, the DMRs found in monkeys were mapped to the human reference genome (hg38). This approach revealed an overlap of six DMR-associated genes between monkey brain, monkey blood, and human blood anxiety-related blood DMRs, including DIP2C, GRB10, and CRTC1 (FIG. 1). Furthermore, twelve DMR-associated genes were uniquely common to the monkey brain and human blood, and eight DMR-associated genes were uniquely common to monkey blood and human blood. These DMRs comprise multiple CpGs and a greater than 10% differential methylation related to anxiety (FIG. 2), which serves to substantiate these findings. Together, these data indicate that human blood contains anxiety-related changes in DNA methylation that provides the foundation for developing a blood-based biomarker profile for diagnosing the individual expression of clinical anxiety.

Using the overlapping genomic locations of the anxiety-related DMRs identified here and previously, we built a custom resequencing panel that will be used to detect deviations from healthy anxious trajectories and bolster diagnostic efforts with an epigenetic metric that integrates heritable and acquired variables that influence the expression of an anxious temperament and the development of clinical anxiety and depressive disorders. This resequencing panel will use Illumina Custom Enrichment Panel technology that enables custom panel design between 2,000-67,000 probes using DesignStudio. Nextera Flex methodologies will be used for enrichment. The initial enrichment panel (i.e., AT enrichment panel v3) will examine the DNA methylation levels at all the CpGs found in the 26 anxiety-related DMRs that are overlapping between monkey brain, monkey blood, and/or human blood (FIG. 1; Table 2). This resequencing panel will be employed as a blood DNA methylation biomarker diagnostic test for clinical anxiety and depressive disorders, improving estimates of prognosis and to guide personalized treatment of clinical anxiety and depressive disorders.

RNA sequencing—The RNA sequencing was conducted using the same monkey brain tissue that was used to generate the DNA methylation data. Thus, these expression data provide a direct comparison with the monkey brain DNA methylation data to begin to identify a possible mechanism (DNA methylation) for the observed changes in expression that likely drive the AT phenotype. Approximately 60 genes have correlated changes in DNA methylation and gene expression levels in the monkey brain that are linked to the AT phenotype. Notably, 50% (3/6) of the genes that we find differentially methylated in all three tissues (human blood, monkey brain, and monkey blood) are among these 60 genes. These gene are GRB10, PDXK, and TRAPPC9. This additional connection to gene expression changes in the brain associated with the AT phenotype makes these three gene our top candidates. Ten more genes (13 in total) that have correlated changes in DNA methylation and gene expression levels in the monkey brain, also are differentially methylated in the monkey blood. These 10 genes (BRD3, DDX50, DUSP8, EHMT1, HCN2, IL17D, MICAL3, NACC2, PKD1, and VWA1) also are top candidates.

REFERENCES

1 Gross, C. & Hen, R. The developmental origins of anxiety. Nature reviews. Neuroscience 5, 545-552, doi:10.1038/nrn1429 (2004).
2 Kagan, J. & Snidman, N. Early childhood predictors of adult anxiety disorders. Biological psychiatry 46, 1536-1541 (1999).
3 Kalin, N. H. & Shelton, S. E. Nonhuman primate models to study anxiety, emotion regulation, and psychopathology. Ann N Y Acad Sci 1008, 189-200 (2003).
4 Shirtcliff, E. A. & Essex, M. J. Concurrent and longitudinal associations of basal and diurnal cortisol with mental health symptoms in early adolescence. Developmental psychobiology 50, 690-703, doi:10.1002/dev.20336 (2008).
5 Schmidt, L. A. et al. Behavioral and neuroendocrine responses in shy children. Developmental psychobiology 30, 127-140 (1997).
6 Klimes-Dougan, B., Hastings, P. D., Granger, D. A., Usher, B. A. & Zahn-Waxler, C. Adrenocortical activity in at-risk and normally developing adolescents: individual differences in salivary cortisol basal levels, diurnal variation, and responses to social challenges. Development and psychopathology 13, 695-719 (2001).
7 Essex, M. J., Klein, M. H., Cho, E. & Kalin, N. H. Maternal stress beginning in infancy may sensitize children to later stress exposure: effects on cortisol and behavior. Biological psychiatry 52, 776-784 (2002).
8 Burghy, C. A. et al. Developmental pathways to amygdala-prefrontal function and internalizing symptoms in adolescence. Nature neuroscience 15, 1736-1741, doi:10.1038/nn.3257 (2012).
9 Burghy, C. A. et al. Experience-Driven Differences in Childhood Cortisol Predict Affect-Relevant Brain Function and Coping in Adolescent Monozygotic Twins. Scientific reports 6, 37081, doi:10.1038/srep37081 (2016).
10 Erickson, K., Drevets, W. & Schulkin, J. Glucocorticoid regulation of diverse cognitive functions in normal and pathological emotional states. Neuroscience and biobehavioral reviews 27, 233-246 (2003).
11 Gunnar, M. & Quevedo, K. The neurobiology of stress and development. Annual review of psychology 58, 145-173, doi:10.1146/annurev.psych.58.110405.085605 (2007).
12 Urry, H. L. et al. Amygdala and ventromedial prefrontal cortex are inversely coupled during regulation of negative affect and predict the diurnal pattern of cortisol secretion among older adults. J Neurosci 26, 4415-4425, doi:10.1523/JNEUROSCI.3215-05.2006 (2006).
13 Bishop, S., Duncan, J., Brett, M. & Lawrence, A. D. Prefrontal cortical function and anxiety: controlling attention to threat-related stimuli. Nature neuroscience 7, 184-188, doi:10.1038/nn1173 (2004).
14 Stein, M. B., Simmons, A. N., Feinstein, J. S. & Paulus, M. P. Increased amygdala and insula activation during emotion processing in anxiety-prone subjects. The American journal of psychiatry 164, 318-327, doi:10.1176/ajp.2007.164.2.318 (2007).
15 Phelps, E. A. & LeDoux, J. E. Contributions of the amygdala to emotion processing: from animal models to human behavior. Neuron 48, 175-187, doi:10.1016/j.neuron.2005.09.025 (2005).
16 Kalin, N. H., Shelton, S. E. & Davidson, R. J. The role of the central nucleus of the amygdala in mediating fear and anxiety in the primate. J Neurosci 24, 5506-5515, doi:10.1523/JNEUROSCI.0292-04.2004 (2004).
17 Shackman, A. J. et al. Heightened extended amygdala metabolism following threat characterizes the early phenotypic risk to develop anxiety-related psychopathology. Molecular psychiatry, doi:10.1038/mp.2016.132 (2016).
18 Hettema, J. M., Neale, M. C. & Kendler, K. S. A review and meta-analysis of the genetic epidemiology of anxiety disorders. The American journal of psychiatry 158, 1568-1578 (2001).
19 Abdolmaleky, H. M. et al. Hypomethylation of MB-COMT promoter is a major risk factor for schizophrenia and bipolar disorder. Hum Mol Genet 15, 3132-3145, doi:10.1093/hmg/ddl253 (2006).
20 Poulter, M. O. et al. GABAA receptor promoter hypermethylation in suicide brain: implications for the involvement of epigenetic processes. Biological psychiatry 64, 645-652, doi:10.1016/j.biopsych.2008.05.028 (2008).

21 Kuratomi, G. et al. Aberrant DNA methylation associated with bipolar disorder identified from discordant monozygotic twins. Molecular psychiatry 13, 429-441, doi:10.1038/sj.mp.4002001 (2008).

22 Collishaw, S. et al. Resilience to adult psychopathology following childhood maltreatment: evidence from a community sample. Child abuse & neglect 31, 211-229, doi:10.1016/j.chiabu.2007.02.004 (2007).

23 Kappeler, L. & Meaney, M. J. Epigenetics and parental effects. BioEssays: news and reviews in molecular, cellular and developmental biology 32, 818-827, doi:10.1002/bies.201000015 (2010).

24 Weaver, I. C. et al. Epigenetic programming by maternal behavior. Nature neuroscience 7, 847-854, doi:10.1038/nn1276 (2004).

25 Murphy, T. M. et al. Anxiety is associated with higher levels of global DNA methylation and altered expression of epigenetic and interleukin-6 genes. Psychiatric genetics 25, 71-78, doi:10.1097/YPG.0000000000000055 (2015).

26 Alisch, R. S. et al. Differentially methylated plasticity genes in the amygdala of young primates are linked to anxious temperament, an at risk phenotype for anxiety and depressive disorders. J Neurosci 34, 15548-15556, doi:10.1523/JNEUROSCI.3338-14.2014 (2014).

27 Labrie, V., Clapcote, S. J. & Roder, J. C. Mutant mice with reduced NMDA-NR1 glycine affinity or lack of D-amino acid oxidase function exhibit altered anxiety-like behaviors. Pharmacology, biochemistry, and behavior 91, 610-620, doi:10.1016/j.pbb.2008.09.016 (2009).

28 Rodrigues, S. M., Bauer, E. P., Farb, C. R., Schafe, G. E. & LeDoux, J. E. The group I metabotropic glutamate receptor mGluR5 is required for fear memory formation and long-term potentiation in the lateral amygdala. J Neurosci 22, 5219-5229 (2002).

29 Bartels, M., de Geus, E. J., Kirschbaum, C., Sluyter, F. & Boomsma, D. I. Heritability of daytime cortisol levels in children. Behavior genetics 33, 421-433 (2003).

30 Van Hulle, C. A., Shirtcliff, E. A., Lemery-Chalfant, K. & Goldsmith, H. H. Genetic and environmental influences on individual differences in cortisol level and circadian rhythm in middle childhood. Hormones and behavior 62, 36-42, doi:10.1016/j.yhbeh.2012.04.014 (2012).

31 Renteria, M. E. et al. Genetic architecture of subcortical brain regions: common and region-specific genetic contributions. Genes, brain, and behavior 13, 821-830, doi:10.1111/gbb.12177 (2014).

32 Waszczuk, M. A., Zavos, H. M., Gregory, A. M. & Eley, T. C. The phenotypic and genetic structure of depression and anxiety disorder symptoms in childhood, adolescence, and young adulthood. JAMA Psychiatry 71, 905-916, doi:10.1001/jamapsychiatry.2014.655 (2014).

33 Alisch, R. S. et al. A multi-dimensional characterization of anxiety in monozygotic twin pairs reveals susceptibility loci in humans. Translational psychiatry 7, 1282, doi:10.1038/s41398-017-0047-9 (2017).

34 Verma, N. et al. TET proteins safeguard bivalent promoters from de novo methylation in human embryonic stem cells. Nat Genet 50, 83-95, doi:10.1038/s41588-017-0002-y (2018).

35 Dai, H. Q. et al. TET-mediated DNA demethylation controls gastrulation by regulating Lefty-Nodal signalling. Nature 538, 528-532, doi:10.1038/nature20095 (2016).

36 Langmead, B. & Salzberg, S. L. Fast gapped-read alignment with Bowtie 2. Nature methods 9, 357-359, doi:10.1038/nmeth.1923 (2012).

37 Krueger, F. & Andrews, S. R. Bismark: a flexible aligner and methylation caller for Bisulfite-Seq applications. Bioinformatics 27, 1571-1572, doi:10.1093/bioinformatics/btr167 (2011).

38 Tsuji, J. & Weng, Z. Evaluation of preprocessing, mapping and postprocessing algorithms for analyzing whole genome bisulfite sequencing data. Briefings in bioinformatics 17, 938-952, doi:10.1093/bib/bbv103 (2016).

39 Kunde-Ramamoorthy, G. et al. Comparison and quantitative verification of mapping algorithms for whole-genome bisulfite sequencing. Nucleic Acids Res 42, e43, doi:10.1093/nar/gkt1325 (2014).

40 Speir, M. L. et al. The UCSC Genome Browser database: 2016 update. Nucleic Acids Res 44, D717-725, doi:10.1093/nar/gkv1275 (2016).

41 Wu, H. et al. Detection of differentially methylated regions from whole-genome bisulfite sequencing data without replicates. Nucleic Acids Res 43, e141, doi:10.1093/nar/gkv715 (2015).

42 Feng, H., Conneely, K. N. & Wu, H. A Bayesian hierarchical model to detect differentially methylated loci from single nucleotide resolution sequencing data. Nucleic Acids Res 42, e69, doi:10.1093/nar/gku154 (2014).

43 Fox, A. S. et al. Central amygdala nucleus (Ce) gene expression linked to increased trait-like Ce metabolism and anxious temperament in young primates. Proc Natl Acad Sci USA 109, 18108-18113, doi:10.1073/pnas.1206723109 (2012).

We claim:

1. A method of amplifying at least one of six differentially methylated region (DMR) associated genes comprising the steps of:
   (a) providing a reaction mixture comprising bisulfite modified target DNA from a subject and at least one pair of primers designed to amplify at least one DMR-associated gene selected from the group consisting of DIP2C, GRB10, INPP5A, GNAS, PDXK, and TRAPPC9, wherein the primer pair comprises a first and a second primer that are complementary to the DMR-associated gene;
   (b) heating the reaction mixture to a first predetermined temperature for a first predetermined time;
   (c) cooling the reaction mixture to a second predetermined temperature for a second predetermined time under conditions to allow the first and second primers to hybridize with their complementary sequences on the target DNA; and
   (d) repeating steps (b) and (c) wherein an amplified target DNA sample is formed.

2. The method of claim 1, wherein the reaction mixture additionally comprises a polymerase and a plurality of free nucleotides comprising adenine, thymine, cytosine, and guanine.

3. The method of claim 1, wherein the reaction mixture additionally comprises a reaction buffer and $MgCl_2$.

4. The method of claim 1, wherein in step (a), (i) a first reaction mixture comprising a first portion of bisulfite modified target DNA and a pair of primers designed to amplify DIP2C; (ii) a second reaction mixture comprising a second portion of bisulfite modified target DNA and a pair of primers designed to amplify INPP5A; (iii) a third reaction mixture comprising a third portion of bisulfite modified target DNA and a pair of primers designed to amplify PDXK; (iv) a forth reaction mixture comprising a forth portion of bisulfite modified target DNA and a pair of primers designed to amplify GNAS; (v) a fifth reaction mixture comprising a fifth portion of bisulfite modified target DNA and pair of primers designed to amplify GRB10; (vi) and a sixth reaction mixture comprising a sixth portion of bisulfite modified target DNA and a pair of primers designed to amplify TRAPPC9 are provided.

5. The method of claim 1, wherein the primers are specific for a DMR selected from the group consisting of SEQ ID NOs:7-18, 50-59, 67-69, and 73-75.

6. The method of claim 1, wherein at least one of the primers in the primer pair is biotinylated.

7. The method of claim 4, additionally comprising providing reaction mixtures comprising subsequent portions of bisulfite modified target DNA and a pair of primers designed to amplify one or more DMR-associated genes selected from the group consisting of C17ORF97, CACNA2D4, CRTC1, MEGF6, HIVEP3, OPCML, PITPNM2, ZFPM1, RAP1GAP2, NFATC1, RNF126, FSTL3, SH3BP2, NEURL1B, MAD1L1, HSPA12B, IGF2, PEG10, PEG3, SLC16A3, SYTL1, and ZIM2.

8. The method of claim 7, wherein the primers are designed to amplify a DMR selected from the group consisting of SEQ ID NOs:1-6, 19-49, 60-66, and 70-72.

9. The method of claim 1, wherein the target DNA is isolated from a blood sample or a saliva sample from the subject.

10. The method of claim 1, wherein the subject is a human or non-human primate.

11. The method of claim 1, wherein the providing the reaction mixture further comprises providing at least one pair of primers designed to amplify at least one DMR-associated gene selected from the group consisting of C17ORF97, CACNA2D4, CRTC1, MEGF6, HIVEP3, OPCML, PITPNM2, ZFPM1, RAP1GAP2, NFATC1, RNF126, FSTL3, SH3BP2, NEURL1B, MAD1L1, HSPA12B, IGF2, PEG10, PEG3, SLC16A3, SYTL1, ZIM2, BRD3, DDX50, DUSP8, EHMT1, HCN2, IL17D, MICAL3, NACC2, PKD1, and VWA1.

* * * * *

SEQUENCE LISTING

<160> NUMBER OF SEQ ID NOS: 75

<210> SEQ ID NO 1
<211> LENGTH: 115
<212> TYPE: DNA
<213> ORGANISM: Homo sapiens

<400> SEQUENCE: 1
cgctgaggcc ctgaggacac accctggtga acccttgtca ccagggccca tccccagggg     60
cacccgccca tagggacaca ggcacgtccc tgggactaca ggcctggcac tcacc          115

<210> SEQ ID NO 2
<211> LENGTH: 142
<212> TYPE: DNA
<213> ORGANISM: Homo sapiens

```
<400> SEQUENCE: 2
cgggtttccc gctgcactgg gaagacagcc agctgaagaa tgttggcctg gggaggccca      60
gattcagcca cccacaggaa cgtggcccca gctttgcaac cggaaggccc aggttcaggc     120
ctgggctcca gggcccatgg gc                                              142

<210> SEQ ID NO 3
<211> LENGTH: 57
<212> TYPE: DNA
<213> ORGANISM: Homo sapiens

<400> SEQUENCE: 3
cggtgtccag ccttaactcc tccacggtga ggcgggaggg aggggacccg ggcggcc         57

<210> SEQ ID NO 4
<211> LENGTH: 306
<212> TYPE: DNA
<213> ORGANISM: Homo sapiens

<400> SEQUENCE: 4
cgatgcgtag cccctgcctg cccctccctc gccgcgggac ccaccgctgc agcccccag       60 cctgccacct atgacccggg tctgaagcct ccgcgctgcc cgcggccccg acgtgagccc     120
tgcgagcggc cctgactccc acccactccc gtccgcagct gagcggcagc cagatgagcc     180
tgtcaggcga cgcggaggcg gtgcaggtcc gcggctccgt gcacttcgcg ctgcactacg     240
agccgggcgc cgccgagctg cgcgtgcacg tgatccagtg ccagggcctg gccgccgccc     300
ggcgcc                                                                306

<210> SEQ ID NO 5
<211> LENGTH: 246
<212> TYPE: DNA
<213> ORGANISM: Homo sapiens

<400> SEQUENCE: 5
cgggtttagc tggactctaa atggacactg caaccacact ggtgctccag acataaacag      60
ccagtaggtg agtgggtggg aaaacaggaa ggaagggagg gtgtggtcac ggctcagagg     120
actgaggtgg cctgtctgat taggacgctg cgagtgcagt ggttaggcat ggggtgttga     180
tgcatcagac tgccgagttc aaatcctgcc tcctccgacc agctgtgtga tcctgagcaa     240
gcaccc                                                                246

<210> SEQ ID NO 6
<211> LENGTH: 90
<212> TYPE: DNA
<213> ORGANISM: Homo sapiens

<400> SEQUENCE: 6
cgctgcggga tggtgccaga gcccggagcc accaggcttg ccactctggc tgccacacag      60
aagagtctcc ttgcgctcag cagactctgc                                       90

<210> SEQ ID NO 7
<211> LENGTH: 62
<212> TYPE: DNA
<213> ORGANISM: Homo sapiens

<400> SEQUENCE: 7
cgcggggaga cgcctgttct ggaggccagg cccgcaggca ggaaggaaaa gcacggccgg      60
``` ac                                                                                    62

<210> SEQ ID NO 8
<211> LENGTH: 99
<212> TYPE: DNA
<213> ORGANISM: Homo sapiens

<400> SEQUENCE: 8
cgaaaagaaa gacctgccct tggacaccag gtgagcccgg gcccagggca taccgggcag    60
tgagggtccc tggggcgcct gggcctgacc cgggtgtcc                           99

<210> SEQ ID NO 9
<211> LENGTH: 122
<212> TYPE: DNA
<213> ORGANISM: Homo sapiens

<400> SEQUENCE: 9
cgttcacgca gcggcccatc cggctgtacg agcaggtgcg gctgcgcctg gtggccgtgc    60
gccctggctg gagcggcgcg ctgcgcttcg gcttcaccgc gcacgatccg tcgctcatga   120
gc                                                                  122

<210> SEQ ID NO 10
<211> LENGTH: 199
<212> TYPE: DNA
<213> ORGANISM: Homo sapiens

<400> SEQUENCE: 10
cgagctgccc gccgacccag acgcgctgct cgaccgcaaa gagtactggg tggtggcgcg    60
cgccgggccc gtgccgagcg gcggcgacgc gctcagcttc acgctgcggc ccggcggcga   120
cgtgctcctg ggcatcaacg ggcgtccgcg cggccgcctg ctgtgcgtcg acaccacgca   180
ggcgctctgg gccttcttc                                                199

<210> SEQ ID NO 11
<211> LENGTH: 10
<212> TYPE: DNA
<213> ORGANISM: Homo sapiens

<400> SEQUENCE: 11
tgactcaaca                                                           10

<210> SEQ ID NO 12
<211> LENGTH: 54
<212> TYPE: DNA
<213> ORGANISM: Homo sapiens

<400> SEQUENCE: 12
aaatctttca cttgcagagc gagcaggcgc tctggtgctg ctacccagcg cggt          54

<210> SEQ ID NO 13
<211> LENGTH: 160
<212> TYPE: DNA
<213> ORGANISM: Homo sapiens

<400> SEQUENCE: 13
cgacgagggg cagagcctcc ctcagcaaag cgtcccactc aggaaacggg gacgaggggc    60
agagcctccc tcagcaaagc gtcccactca ggaaacgggg acgaggggca gagcctccct   120
cagcaaagcg tccccactcag gaaacacgga agagacgggc                        160

<210> SEQ ID NO 14
<211> LENGTH: 102
<212> TYPE: DNA
<213> ORGANISM: Homo sapiens

<400> SEQUENCE: 14
cggcaacgaa gctcgggatc tcggactgca gcgagcccgc ggcaggcggg caggggccg      60 cgcggcaaga cctccccgcc tccctcccgg gccctgtccg cc                       102

<210> SEQ ID NO 15
<211> LENGTH: 40
<212> TYPE: DNA
<213> ORGANISM: Homo sapiens

<400> SEQUENCE: 15
gcgcaggccg atccgcccgc cgccccggct cgcgcccacc                           40

<210> SEQ ID NO 16
<211> LENGTH: 61
<212> TYPE: DNA
<213> ORGANISM: Homo sapiens

<400> SEQUENCE: 16
gcagacaggc gggggacatc gcggccgcgg caagctagag atgccgcctg ctcgagcaac    60
c                                                                    61

<210> SEQ ID NO 17
<211> LENGTH: 205
<212> TYPE: DNA
<213> ORGANISM: Homo sapiens

<400> SEQUENCE: 17
cgcgcttcaa cttcggttgg tgtgtgtcga agaaacctga ctgcgccctg aggagaacag    60
cggagaaggt ccaccgagcc tggcgaaagg tccgctgagc gggctgtcgt ccggagccac   120
tccgggctgc ggagcaccca gtggagaccg cgcctggctc aggtgtggga ccccatcctt   180
cctgtcttcg cagaggagtc ctcgc                                         205

<210> SEQ ID NO 18
<211> LENGTH: 88
<212> TYPE: DNA
<213> ORGANISM: Homo sapiens

<400> SEQUENCE: 18
ctgggcccgc ctcctctgag gtgaactgcc caggcccgc ctctcctggg cccgcctcct     60
ctgatgtgag ctcacccaga tcccacct                                       88

<210> SEQ ID NO 19
<211> LENGTH: 10
<212> TYPE: DNA
<213> ORGANISM: Homo sapiens

<400> SEQUENCE: 19
ccccaggccc                                                           10

<210> SEQ ID NO 20
<211> LENGTH: 100
<212> TYPE: DNA
<213> ORGANISM: Homo sapiens

<400> SEQUENCE: 20
cgcccaccca ggtcctccgc agctgtccgc aggggaagac accagctaga tgtaagtgcg     60
cagctgcagc aatcccgcga tccacaaagt aatgacgccc                          100

<210> SEQ ID NO 21
<211> LENGTH: 102
<212> TYPE: DNA
<213> ORGANISM: Homo sapiens

<400> SEQUENCE: 21
cgcagctgtc cgcaggggaa gacaccagct agatgtaagt gcgcagctgc agcaatcccg     60
cgatccacaa agtaatgacg cccgcccaga tcctccgcag cc                       102

<210> SEQ ID NO 22
<211> LENGTH: 437
<212> TYPE: DNA
<213> ORGANISM: Homo sapiens

<400> SEQUENCE: 22
cgctggtcct ccgcagcctt ctccagggga ggacacccag ctaggtctct gcgcagctgc     60
aggagtgcca caatcctcag ggtactgacg ctcacccagg tcctccgcag ccttccgcag    120
gggagatacc cagctaggtc tcagcgcgca gcttcagcat ccccgcgatc cgcagagtat    180
tgacgcccac ccgggtcctc cgcagcctag agcaagggac tgcggaacga gtgccgcaat    240
cttcagggta ttgacgccca cccgggtcct ccgcagccaa gagcaaggga ctgcggaagg    300
agtgccgcaa tcttcagggt attgacgccc acccgggtcc tccgcagcct agagcaggga    360
actgcggaaa gagtgccaca atcctcaggg tattgacgcc cacccaagtc ctccgcagcc    420
ttccgcaggg gagatac                                                   437

<210> SEQ ID NO 23
<211> LENGTH: 137
<212> TYPE: DNA
<213> ORGANISM: Homo sapiens

<400> SEQUENCE: 23
cggagcggct gctgacggcg ataagggaag gcaccatgtc ccacgcactt cacctaagca     60
acaatgaacg ggcacctcta cagtcaccaa gtggaagatg atctgtttca acggggaag    120 tctgcagtaa aaatgac                                                   137

<210> SEQ ID NO 24
<211> LENGTH: 63
<212> TYPE: DNA
<213> ORGANISM: Homo sapiens

<400> SEQUENCE: 24
cgtgtctcgg actttgtact gactcacggc aagaagccac aaggcggggt tggtttccag     60
ctc                                                                   63

<210> SEQ ID NO 25
<211> LENGTH: 173
<212> TYPE: DNA
<213> ORGANISM: Homo sapiens

<400> SEQUENCE: 25
cgacacgcgc ttctctggca gaggaggagg agaggttgtt cctatgaact aagccacgtg     60
cagagaatgg tctgataact gaaactcaaa ccagagagtc ggggaataat ttcgtgatgc    120
tgctggcatt tccttttgtc ttcaatctgc tgcttcgcac actaagattt tga           173

<210> SEQ ID NO 26
<211> LENGTH: 30
<212> TYPE: DNA
<213> ORGANISM: Homo sapiens

<400> SEQUENCE: 26
actcagcaat tctaaacagc catgactttt                                       30

<210> SEQ ID NO 27
<211> LENGTH: 12
<212> TYPE: DNA
<213> ORGANISM: Homo sapiens

<400> SEQUENCE: 27
gaagagttgc aa                                                          12

<210> SEQ ID NO 28
<211> LENGTH: 13
<212> TYPE: DNA
<213> ORGANISM: Homo sapiens

<400> SEQUENCE: 28
gtacctatac ttg                                                         13

<210> SEQ ID NO 29
<211> LENGTH: 25
<212> TYPE: DNA
<213> ORGANISM: Homo sapiens

<400> SEQUENCE: 29
tcaagaagac ttacattttt cttcc                                            25

<210> SEQ ID NO 30
<211> LENGTH: 265
<212> TYPE: DNA
<213> ORGANISM: Homo sapiens

<400> SEQUENCE: 30
cgttcgggag tggctgtgcg aggggtggg caaagggcag agagtgagcc tgggattac         60 cgtaagtgag gatgtagagg ggcttcccgt tggtgtccat ggtggtcagg cagggcgcct      120
tgggcgagat ggtgccccac ctctgcagtg cggcctccac cgacggcggc cagttcgtga      180
ccacgcccag ctgctctccg cgcatggcca gcatctgggc ccctccggc tttggttggt      240 tcggatccgg ttgttgaact aaatc                                           265

<210> SEQ ID NO 31
<211> LENGTH: 128
<212> TYPE: DNA
<213> ORGANISM: Homo sapiens

<400> SEQUENCE: 31
cggttccctg cggtgctggc cacccgctcc cgagccgcag cttctcggac gtcgcacacc       60
ccgatgtggg cagagcggaa tgttctcctc ggcgctcctt cactgtgctg cagtctacac      120
cgaaccac                                                              128

<210> SEQ ID NO 32
<211> LENGTH: 21
<212> TYPE: DNA
<213> ORGANISM: Homo sapiens

```
<400> SEQUENCE: 32
cggcttgtgc tgagtgctcg c                                          21

<210> SEQ ID NO 33
<211> LENGTH: 5
<212> TYPE: DNA
<213> ORGANISM: Homo sapiens

<400> SEQUENCE: 33 gctca                                                             5

<210> SEQ ID NO 34
<211> LENGTH: 57
<212> TYPE: DNA
<213> ORGANISM: Homo sapiens

<400> SEQUENCE: 34
cgtggcgtgc ggggacgccg tgggcgtggt gtgaggtatg tggcgtgcgg ggacgcc    57

<210> SEQ ID NO 35
<211> LENGTH: 71
<212> TYPE: DNA
<213> ORGANISM: Homo sapiens

<400> SEQUENCE: 35
cgctcttccg cctgagccgc cgcctgacc tgacaggcca ccctgtgac tgatcagtga   60 cttgagctaa t                                                     71

<210> SEQ ID NO 36
<211> LENGTH: 382
<212> TYPE: DNA
<213> ORGANISM: Homo sapiens

<400> SEQUENCE: 36
cgggcagagg gacagaagga gccagcgtct gagctgctcc cgggccacac agcaagcaag   60
gaagtcacgg gtccttgtcc ctggccaaga ggtcccagag gccacaggaa acgctgggcg  120
cccgaagccc tatttctctg tctctagaga gtgggaaagg ggcccaggac cctcaccgga  180
agcacggtcg gaggggtcga cacgtccctc tcggacttgg cggggtagc acagtacgtc   240 tccaggaggg ccaggtcaca gctgcggaaa cagcactcct caacgatgcc acggctgcga   300
cggctcacac ggcttgcggg cctgcctgga agtcccacag cacagagaga gccgtgttag   360
caccgcactg accccagccc cc                                          382

<210> SEQ ID NO 37
<211> LENGTH: 196
<212> TYPE: DNA
<213> ORGANISM: Homo sapiens

<400> SEQUENCE: 37
cgggaagttc tgtccctgct cccgagtgtg cccagagtcc tgccgtttcc ttctagcgcg   60
cgttctttac tggcgccatt cctgctgcta agagccctga gacggccggg ggtgacccgg  120
gcccagagca gctcccggct cagggacccc tccccaggcc aagggcagga caagcccggg  180
cctgggcctc cgcctc                                                196

<210> SEQ ID NO 38
<211> LENGTH: 172
<212> TYPE: DNA
<213> ORGANISM: Homo sapiens
```

<400> SEQUENCE: 38
cgcgttgccg cccagaattt gcgctggagg aattccagct tcatttggac gcccgcggct    60
acagggcaga aagagagagg gcaaggccag ggaagagacg gggagagaaa aaaatagagt   120
caagttaaag agaggaggtg cttccgcagg aactgaggag agagaccgca gc           172

<210> SEQ ID NO 39
<211> LENGTH: 65
<212> TYPE: DNA
<213> ORGANISM: Homo sapiens

<400> SEQUENCE: 39
cggtggtgtt atacacggca gtgacgcgca gcccgccact gcccccgtgg ctgggctgag    60
tgccc                                                                65

<210> SEQ ID NO 40
<211> LENGTH: 79
<212> TYPE: DNA
<213> ORGANISM: Homo sapiens

<400> SEQUENCE: 40
cgcggttgtt ttccttcttt tggggtggaa gggagtgtgc agaggtggcc atgtgtctaa    60
gcgtgtgtgt gcgctgagc                                                 79

<210> SEQ ID NO 41
<211> LENGTH: 92
<212> TYPE: DNA
<213> ORGANISM: Homo sapiens

<400> SEQUENCE: 41
cgtctgggcc agggagataa tggtgctgaa cgcaagggca agtgttcgcg ttgtaggcgg    60
cgggacacag tgccggaaag caatctgatg cc                                  92

<210> SEQ ID NO 42
<211> LENGTH: 68
<212> TYPE: DNA
<213> ORGANISM: Homo sapiens

<400> SEQUENCE: 42
cacgcagctc tcccagcagc ccatgcctgg agacagagga cactgaggag cacgcgtgtc    60
cccaggat                                                             68

<210> SEQ ID NO 43
<211> LENGTH: 118
<212> TYPE: DNA
<213> ORGANISM: Homo sapiens

<400> SEQUENCE: 43
cggggacaca gccagctccc cccatgagct ggtggcctcg tcaggaagac ggccacaggg    60
cgctcttggg aggacccttg ggacagtggg caggcgctgg gcaagccaca agcgtgtc     118

<210> SEQ ID NO 44
<211> LENGTH: 60
<212> TYPE: DNA
<213> ORGANISM: Homo sapiens

<400> SEQUENCE: 44
cggccgaccg cggcccctcg cccgctcccg ccccgccgc ctccccgcag cccgggtccc     60

<210> SEQ ID NO 45
<211> LENGTH: 7
<212> TYPE: DNA
<213> ORGANISM: Homo sapiens

<400> SEQUENCE: 45 cgcaccg                                                                    7

<210> SEQ ID NO 46
<211> LENGTH: 221
<212> TYPE: DNA
<213> ORGANISM: Homo sapiens

<400> SEQUENCE: 46
cgtatctgaa ggaaacagat gttcggtaca cggacgacgc cgactctccc atcaccaagc          60
tgccctcggt tgcccaggag agccacagtg ccttgagaac ataagcaatt tagtgaacag         120
agttcttttc agaatttcct ttttcttaag taagcatctc tgttacttaa tttctcacca         180
cagctagatg tctataatct gccccaaaaa gaaaagaaag c                             221

<210> SEQ ID NO 47
<211> LENGTH: 74
<212> TYPE: DNA
<213> ORGANISM: Homo sapiens

<400> SEQUENCE: 47
cggagcaggc agaaaggcat attccgcttc gtctggtgat gggcatcggg agtctctggc          60
cgagtcagct cctc                                                            74

<210> SEQ ID NO 48
<211> LENGTH: 112
<212> TYPE: DNA
<213> ORGANISM: Homo sapiens

<400> SEQUENCE: 48
cgggaggggg ctgggaggct gggcagcacc tggaagtgga tgagggcgat tgtgagcgag          60
gccccgcgcc gatggtaggg accaggccac agccctttcc ccaggagccg gc                 112

<210> SEQ ID NO 49
<211> LENGTH: 74
<212> TYPE: DNA
<213> ORGANISM: Homo sapiens

<400> SEQUENCE: 49
cggaaccaac cctcctggcc atgggagggg ccgtggtgga cgagggcccc acaggcgtca          60
aggcccctga cggc                                                            74

<210> SEQ ID NO 50
<211> LENGTH: 164
<212> TYPE: DNA
<213> ORGANISM: Homo sapiens

<400> SEQUENCE: 50
cgtgttcatc ctggcggggg ccgaggtgct cacctcctcc ctgatttgc tgctgggcaa           60 cttcttctgc attaggaaga agcccaaaga gccacagcct gaggtggcgg ccgcggagga         120
ggagaagctc cacaagcctc ctgcagactc gggggtggac ttgc                          164

<210> SEQ ID NO 51
<211> LENGTH: 67

```
<212> TYPE: DNA
<213> ORGANISM: Homo sapiens

<400> SEQUENCE: 51
cgcttttcag aaacgaggct catcgcactg gcctgggggc gcgaggacga ggccgtgggt    60
agtgggc                                                             67

<210> SEQ ID NO 52
<211> LENGTH: 119
<212> TYPE: DNA
<213> ORGANISM: Homo sapiens

<400> SEQUENCE: 52
cgcatggaag gaaacgccat tgctgggcag tgttgcagcc tccgcagagg tgtgtgggct    60
ccggggagag ggacgtgctg gccctgtgc agtggcgtgg cccgtgtcct ttccccgcc    119

<210> SEQ ID NO 53
<211> LENGTH: 66
<212> TYPE: DNA
<213> ORGANISM: Homo sapiens

<400> SEQUENCE: 53
cgttcaggcc ctggcagctc cgttctggcc ctcatcattc ccagcataga gaaacaaaac    60
tcctgc                                                              66

<210> SEQ ID NO 54
<211> LENGTH: 8
<212> TYPE: DNA
<213> ORGANISM: Homo sapiens

<400> SEQUENCE: 54 agaggcag                                                             8

<210> SEQ ID NO 55
<211> LENGTH: 35
<212> TYPE: DNA
<213> ORGANISM: Homo sapiens

<400> SEQUENCE: 55
ggctgtcact gtcacggtat ctggcacaac cgcag                               35

<210> SEQ ID NO 56
<211> LENGTH: 42
<212> TYPE: DNA
<213> ORGANISM: Homo sapiens

<400> SEQUENCE: 56
acacagagca agcagcggcc agagacagac ccaggccgtc tt                       42

<210> SEQ ID NO 57
<211> LENGTH: 293
<212> TYPE: DNA
<213> ORGANISM: Homo sapiens

<400> SEQUENCE: 57
cggaggttgc aggcgttcgg gggtgggggg tcggcaggca gagctggaac cacccctagga   60 accacccaga gacggggagg tcaggggcaa ggacggcacg cagggccacc tccctgcgcc   120
cgcctggttc ctgggggctc agtgccctca gcagctctcg cccacaccct acagtcacag   180
ctccagtcag tgcctcctca gcaggctcga gtctgggtct gcgcagccgc ctgtggcctg   240
```

```
agctccagct ggcctgtctg gttcctgccg ccacacgccc cactctggct gac         293
```

<210> SEQ ID NO 58
<211> LENGTH: 241
<212> TYPE: DNA
<213> ORGANISM: Homo sapiens

<400> SEQUENCE: 58

```
cgctgacatt tattgagcgc ttagtgtcta cctctcccct ccctgaacct gtgccatccc    60
gatagtgccg gagctctctt catctccgtc ttccagatgg ggaaactgag gctcagggtc   120
acacagcctg tagcaggcaa agccagggtt ctagccgcga ccgtccgggt cggtcctggt   180
gccgagaggt agtgctgggt gtcgggagcc aggccctcca gctggggctg agagctttcc   240
c                                                                    241
```

<210> SEQ ID NO 59
<211> LENGTH: 142
<212> TYPE: DNA
<213> ORGANISM: Homo sapiens

<400> SEQUENCE: 59

```
cgcccgggag ctgcgcacct ccagcaggca cccagtctaa acaagcacaa ggaaacacac    60
aacatacgtg gaagctggag ccggcgctgg ccagagcggc ccggtaatgc ctgacatgtg   120
ttgggttgtt tgtgaacctg cc                                            142
```

<210> SEQ ID NO 60
<211> LENGTH: 248
<212> TYPE: DNA
<213> ORGANISM: Homo sapiens

<400> SEQUENCE: 60

```
cggtccccca gcccatccgc catccccagc ccgtggtcag gtagagagtg agccccacgc    60
cgccccaggg aggaggcgcc agagcgcggg gcagacgcaa agtgaaataa acactatttt   120
gacggctgtc tttatatttt ctgagcacac acagagccct ggcgtccacc ggggcaggcg   180
caaagtggac agagcatgca gggcggcgga cccccccacg accctcctcg ccctgtctcc   240
atcccctc                                                            248
```

<210> SEQ ID NO 61
<211> LENGTH: 475
<212> TYPE: DNA
<213> ORGANISM: Homo sapiens

<400> SEQUENCE: 61

```
cgaccagcac acacagccca aggagcgcgg cactccacag ctttccatca ccgcaaggca    60
ggcaagcaca gcaaccgtgg ccccgcccct ccctgtggac aaccccacac ctatgcggca   120
aaccgcagcc gccccgatca agatggcac ccaggtgggc ggggcttgaa cagaccgtcc   180
cgcccatgcc acctgcagcc acttcagcct tgccccgccg catctgccgc caaccaatcc   240
gggcaacgcc tgcgcggcaa acctcagctg cccccatcaa agatggcgcc caggcgggcg   300
ggccttgtct cgcccaacca actaggacag cgcctgcgca gcaaatctca agcactttca   360
ttaaagatgg cgcccaggtg ggtggggctt gaacaaacca ctaggtccaa tgccaccctg   420
tcacttcagc cttgccccgc cccatctgcc accaaccaac caggacagca cctgc        475
```

<210> SEQ ID NO 62
<211> LENGTH: 73

<212> TYPE: DNA
<213> ORGANISM: Homo sapiens

<400> SEQUENCE: 62
gcccggcgcc cggcggcgcc accagcccag ggtggacatc tcccgcgcct cccaaacctc    60
tcctcccgca gct    73

<210> SEQ ID NO 63
<211> LENGTH: 32
<212> TYPE: DNA
<213> ORGANISM: Homo sapiens

<400> SEQUENCE: 63
cccagacttc tgcaccgagg tgcagctcga cg    32

<210> SEQ ID NO 64
<211> LENGTH: 479
<212> TYPE: DNA
<213> ORGANISM: Homo sapiens

<400> SEQUENCE: 64
cgacgtcttc gagcgcttcg tggccgccga gcagtcggtg gccctgggcg aggaggtgcg    60
gcgcagctac tgcccggcgc gtcccggcca gcggcgcgta ctcatcaacc tgtactgctg   120
cgcggcagag gatgcgcgct tcatcaccga ccccggcgtg cgcaaatgcg gcgcgctcag   180
cctcgagctt gagcccgccg actgcggcca ggacaccgcc ggcgcgcctc ccggccgccg   240
cgagatccgc gccgccatgc agtttggcga caccgaaatt aaggtcaccg ccgtcgacgt   300
cagcaccaat cgctccgtgc gcgcgtccat cgactttctt ccaactgag ggcgcgccgg   360 cgcggtgcca gcgccgtctg cccggccccg ccctctttcg gttcagggc ctgcggagcg   420 ggttggggcg ggggaaacga tagttctgca gtctgcgcct ttccacgccc tccagcccc   479

<210> SEQ ID NO 65
<211> LENGTH: 229
<212> TYPE: DNA
<213> ORGANISM: Homo sapiens

<400> SEQUENCE: 65
agaggatgcg cgcttcatca ccgacccggg cgtgcgcaaa tgcggcgcgc tcagcctcga    60
gcttgagccc gccgactgcg gccaggacac cgccggcgcg cctcccggcc gccgagat    120 ccgcgccgcc atgcagtttg gcgacaccga aattaaggtc accgccgtcg acgtcagcac   180
caatcgctcc gtgcgcgcgt ccatcgactt tctttccaac tgagggcgc    229

<210> SEQ ID NO 66
<211> LENGTH: 210
<212> TYPE: DNA
<213> ORGANISM: Homo sapiens

<400> SEQUENCE: 66
cgggccagct tctcacctca tagggtgtac ctttcccggc tccagcagcc aatgtgcttc    60
ggagccactc tctgcagagc cagagggcag gccggcttct cggtgtgtgc ctaagaggat   120
ggatcggagg tccgggctc agcagtggcg ccgagctcgc cataattaca acgacctgtg   180
cccgcccata ggccgccggg cagccaccgc   210

<210> SEQ ID NO 67
<211> LENGTH: 69
<212> TYPE: DNA

<213> ORGANISM: Homo sapiens

<400> SEQUENCE: 67

```
cgccatacac ccgcccccca ccggcttcca accaccccag cagcacctct tcgggcgttc    60
caacgcggc                                                            69
```

<210> SEQ ID NO 68
<211> LENGTH: 163
<212> TYPE: DNA
<213> ORGANISM: Homo sapiens

<400> SEQUENCE: 68

```
gaaaagatgg gctacatgtg tacgcaccgc ctgctgcttc taggtaatgc ggcggactct    60
gcctgcgggc agcagggccg ccggggaacc ggggagggg tggcagggct gcctggtggg    120
gctaggggct ccgcagtggg aggaggggt ccagccaaag gcg                       163
```

<210> SEQ ID NO 69
<211> LENGTH: 478
<212> TYPE: DNA
<213> ORGANISM: Homo sapiens

<400> SEQUENCE: 69

```
cgcgcctttg cacttttctt tttgagttga catttcttgg tgcttttgg tttctcgctg     60 ttgttgggtg cttttggtt tgttcttgtc ccttttcgt ttgctcatcc tttttggcgc     120
taactcttag gcagccagcc cagcagcccg aagcccgggc agccgcgctc cgcggccccg    180
gggcagcgcg gcgggaaccg cagccaagcc ccccgacacg gggcgcacgg gggccgggca    240
gcccgaggcc gggggcaagc agggagcccg ggccaggcgc gagccgagct ccccgaggtg    300
gccgggccac catgctgaag atggccatga agctcaaagc ccggggcggcg agagcgaga    360 agaagacggc cgcggcggct gccgaggtgg ctgccgaagc tgcggcggcg gctgcggcgt    420
tggccgagcc gagagagccg ctcgcgccgc ggaagagcgg ggaccccgag aagctcgc     478
```

<210> SEQ ID NO 70
<211> LENGTH: 78
<212> TYPE: DNA
<213> ORGANISM: Homo sapiens

<400> SEQUENCE: 70

```
gatgccccga ggccgccgcc gccgcggccg ccgccgacga cgacgagggc gccgaggagg    60
gcgccgtcgg gggcgccg                                                  78
```

<210> SEQ ID NO 71
<211> LENGTH: 83
<212> TYPE: DNA
<213> ORGANISM: Homo sapiens

<400> SEQUENCE: 71

```
cggtggcccg cactaacttc cttagaggtg atgctgatgc tgtatgttgg agacgcttct    60
gagtgtcctc ggaacgttcc cac                                            83
```

<210> SEQ ID NO 72
<211> LENGTH: 89
<212> TYPE: DNA
<213> ORGANISM: Homo sapiens

<400> SEQUENCE: 72

```
gccgaggagg ggccggcagc gcctcccttc ctgcccacag agcagccgcc ttgtgcccat    60
```

```
ctattccccg gctctgcatg gggcctctg                                              89

<210> SEQ ID NO 73
<211> LENGTH: 11
<212> TYPE: DNA
<213> ORGANISM: Homo sapiens

<400> SEQUENCE: 73
gcagtgtcag g                                                                 11

<210> SEQ ID NO 74
<211> LENGTH: 72
<212> TYPE: DNA
<213> ORGANISM: Homo sapiens

<400> SEQUENCE: 74
ctccttctgc ccctgcagtg ggtgttacgg gcggtgtgcc ctggcgagca agctttgatt            60
cttggttctt tg                                                                72

<210> SEQ ID NO 75
<211> LENGTH: 6
<212> TYPE: DNA
<213> ORGANISM: Homo sapiens

<400> SEQUENCE: 75 agctcg                                                                        6
```